United States Patent
Stadheim et al.

(10) Patent No.: US 11,959,118 B2
(45) Date of Patent: *Apr. 16, 2024

(54) Fc-CONTAINING POLYPEPTIDES HAVING IMPROVED PROPERTIES AND COMPRISING MUTATIONS AT POSITIONS 243 AND 264 OF THE Fc-REGION

(71) Applicant: Merck Sharp & Dohme Corp., Rahway, NJ (US)

(72) Inventors: Terrance A. Stadheim, Lyme, NH (US); Dongxin Zha, Houston, TX (US); Liming Liu, Ambler, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 647 days.

This patent is subject to a terminal disclaimer.

(21) Appl. No.: 17/075,343

(22) Filed: Oct. 20, 2020

(65) Prior Publication Data

US 2021/0047670 A1     Feb. 18, 2021

Related U.S. Application Data

(60) Continuation of application No. 16/007,590, filed on Jun. 13, 2018, now Pat. No. 10,858,686, which is a continuation of application No. 14/931,354, filed on Nov. 3, 2015, now abandoned, which is a division of application No. 13/699,213, filed as application No. PCT/US2011/037826 on May 25, 2011, now Pat. No. 9,187,552.

(60) Provisional application No. 61/348,968, filed on May 27, 2010.

(51) Int. Cl.

| C12P 21/00 | (2006.01) |
|---|---|
| C07K 16/00 | (2006.01) |
| C07K 16/24 | (2006.01) |
| C07K 16/28 | (2006.01) |
| C07K 16/32 | (2006.01) |
| C07K 16/40 | (2006.01) |
| A61K 39/00 | (2006.01) |

(52) U.S. Cl.
CPC .......... *C12P 21/005* (2013.01); *C07K 16/00* (2013.01); *C07K 16/241* (2013.01); *C07K 16/2863* (2013.01); *C07K 16/32* (2013.01); *C07K 16/40* (2013.01); *A61K 2039/505* (2013.01); *C07K 2317/14* (2013.01); *C07K 2317/41* (2013.01); *C07K 2317/51* (2013.01); *C07K 2317/515* (2013.01); *C07K 2317/52* (2013.01); *C07K 2317/71* (2013.01); *C07K 2317/732* (2013.01); *C07K 2317/734* (2013.01)

(58) Field of Classification Search
CPC .............. C12P 21/005; C07K 2317/41; C07K 2317/52; C07K 2317/90
USPC ...................................... 424/133.1
See application file for complete search history.

(56) References Cited

U.S. PATENT DOCUMENTS

| 4,439,196 | A | 3/1984 | Higuchi |
|---|---|---|---|
| 4,447,224 | A | 5/1984 | DeCant, Jr. et al. |
| 4,447,233 | A | 5/1984 | Mayfield |
| 5,272,066 | A | 12/1993 | Bergh et al. |
| 5,714,377 | A | 2/1998 | Tanner et al. |
| 5,830,465 | A | 11/1998 | Fukuda et al. |
| 6,156,881 | A | 12/2000 | Seed et al. |
| 7,029,872 | B2 | 4/2006 | Gerngross |
| 7,198,921 | B2 | 4/2007 | Miura et al. |
| 7,217,548 | B2 | 5/2007 | Yoshida et al. |
| 7,244,601 | B2 | 7/2007 | Gilbert et al. |
| 7,259,007 | B2 | 8/2007 | Bobrowicz et al. |
| 7,326,681 | B2 | 2/2008 | Gerngross |
| 7,449,308 | B2 | 11/2008 | Gerngross et al. |
| 7,863,020 | B2 | 1/2011 | Hamilton |
| 7,931,895 | B2 | 4/2011 | Beliard et al. |
| 8,362,210 | B2 * | 1/2013 | Lazar ................. C07K 16/2878 424/134.1 |
| 9,187,552 | B2 | 11/2015 | Stadheim et al. |
| 9,193,798 | B2 | 11/2015 | Lazar et al. |
| 9,394,366 | B2 | 7/2016 | Chu et al. |
| 11,427,627 | B2 * | 8/2022 | Du ....................... C07K 16/00 |
| 2003/0118583 | A1 | 10/2003 | Emery |
| 2004/0230042 | A1 | 11/2004 | Hamilton |
| 2005/0054832 | A1 | 3/2005 | Lazar et al. |
| 2005/0170452 | A1 | 8/2005 | Wildt et al. |
| 2005/0208617 | A1 | 9/2005 | Bobrowicz et al. |
| 2005/0255489 | A1 | 11/2005 | Pierce et al. |
| 2005/0260729 | A1 | 11/2005 | Hamilton |
| 2006/0040353 | A1 | 2/2006 | Davidson et al. |
| 2006/0211085 | A1 | 9/2006 | Bobrowicz |
| 2006/0234345 | A1 | 10/2006 | Schwartz et al. |

(Continued)

FOREIGN PATENT DOCUMENTS

| AU | 2009206506 | * | 1/2009 |
|---|---|---|---|
| CN | 1867583 | | 11/2006 |

(Continued)

OTHER PUBLICATIONS

Go et al (J Proteome Res. Mar. 1, 2013;12(3):1223-34. doi: 10.1021/pr300870t. Epub Feb. 20, 2013).*

(Continued)

*Primary Examiner* — Lynn A Bristol

(74) *Attorney, Agent, or Firm* — John David Reilly; Anna Cocuzzo

(57) ABSTRACT

The present invention is directed to methods and compositions for the production of Fc-containing polypeptides having improved properties and comprising mutations at positions 243 and 264 of the Fc region.

13 Claims, 34 Drawing Sheets

Specification includes a Sequence Listing.

(56) References Cited

U.S. PATENT DOCUMENTS

| | | |
|---|---|---|
| 2006/0275282 A1 | 12/2006 | Moore et al. |
| 2006/0286637 A1 | 12/2006 | Hamilton |
| 2007/0037248 A1 | 2/2007 | Bobrowicz et al. |
| 2007/0041979 A1 | 2/2007 | Raju et al. |
| 2007/0067855 A1 | 3/2007 | Jarvis et al. |
| 2007/0122403 A1 | 5/2007 | Dall'Acqua et al. |
| 2007/0184063 A1 | 8/2007 | Holgersson et al. |
| 2008/0112961 A1 | 5/2008 | Stavenhagen et al. |
| 2008/0206242 A1 | 8/2008 | Lawrence et al. |
| 2008/0206246 A1 | 8/2008 | Ravetch et al. |
| 2008/0292621 A1 | 11/2008 | Lazar et al. |
| 2009/0215991 A1 | 8/2009 | Lazar et al. |
| 2010/0040601 A1 | 2/2010 | Cantin et al. |
| 2010/0137565 A1 | 6/2010 | Javaud et al. |
| 2010/0173323 A1 | 7/2010 | Strome et al. |
| 2014/0302028 A1* | 10/2014 | Zha .................. C07K 16/18 435/69.6 |
| 2016/0176950 A1 | 6/2016 | Ravetch et al. |
| 2016/0215061 A1 | 7/2016 | Shaheen et al. |
| 2017/0101466 A1 | 4/2017 | Handa et al. |
| 2018/0142233 A1 | 5/2018 | Shaheen et al. |
| 2022/0025071 A1* | 1/2022 | Capon ................ C07K 16/283 |
| 2023/0071196 A1* | 3/2023 | Brannetti ............... A61P 35/00 |

FOREIGN PATENT DOCUMENTS

| | | |
|---|---|---|
| CN | 101432301 | 11/2006 |
| CN | 100035 | 6/2014 |
| EP | 2233500 A1 | 9/2010 |
| IN | 101343635 | 1/2009 |
| JP | 2008537941 | 10/2008 |
| JP | 201091308 | 4/2010 |
| RU | 2337107 C2 | 10/2008 |
| WO | 1992009694 A2 | 6/1992 |
| WO | 1995007020 A1 | 3/1995 |
| WO | 199621038 A1 | 7/1996 |
| WO | 199734631 A1 | 9/1997 |
| WO | 9957134 A1 | 11/1999 |
| WO | 2000014251 A2 | 3/2000 |
| WO | 200042072 A2 | 7/2000 |
| WO | 200200856 A2 | 1/2002 |
| WO | 03074679 A2 | 9/2003 |
| WO | 2004029207 A2 | 4/2004 |
| WO | 2004099249 A2 | 11/2004 |
| WO | 2005033325 A1 | 4/2005 |
| WO | 2005056759 A2 | 6/2005 |
| WO | 2005077981 A2 | 8/2005 |
| WO | 2005092925 A2 | 10/2005 |
| WO | 2005102387 A2 | 11/2005 |
| WO | 2006019447 A1 | 2/2006 |
| WO | 2006047350 A2 | 5/2006 |
| WO | 2006085967 A2 | 8/2006 |
| WO | 2006105338 A2 | 10/2006 |
| WO | 2006107990 A2 | 10/2006 |
| WO | 2007/005786 A2 | 1/2007 |
| WO | 2007008943 A2 | 1/2007 |
| WO | 2007/024743 A2 | 3/2007 |
| WO | 2007041635 A2 | 4/2007 |
| WO | 2007044616 A2 | 4/2007 |
| WO | 2007061631 A2 | 5/2007 |
| WO | 2007087420 A2 | 8/2007 |
| WO | 20070120932 A2 | 10/2007 |
| WO | 2008022152 A2 | 2/2008 |
| WO | WO 2008022152 * | 2/2008 |
| WO | 2008036688 A2 | 3/2008 |
| WO | WO 2008036688 * | 3/2008 |
| WO | 2008057240 A2 | 5/2008 |
| WO | 2008091798 A2 | 7/2008 |
| WO | 2008091954 A2 | 7/2008 |
| WO | 2008092117 A2 | 7/2008 |
| WO | 2008098115 A2 | 8/2008 |
| WO | 20080093165 A2 | 8/2008 |
| WO | 2008121160 A2 | 10/2008 |
| WO | 2008150494 A1 | 12/2008 |
| WO | 2008156676 A1 | 12/2008 |
| WO | 200979382 A1 | 6/2009 |
| WO | 2009155513 A2 | 12/2009 |
| WO | 2010033736 A1 | 3/2010 |
| WO | 2010051391 A1 | 5/2010 |
| WO | 2010106180 A2 | 9/2010 |
| WO | 2011120134 A8 | 10/2011 |
| WO | 2011120135 A8 | 10/2011 |
| WO | 2011149999 A2 | 12/2011 |
| WO | 2013074598 A1 | 5/2013 |
| WO | 2014113510 A1 | 7/2014 |

OTHER PUBLICATIONS

Bruhlmann et al (Biotechnol Bioeng. May 2019;116(5):1017-1028. doi: 10.1002/bit.26930. Epub Feb. 27, 2019).*
U.S. Appl. No. 16/007,590, filed Jun. 13, 2018.
U.S. Appl. No. 14/931,354, filed Nov. 3, 2015.
U.S. Appl. No. 14/884,871, filed Oct. 16, 2015.
U.S. Appl. No. 13/699,213, filed Nov. 20, 2012.
Abes, Impact of Glycosylation on Effector Functions of Therapeutic IgG, Pharmaceuticals, 2010, pp. 146-157, 3.
Anthony et al., A Novel Role for the IgG Fc Glycan: The anti-inflammatory activity of sialylated IgG Fcs, J. Clin. Immunol., 2010, pp. S9-S14, 30.
Anthony et al., Intravenous Gammaglobulin Suppresses Inflammation through a novel TH2 Pathway, Nature, 2011, pp. 1-5, 1.
Anthony et al., Science, Science, 2008, pp. 373-376, 320.
Armour et al., Recombinant Human IgG Molecules Lacking Fcγ receptor I Binding and Monocyte Triggering Activities, Eur. J. Immunol., 1999, pp. 2613-2624, 29.
Baert et al., Influence of Immunogenicity on the long term efficacy of Infliximab in Crohns disease, New England Journal Med., 2003, pp. 601-608, 348.
Barb et al., Branch-Specific Sialylation of IgG-Fc Glycans by ST6Gal-I, Biochemistry, 2009, pp. 9705-9707, 48.
Baudino et al., Crucial Role of aspartic acid at position 265 in the CH2 domain for muri e IgG2a and IgG2b Fc-assiciated effector functions, J. Immunology, 2008, pp. 6664-6669, vol. 181.
Baumann et al., Recognition of Secretery IgA by DC-SIGN: Implications for Immune Surveillance in the Intestine, Immunol. Lett., 2010, pp. 59-55, 131.
Baumeister et al., Novel Human Expression System Glycoengineered for Optimal Glycosylation of Biotherapeutics, BioProcess International, 2006, pp. 2-6, 1.
Baumeister, A Novel Human Expression System for Generating Glycoprotein with Higher Activity, Fully Human Glycosylation and Optimised Sialylation, Bioprocess Journal, 2005, pp. 45-47, 1.
Beniaminovitz et al., Prevention of rejection in cardiac transplantation by blockade of the interleukin 2 receptor with a monoclonal antibody, New England Journal of Medicine, 2000, pp. 613-619, 342.
Bragonzi et al., Biochimica et Biophysica Acta BBA, Biochimica et Biophysica, 2000, pp. 273-282, 1474.
Bretthauer et al., Methods in Molecular Biology, Pichia Protocols Second Edition, 2007, pp. 107-118, 389.
Castilho et al., J. Biol. Chem., J. Biol. Chem., 2010, pp. 15923-15930, 285.
Cheong et al., New Monoclonal Anti-mouse DC-SIGN Antibodies Reactive with Acetone-fixed Cells, J. Immunol. Methods, 2010, pp. 66-75, 360.
Cho et al., Characterization of Host-Cell Line Specific Glycosylation Profiles of Early Transmitted/Founder HIV-1 gp120 Envelope Proteins, Journal of Proteome Research, 2013, Issue 3, pp. 1223-1234, 12.
Choi et al., PNAS, PNAS, 2003, pp. 5022-5027, 100.
Chu et al., Molecular Immunology, Immunology, 2008, pp. 3926-3933, 45.
Cox et al., Nature Biotechnology, Nature Biotechnology, 2006, pp. 1591-1597, 24.
Dalziel et al., Lectin Analysis of Human Immunoglobulin G, N-Glycan, Glycoconjugate Journal, 1999, pp. 801-807, 16.

(56) References Cited

OTHER PUBLICATIONS

Debre et al., Infusion of Fc gamma fragments for treatment of children wtih acute immune thrombocytopenic purpura, Infusion of Fc Gamma, 1993, pp. 945-949, 342.
Dimitrov et al., Sialylated Therapeutic IgG: A Sweet Remedy for Inflammatory Diseases, Nephrol. Dial Transplant, 2007, pp. 1301-1304, 22.
Dschietzig et al., Biochem. Biophys. Res. Comm., Biochem. Biophys Res. Chem., 2001, pp. 245-251, 289.
Duncan et al., Localization of the Binding Site for the Human High-affinity Fc receptor on IgG, Nature, 1988, pp. 563-564, 332.
Durandy, Intravenous Immunoglobulins—Understanding Properties and Mechanisms, British Society for Immunology, Clinical and Experimental Immunology, 2009, pp. 2-13, 158.
Gawlitzek et al., Biotechnol. Bioengin., Biotechnology and Bioengineering, 2009, pp. 1164-1175, 103.
Ghosh et al., Natalizumab for active Crohns disease, New England J. Med., 2003, pp. 24-32, 348.
Goto et al., Protein O-Glycosylation in Fungi, Biosci. Biotechnol. Biochem., 2007, pp. 1415-1427, 71.
Guhr et al., Enrichment of Sialylated 1gG Lectin Fractionation does not Enhance the Efficacy of Immunoglobulin Thrombocytopenia, Murine Model of Immune Thrombocytopenia, 2011, pp. 1-8, 6.
Hamilton et al., Science, Science, 2006, pp. 1441-1443, 313.
Harrison et al., Adv. Virus Res., Adv. Virus Res., 2006, pp. 159-191, 68.
Herold, ANTI-CD3 Monoclonal Antibody in New-Onset Type 1 Diabetes Mellitus, New England Journal of Medicine, 2002, pp. 1692-1698, 346.
Hodoniczky et al., Biotechnology Prog., Biotechnology Prog., 2005, pp. 1644-1652, 21.
Hossler, Optimal and Consistent Protein Glycosylation in Mammalian Cell Culture, Glycobiology, 2009, pp. 936-949, 19.
Hutchins, Improved bio distribution, tumor targeting and reduced immunogenicity in mice with a gamma 4 variant of CAMPATH-1H, Proc. Natl. Acad. Sci. USA, 1995, pp. 11980-11984, 92.
Idusogie et al., J. Immunology, Journal of Immunology, 2000, pp. 4178-4184, 164.
Jacobs et al., Nature Protocols, Nature Protocols, 2009, pp. 58-70, 4.
Jassal, Sialylation of Human IgG-Fc Carbohydrate by Transfected Rat Alpha 2,6-Sialyltransferase, Biochemical and Biophysical Research Communication, 2001, pp. 243-249, 286.
Jefferis et al., Chem. Immunol., Chem. Immunol., 1997, pp. 111-128, 65.
Jefferis et al., Modulation of Fc Gamma R and Human Complement Activation by IgG3-core Oligosaccharide Interactions, Immunology Letters, 1996, pp. 101-104, 54.
Jefferis et al., Nature Biotech., Nature Biotech., 2006, pp. 1230-1231, 24.
Jefferis et al., Recombinant antibody therapeutics: the impact of glycosylation on mechanisms of action, Trends in Pharmacological Sciences, 2009, pp. 356-362, 30.
Jones, Biochim. Biophys. Acta, Biochim. Biophys. Acta, 2005, pp. 121-137, 1726.
Kaneko et al., Science, Science, 2006, pp. 670-673, 313.
Kuroda, A Critical Role for Sialylation in Cryoglobulin Activity of Murine IgG3 Monoclonal Antibodies, the Journal of Immunology, 2005, pp. 1056-1061, 1.
Lee et al., J. Biol. Chem., Journal of Bio. Chemistry, 1989, pp. 13848-13855, 264.
Leontyev et al., Sialylation-independent mechanism involved in the amelioration of murine immune thrombocytopenia using intravenous gammaglobulin, Transfusion, 2011, pp. 1-7, 1.
Li et al., Inhibitory Fc Gamma Receptor Engagement Drives Adjuvant and Anti-tumor Activities of Agonistic CD40 Antibodies, Science, 2011, pp. 1030-1034, 333.
Lifely et al., Glycobiology, Glycobiology, 1995, pp. 813-822, 5.

Lipsky et al., Infliximab and methotrexate in the treatment of rheumatoid arthritis, New England Journal of Medicine, 2000, pp. 1594-1602, 343.
Liu et al., Randomised, double blind, placebo controlled study of interferon b-1a in relapsing-remitting multiple sclerosis analysed by area under disability/time curves, N. Neurol. Neurosurg. Psych., 1999, pp. 451-456, 67.
Lizak et al., Bioconjugate Chem., Bioconjugate Chem., 2011, pp. 488-496, 22.
Lund et al., Expression and Characterization of Truncated Forms of Humanized L243 IgG1, Eur. J. Biochem., 2000, pp. 7246-7256, 267.
Lund et al., J. Immunol., J. Immunol., 1996, pp. 4963-4969, 157.
Lussier et al., Cell Biology and Metabolism: The Ktr1p, Ktr3p, and Kre2p/Mnt1p Mannosyltransferases Participate in theElaboration of Yeast O- and N-linked Carbohydrate Chains, J. Biol. Chem., 1997, pp. 15527-15531, 272.
Milgrom et al., Treatment of allergic asthma with monoclonal anti IgE antibody, New England Journal Med., 1999, pp. 1966-1973, 341.
NA, JP Search, Search, NA, pp. 1-5, NA.
Nimmerjahn et al., J. Exp. Med., Journal Exp. Med., 2007, pp. 11-15, 204.
Nimmerjahn, Fc Gamma RIV: A Novel for with Distinct IgG Subclass Specifity, Immunity, 2005, pp. 41-51, 23.
Nimmerjahn, Manuscript, Fc Receptor ITP SIGNR1 Sialic Acid, 2011, pp. 1-14, 1.
Patel et al., Different Culture Methods lead to differences in glycosylation of a murine IgG monoclonal antibody, Biochem. J., 1992, pp. 839-845, 285.
Patel et al., Neonatal Fc Receptor Blockade Fc Engineering Ameliorates in a Murine Model, Fc Receptor, 2011, pp. 1015-1022, 1.
Portieji et al., Cancer Immunol. Immunother., Cancer Immunology, 2003, pp. 133-144, 52.
Presta et al., Molecular Engineering and Design of Therapeutic Antibodies, Current Opinion in Immunology, 2008, pp. 460-470, 20.
Radev et al., The Structure of a Human Type III Fc Gamma Receptor in Complex with Fc, the Journal of Biological Chemistry, 2001, pp. 16469-16477, 276.
Raju et al., Glycosylation in the Fc Domain of IgG Increases Resistance to Proteolytic Cleavage by Papain, Biochemical and Biophysical Research Communications, 2006, pp. 797-803, 341.
Raju, Glycoengineering of Therapeutic Glycoproteins: In Vitro Galactosylation and Sialylation of Glycoproteins with Terminal N-acetylglucosamine and Galactose Residues, Biochemistry, 2001, pp. 8868-8876, 40.
Raju, TS, Glycosylation variations with expression systems and their impact on biological activity of therapeutic immunoglobulins, BioProcess International, 2003, pp. 44-53.
Reddy, Elimination of Fc Receptor-department effector Functions of a Modified IgG4 Monoclonal Antibody to Human CD4, the American Association of Immunologists, 2000, pp. 1925-1933, 1.
Rook et al., Changes in IgG Glycoform Levels, Journal of Autoimmunity, 1991, pp. 779-794, 4.
Scallon et al., Higher levels of sialylated Fc glycans in immunoglobulin G molecules can adversely impact functionality, Molecular Immunology, 2007, pp. 1524-1534, 44.
Schauer et al., Biochem. Society Transactions, Biochem. Society, 1983, pp. 270-271, 11.
Schauer et al., Glycobiology, Glycobiology, 1991, pp. 449-452, 1.
Sheeley et al., Characterization of Monoclonal Antibody Glycosylation, Analytical Biochemistry, 1997, pp. 102-110, 247.
Sheilds et al., J. Biol. Chem., J. Biol. Chem., 2001, pp. 6591-6604, 276.
Shibuya et al., The Elderberry Sambucus Nigra Bark Lectin, Journal of Biological Chemistry, 1987, pp. 1596-1601, 262.
Shields et al., Lack of fucose on human IgG1 N linked oligosaccharide improves binding to human Fc gamma RIII and antibody dependent cellular toxicity, J. Biol. Chem., 2002, pp. 26733-26740, 277.
Shinkawa et al., The absence of fucose but not the presence of galactose or bisecting N acetylglucosamine of human IgG1 complex

(56) References Cited

OTHER PUBLICATIONS type oligosaccharide shows the critical role of enhancing antibody dependent cellular cytotoxicity, J. Biol. Chem., 2003, pp. 3466-3473, 278.

Slamon et al., Use of chemotherapy plus a monoclonal antibody against HER2 for metastatic breast cancer that overexpresses HER2, New England J. Med., 2001, pp. 783-792, 344.

Stadlmann et al., A Close Look at Human IgG Sialylation and Subclass Distribution After Lectin Fractionation, Proteomics, 2009, pp. 4143-4153, 9.

Stadlmann et al., Analytical and Functional Aspects of Antibody Sialylation, J. Clin. Immunol., 2010, pp. S15-S19, 30.

State Intellectual Property Office of People's Republic China, in connection with CN201180033821.X, Translation of Search Report, Translation, Translation of Search Report, NA.

Supplementary, EP Search Report, dated Apr. 14, 2017, corresponding to EP Application No. 11787290.3.

Tao, MH et al., Role of carbohydrate in the structure and effector functions mediated by the human IgG constant region, the Journal of Immunology, 1989, pp. 2595-2601, 143(8).

Umana et al., Engineered glycoforms of an antineuroblastoma IgG1 with optimized antibody dependent cellular cytotoxic activity, Nature Biotechnology, 1999, pp. 176-180, 17.

Vaccaro et al., Engineering the Fc region of immunoglobulin G to modulate in vivo antibody levels, Nature Biotechnology, 2005, pp. 1283-1287, 23.

Van De Geijn, Immunoglobin G Galactosylation and Sialyation are Associated with Pregnancy induced improvement of rheumatoid arthritis, Arthritis Research and Therapy, 2009, pp. R193-R203, 11.

Voynov et al., Dynamic Fluctuations of protein-carbohydrate interactions promote protein aggregation, Dynamic Fluctuations, 2009, pp. 1-10, 12.

Willer et al., O-mannosyl glycans: from yeast to novel associations with human disease, Curr. Opin. Struct. Biol., 2003, pp. 621-630, 13.

Wright E Tal., Trends in Biotechnology, Trends in Biotechnology, 1997, pp. 26-31, 15.

Yang et al., A Randomized Trial of Bevacizumab, an Anti-Vascular Endothelial Growth Factor Antibody, for Metastatic Renal Cancer, New England Journal of Medicine, 2003, pp. 427-434, 349.

Yasukawa et al., Inflammation-dependent changes in 2,3-, 2,6-, and 2,8-sialic acid glycotopes on serum glycoproteins in mice, Glycobiology, 2005, pp. 827-837, 15.

Yu et al., Engineering Hydrophobic Protein-Carbohydrate Interactions, J. Am. Chem. Soc., 2013, pp. 9723-9732, 135.

\* cited by examiner

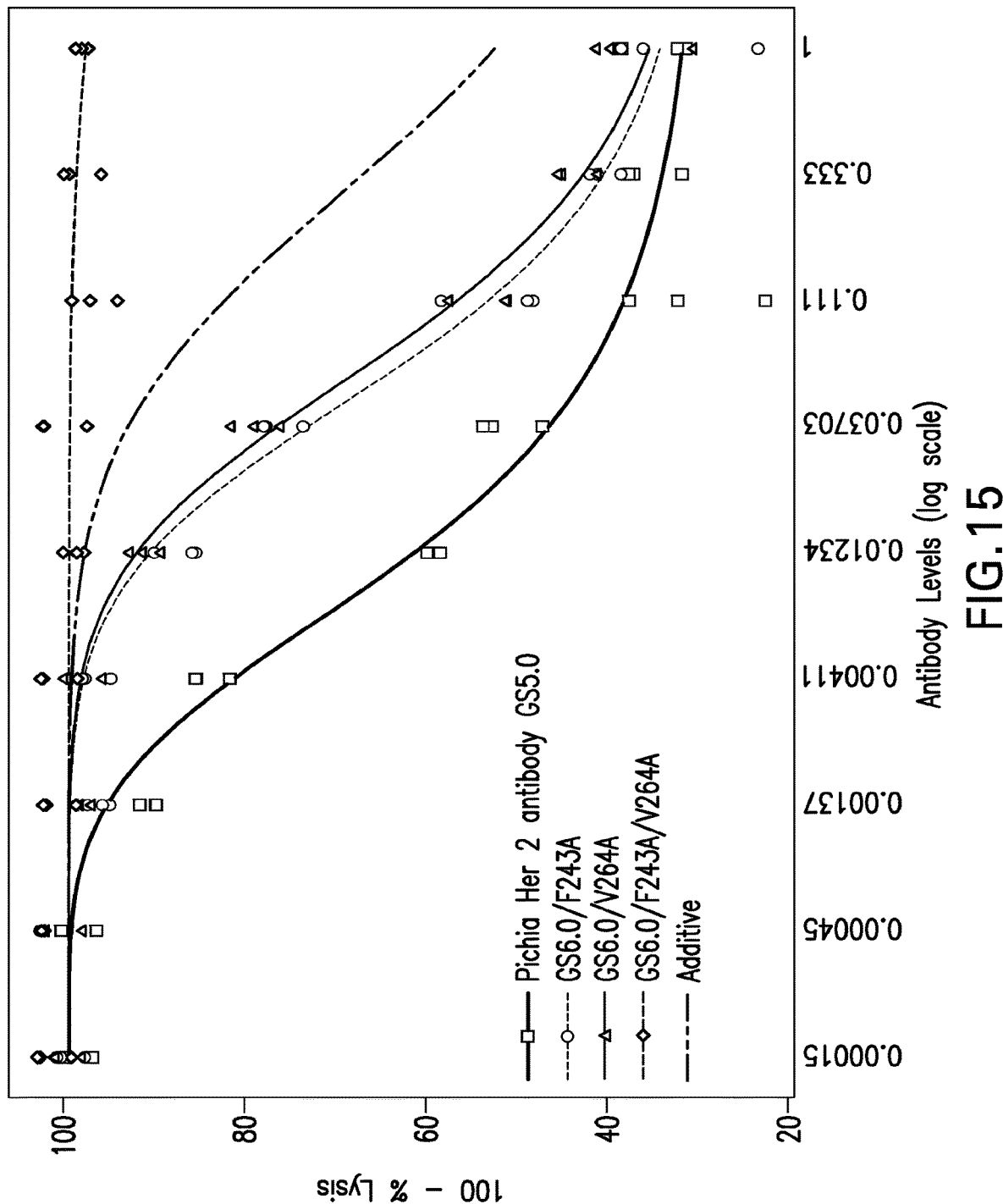

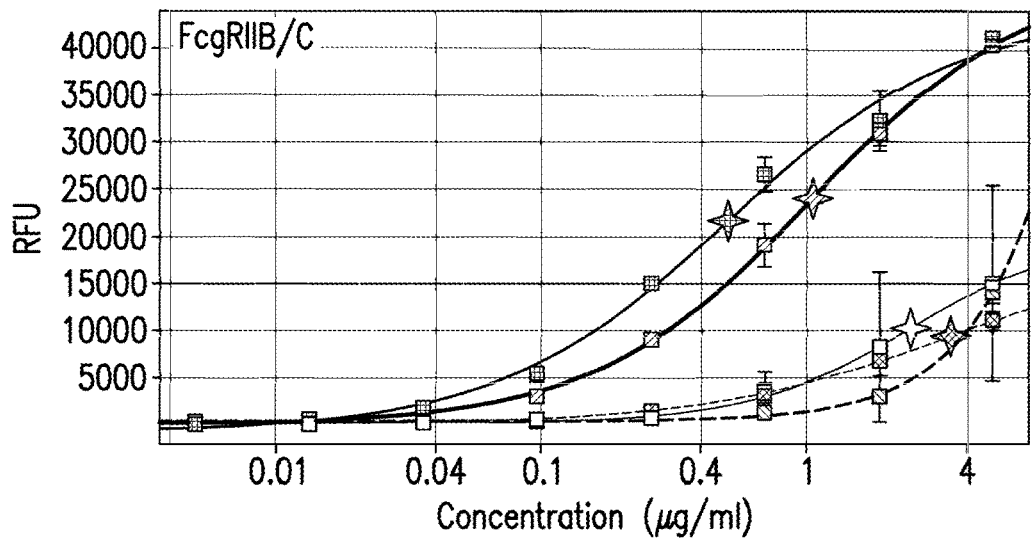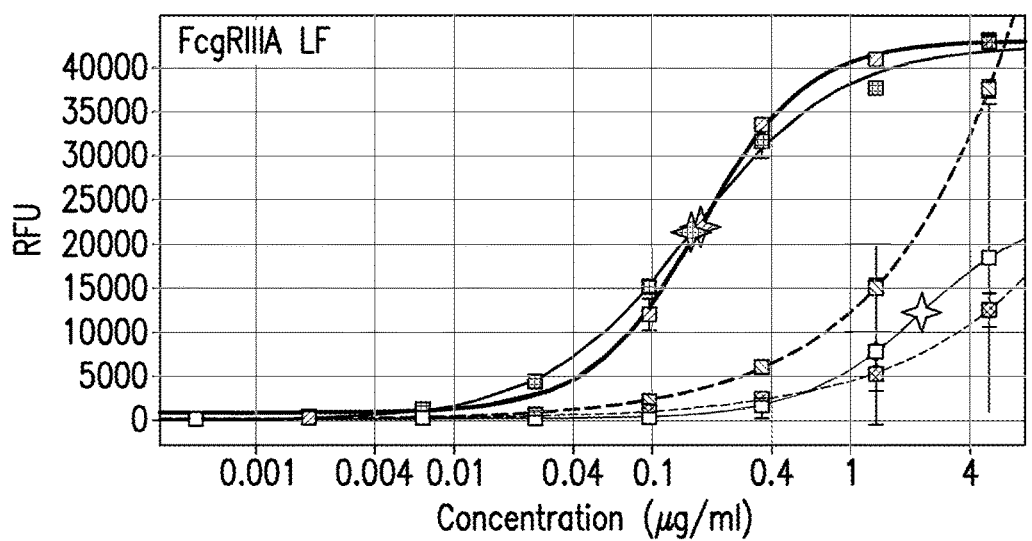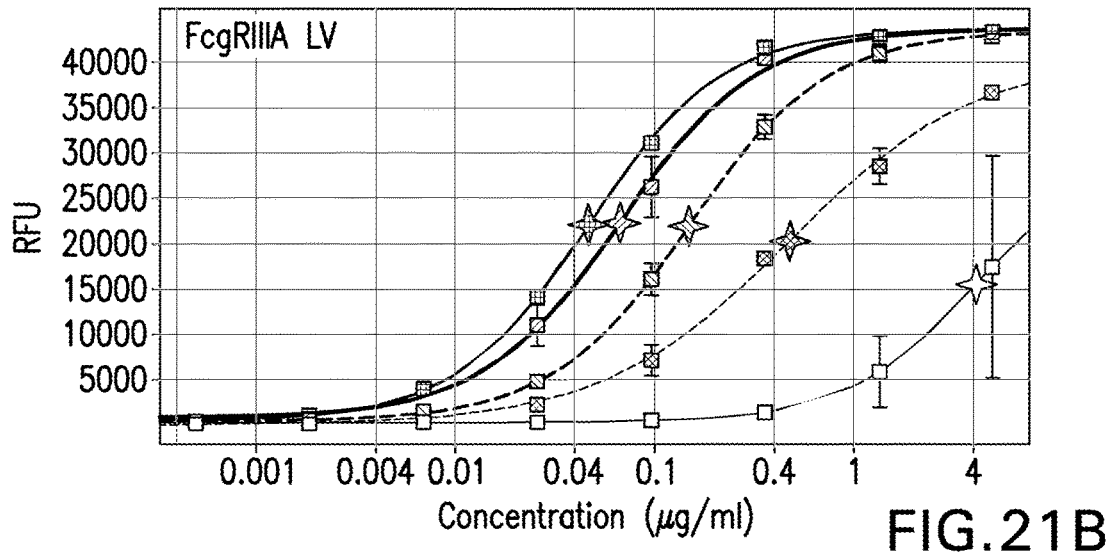
FIG. 21B

Fc-CONTAINING POLYPEPTIDES HAVING IMPROVED PROPERTIES AND COMPRISING MUTATIONS AT POSITIONS 243 AND 264 OF THE Fc-REGION

CROSS REFERENCE TO RELATED APPLICATIONS

This application is a continuation of U.S. application Ser. No. 16/007,590, filed Jun. 13, 2018, which is a continuation of U.S. application Ser. No. 14/931,354, filed Nov. 3, 2015, which is a division of U.S. application Ser. No. 13/699,213, filed Nov. 20, 2012, now pending, which claims the benefit of the National Stage of International Application No. PCT/US11/37826, filed on May 25, 2011, which claims the benefit under 35 U.S.C. 119(e) of U.S. Provisional Application No. 61/348,968, filed May 27, 2010.

REFERENCE TO SEQUENCE LISTING SUBMITTED ELECTRONICALLY

The sequence listing of the present application is submitted electronically via EFS-Web as an ASCII formatted sequence listing with a file name "GFI-MIS-00003-US-CNT-2-SEQLIST.TXT", creation date of Oct. 8, 2020, and a size of 41 KB. This sequence listing submitted via EFS-Web is part of the specification and is herein incorporated by reference in its entirety.

FIELD OF THE INVENTION

The present invention is directed to methods and compositions for the production of glycosylated proteins (glycoproteins) and, specifically, Fc-containing polypeptides which are useful as human or animal therapeutic agents.

BACKGROUND OF THE INVENTION

Monoclonal antibodies often achieve their therapeutic benefit through two binding events. First, the variable domain of the antibody binds a specific protein on a target cell, for example, CD20 on the surface of cancer cells. This is followed by recruitment of effector cells such as natural killer (NK) cells that bind to the constant region (Fc) of the antibody and destroy cells to which the antibody is bound. This process, known as antibody-dependent cell cytotoxicity (ADCC), depends on a specific N-glycosylation event at Asn 297 in the Fc domain of the heavy chain of IgG1s, Rothman et al., Mol. Immunol. 26: 1113-1123 (1989). Antibodies that lack this N-glycosylation structure still bind antigen but cannot mediate ADCC, apparently as a result of reduced affinity of the Fc domain of the antibody for the Fc Receptor FcγRIIIa on the surface of NK cells.

The presence of N-glycosylation not only plays a role in the effector function of an antibody, the particular composition of the N-linked oligosaccharide is also important for its end function. The lack of fucose or the presence of bisecting N-acetyl glucosamine has been positively correlated with the potency of the ADCC, Rothman (1989), Umana et al., Nat. Biotech. 17: 176-180 (1999), Shields et al., J. Biol. Chem. 277: 26733-26740 (2002), and Shinkawa et al., J. Biol. Chem. 278: 3466-3473 (2003). There is also evidence that sialylation in the Fc region is positively correlated with the anti-inflammatory properties of intravenous immunoglobulin (IVIG). See, e.g., Kaneko et al., Science 313: 670-673, 2006; Nimmerjahn and Ravetch., J. Exp. Med. 204: 11-15, 2007.

Given the utility of specific N-glycosylation in the function and potency of antibodies, a method for modifying the composition of N-linked oligosaccharides and modifying the effector function of antibodies would be desirable.

Yeast and other fungal hosts are important production platforms for the generation of recombinant proteins. Yeasts are eukaryotes and, therefore, share common evolutionary processes with higher eukaryotes, including many of the post-translational modifications that occur in the secretory pathway. Recent advances in glycoengineering have resulted in cell lines of the yeast strain *Pichia pastoris* with genetically modified glycosylation pathways that allow them to carry out a sequence of enzymatic reactions, which mimic the process of glycosylation in humans. See, for example, U.S. Pat. Nos. 7,029,872, 7,326,681 and 7,449,308 that describe methods for producing a recombinant glycoprotein in a lower eukaryote host cell that are substantially identical to their human counterparts. Human-like sialylated bi-antennary complex N-linked glycans like those produced in *Pichia pastoris* from the aforesaid methods have demonstrated utility for the production of therapeutic glycoproteins. Thus, a method for further modifying or improving the production of antibodies in yeasts such as *Pichia pastoris* would be desirable.

SUMMARY OF THE INVENTION

The invention relates to an Fc-containing polypeptide comprising mutations at amino acid positions 243 and 264 of the Fc region, wherein the mutations at positions 243 are selected from the group consisting of: F243A, F243G, F243S, F243T, F243V, F243L, F243I, F243D, F243Y, F243E, F243R, F243W and F243K and the mutations at position 264 are selected from the group consisting of: V264A, V264G, V264S, V264T, V264D, V264E, V264K, V264W, V264H, V264P, V264N, V264Q and V264L, wherein the numbering is according to the EU index as in Kabat. In another embodiment, the Fc-containing polypeptide comprises mutations F243A and V264A. In another embodiment, the Fc-containing polypeptide comprises mutations F243Y and V264G. In another embodiment, the Fc-containing polypeptide comprises mutations F243T and V264G. In another embodiment, the Fc-containing polypeptide comprises mutations F243L and V264A. In another embodiment, the Fc-containing polypeptide comprises mutations F243L and V264N. In another embodiment, the Fc-containing polypeptide comprises mutations F243V and V264G. In one embodiment, the Fc-containing polypeptide of the invention is an antibody or an antibody fragment. In one embodiment, the Fc-containing polypeptide of the invention is an antibody fragment comprising SEQ ID NO:18. In another embodiment, the Fc-containing polypeptide of the invention is an antibody fragment comprising SEQ ID NO:19. In another embodiment, the Fc-containing polypeptide of the invention is an antibody fragment consisting of (or consisting essentially of) SEQ ID NO:18 or SEQ ID NO:19.

In one embodiment, the Fc-containing polypeptide is an antibody comprising the heavy chain amino acid sequence of SEQ ID NO:9 or a variant thereof, and the light chain amino acid sequence of SEQ ID NO:2 or a variant thereof. In one embodiment, the Fc-containing polypeptide is an antibody comprising the heavy chain amino acid sequence of SEQ ID NO:9 minus the last lysine (K) residue listed in SEQ ID NO:9.

In one embodiment, the Fc-containing polypeptide is an antibody comprising the heavy chain amino acid sequence of SEQ ID NO:12 or a variant thereof, and the light chain amino acid sequence of SEQ ID NO:11 or a variant thereof.

In one embodiment, the Fc-containing polypeptide is an antibody comprising the heavy chain amino acid sequence of SEQ ID NO:15 or a variant thereof, and the light chain amino acid sequence of SEQ ID NO:14 or a variant thereof.

In some embodiments, the Fc-containing polypeptides of the invention comprise N-glycans comprising sialic acid (including NANA, NGNA, and analogs and derivatives thereof). In one embodiment, the Fc-containing polypeptides of the invention comprise a mixture of α-2,3 and α-2,6 linked sialic acid. In another embodiment, the Fc-containing polypeptides of the invention comprise only α-2,6 linked sialic acid. In one embodiment, the Fc-containing polypeptides of the invention comprise α-2,6 linked sialic acid and comprise no detectable level of α-2,3 linked sialic acid. In one embodiment, the sialic acid is N-acetylneuraminic acid (NANA) or N-glycolylneuraminic acid (NGNA) or a mixture thereof. In another embodiment, the sialic acid is an analog or derivative of NANA or NGNA with acetylation at position 9 on the sialic acid. In one embodiment, the N-glycans on the Fc-containing polypeptides of the invention comprise NANA and no NGNA.

The N-glycans on the Fc-containing polypeptides of the invention can optionally comprise fucose. In one embodiment, the N-glycans on the Fc-containing polypeptides will comprise a mixture of fucosylated and non-fucosylated N-glycans. In another embodiment, the N-glycans on the Fc-containing polypeptides lack fucose.

In one embodiment, the Fc-containing polypeptide of the invention has one or more of the following properties when compared to a parent Fc-containing polypeptide: (i) reduced effector function; (ii) increased anti-inflammatory properties; (iii) increased sialylation; (iv) increased bioavailability (absorption or exposure), and (v) reduced binding to FcγRI, FcγRIIa, FcγRIIb, FcγRIIIa (FcγRIIIa-V158 or FcγRIIIa-F158), and FcγRIIIb. In one embodiment, the Fc-containing polypeptide of the invention has at least a 7, 10, 15, 30, 50, 100, 500 or 1000 fold reduction in effector function compared to a parent Fc-containing polypeptide. In one embodiment, the effector function is ADCC. In another embodiment, the effector function is CDC.

In one embodiment, the Fc-containing polypeptide of the invention has reduced ADCC activity when compared to a parent Fc-containing polypeptide. In one embodiment, the Fc-containing polypeptide has at least a 7, 10, 15, 30, 50 100, 500 or 1000 fold reduction in ADCC activity. In another embodiment, the Fc-containing polypeptide has at least a 100 fold reduction in ADCC activity. In another embodiment, the Fc-containing polypeptide has at least a 500 fold reduction in ADCC activity. In another embodiment, the Fc-containing polypeptide has at least a 1000 fold reduction in ADCC activity.

In another embodiment, the Fc-containing polypeptide of the invention has reduced CDC activity when compared to a parent Fc-containing polypeptide. In one embodiment, the Fc-containing polypeptide has at least 100 fold reduction in CDC activity.

In one embodiment, the Fc-containing polypeptide of the invention binds FcγR1, FcγRIIa, FcγRIIb, FcγRIIIa (FcγRIIIa-V158 or FcγRIIIa-F158), and FcγRIIIb with reduced affinity when compared to a parent Fc-containing polypeptide. In one embodiment, an Fc-containing polypeptide of the invention binds FcγRIIa with a reduced affinity of at least 50 fold when compared to a parent Fc-containing polypeptide. In one embodiment, the Fc-containing polypeptide of the invention binds FcγRIIb with a reduced affinity of at least 20 fold when compared to a parent Fc-containing polypeptide. In one embodiment, the Fc-containing polypeptide of the invention binds FcγRIIIa LF with a reduced affinity of at least 10 fold when compared to a parent Fc-containing polypeptide. In one embodiment, the Fc-containing polypeptide of the invention binds FcγRIIIa LV with a reduced affinity of at least 1, 2 or 10 fold when compared to a parent Fc-containing polypeptide. In one embodiment, the Fc-containing polypeptide of the invention binds FcγRIIb, FcγRIIIa LF and FcγRIIIa LV with a reduced affinity when compared to a parent Fc-containing polypeptide.

In one embodiment, the Fc-containing polypeptide of the invention has increased anti-inflammatory properties compared to a parent Fc-containing polypeptide.

In one embodiment, the Fc-containing polypeptide of the invention has increased bioavailability (absorption or exposure) when injected parenterally compared to a parent Fc-containing polypeptide. In one embodiment, the Fc-containing polypeptide of the invention has increased bioavailability (absorption or exposure) when injected subcutaneously compared to a parent Fc-containing polypeptide.

In a one embodiment, the parent Fc-containing polypeptide comprises a native Fc region. In another embodiment, the parent Fc-containing polypeptide comprises a F243A mutation. In another embodiment, the parent Fc-containing polypeptide comprises a V264A mutation.

The invention also comprises a method for producing an Fc-containing polypeptide in a host cell comprising: (i) providing a host cell that has been genetically engineered to produce an Fc-containing polypeptide, wherein the host cell comprises a nucleic acid encoding mutations at amino acid positions 243 and 264 of the Fc region, wherein the mutations at positions 243 are selected from the group consisting of: F243A, F243G, F243S, F243T, F243V, F243L, F243I, F243D, F243Y, F243E, F243R, F243W and F243K and the mutations at position 264 are selected from the group consisting of: V264A, V264G, V264S, V264T, V264D, V264E, V264K, V264W, V264H, V264P, V264N, V264Q and V264L, wherein the numbering is according to the EU index as in Kabat; (ii) culturing the host cell under conditions which cause expression of the Fc-containing polypeptide; and (iii) isolating the Fc-containing polypeptide from the host cell. In one embodiment, the nucleic acid encodes the mutations F243A and V264A. In another embodiment, the nucleic acid encodes the mutations F243Y and V264G. In another embodiment, the nucleic acid encodes the mutations 243T and V264G. In another embodiment, the nucleic acid encodes the mutations F243L and V264A. In another embodiment, the nucleic acid encodes the mutations F243L and V264N. In another embodiment, the nucleic acid encodes the mutations F243V and V264G. In one embodiment, the Fc-containing polypeptide of the invention is an antibody or an antibody fragment. In one embodiment, the Fc-containing polypeptide is an antibody fragment comprising SEQ ID NO:18. In another embodiment, the Fc-containing polypeptide is an antibody fragment comprising SEQ ID NO:19. In another embodiment, the Fc-containing polypeptide is an antibody fragment consisting of (or consisting essentially of) SEQ ID NO:18 or SEQ ID NO:19.

In one embodiment, the method for producing an Fc-containing polypeptide is carried out in a mammalian cell. In another embodiment, the method for producing an Fc-containing polypeptide is carried out in a plant cell. In another embodiment, the method for producing an Fc-containing polypeptide is carried out in bacteria. In another embodiment, the method for producing an Fc-containing polypeptide is carried out in an insect cell. In another embodiment, the method for producing an Fc-containing polypeptide is carried out in a lower eukaryotic cell. In another embodiment, the method for producing an Fc-containing polypeptide is carried out in a yeast cell. In one embodiment, the method for producing an Fc-containing polypeptide is carried out in *Pichia pastoris*.

In one embodiment, the Fc-containing polypeptide produced by the claimed method comprises N-glycans comprising sialic acid (including NANA, NGNA, and analogs and derivatives thereof). In one embodiment, the Fc-containing polypeptide produced by the claimed method has an N-glycan composition in which at least 40 mole %, 70 mole % or 90 mole % of the N-glycans on the Fc-containing polypeptide are sialylated (have a structure selected from $SA_{(1-4)}Gal_{(1-4)}GlcNAc_{(2-4)}Man_3GlcNAc_2$ or $SAGalGlcNAcMan5GlcNAc_2$). In one embodiment, least 47 mole % of the N-glycans on the antibodies have the structure $SA_2Gal_2GlcNAc_2Man_3GlcNAc_2$. In another embodiment, least 47 mole % of the N-glycans on the antibodies have the structure $NANA_2Gal_2GlcNAc_2Man_3GlcNAc_2$. In another embodiment, least 66 mole % of the N-glycans on the antibodies have the structure $SA_2Gal_2GlcNAc_2Man_3GlcNAc_2$. In another embodiment, least 66 mole % of the N-glycans on the antibodies have the structure $NANA_2Gal_2GlcNAc_2Man_3GlcNAc_2$. In one embodiment, the Fc-containing polypeptides produced by the claimed method comprise a mixture of α-2,3 and α-2,6 linked sialic acid. In another embodiment, the Fc-containing polypeptides comprise only α-2,6 linked sialic acid. In one embodiment, the Fc-containing polypeptides of the invention comprise α-2,6 linked sialic acid and comprise no detectable level of α-2,3 linked sialic acid. In one embodiment, the sialic acid is N-acetylneuraminic acid (NANA) or N-glycolylneuraminic acid (NGNA) or a mixture thereof. In another embodiment, the sialic acid is an analog or derivative of NANA or NGNA with acetylation at position 9 on the sialic acid. In one embodiment, the N-glycans on the Fc-containing polypeptides produced by the claimed method comprise NANA and no NGNA.

The N-glycans on the Fc-containing polypeptides produced by the claimed method can optionally comprise fucose. In one embodiment, the N-glycans on the Fc-containing polypeptides produced by the claimed method comprise a mixture of fucosylated and non-fucosylated N-glycans. In one embodiment, the N-glycans on the Fc-containing polypeptides produced by the claimed method lack fucose.

In one embodiment, the Fc-containing polypeptide produced by the claimed method has an N-glycan composition in which the amount and percentage of total sialylated N-glycans is increased relative to a parent Fc-containing polypeptide.

In some embodiments, the Fc-containing polypeptide produced by the claimed method has one or more of the following properties when compared to a parent Fc-containing polypeptide: (i) reduced effector function; (ii) increased anti-inflammatory properties; (iii) increased sialylation; (iv) increased bioavailability (absorption or exposure), and (v) reduced binding to FcγR1, FcγRIIa, FcγRIIb and FcγRIIIa. In one embodiment, the Fc-containing polypeptide of the invention has at least a 7, 10, 15, 30, 50, 100, 500 or 1000 fold reduction in effector function relative to a parent Fc-containing polypeptide. In one embodiment, the effector function is ADCC. In another embodiment, the effector function is CDC.

In one embodiment, the Fc-containing polypeptide of the invention has reduced ADCC activity when compared to a parent Fc-containing polypeptide. In one embodiment, the Fc-containing polypeptide has at least a 7, 10, 15, 30, 50 100, 500 or 1000 fold reduction in ADCC activity. In another embodiment, the Fc-containing polypeptide has at least a 100 fold reduction in ADCC activity. In another embodiment, the Fc-containing polypeptide has at least a 500 fold reduction in ADCC activity. In another embodiment, the Fc-containing polypeptide has at least a 1000 fold reduction in ADCC activity.

In another embodiment, the Fc-containing polypeptide produced by the claimed method has reduced CDC activity when compared to a parent Fc-containing polypeptide. In one embodiment, the Fc-containing polypeptide has at least 100 fold reduction in CDC activity.

In one embodiment, the Fc-containing polypeptide produced by the claimed method binds FcγRI, FcγRIIa, FcγRIIb, FcγRIIIa (FcγRIIIa-V158 or FcγRIIIa-F158), and FcγRIIIb with reduced affinity when compared to a parent Fc-containing polypeptide. In one embodiment, the Fc-containing polypeptide of the invention binds FcγRIIa with a reduced affinity of at least 50 fold when compared to a parent Fc-containing polypeptide. In one embodiment, the Fc-containing polypeptide of the invention binds FcγRIIb with a reduced affinity of at least 20 fold when compared to a parent Fc-containing polypeptide. In one embodiment, the Fc-containing polypeptide of the invention binds FcγRIIIa LF with a reduced affinity of at least 10 fold when compared to a parent Fc-containing polypeptide. In one embodiment, the Fc-containing polypeptide of the invention binds FcγRIIIa LV with a reduced affinity of at least 1, 2 or 10 fold when compared to a parent Fc-containing polypeptide. In one embodiment, the Fc-containing polypeptide of the invention binds FcγRIIb, FcγRIIIa LF and FcγRIIIa LV with a reduced affinity when compared to a parent Fc-containing polypeptide.

In one embodiment, the Fc-containing polypeptide produced by the claimed method has increased anti-inflammatory properties relative to a parent Fc-containing polypeptide.

In one embodiment, the Fc-containing polypeptide produced by the claimed method has increased bioavailability (absorption or exposure) when injected parenterally compared to a parent Fc-containing polypeptide. In one embodiment, the Fc-containing polypeptide produced by the claimed method has increased bioavailability (absorption or exposure) when injected subcutaneously compared to a parent Fc-containing polypeptide.

In a one embodiment, the parent Fc-containing polypeptide comprises a native Fc region. In another embodiment, the parent Fc-containing polypeptide comprises a F243A mutation. In another embodiment, the parent Fc-containing polypeptide comprises a V264A mutation.

The invention also comprises a method of reducing the effector function of an Fc-containing polypeptide, comprising introducing mutations at positions 243 and 264 of a parent Fc-containing polypeptide, wherein said Fc containing polypeptide has decreased effector function when compared to the parent Fc-containing polypeptide, wherein the numbering is according to the EU index as in Kabat. In a one embodiment, the Fc-containing polypeptide comprises mutations F243A and V264A. In another embodiment, the nucleic acid encodes the mutations F243Y and V264G. In another embodiment, the nucleic acid encodes the mutations 243T and V264G. In another embodiment, the nucleic acid encodes the mutations F243L and V264A. In another embodiment, the nucleic acid encodes the mutations F243L and V264N. In another embodiment, the nucleic acid encodes the mutations F243V and V264G. In one embodiment, the effector function is ADCC. In another embodiment, the effector function is CDC. In one embodiment, the Fc-containing polypeptide of the invention is an antibody or an antibody fragment. In one embodiment, the Fc-containing polypeptide is an antibody fragment comprising SEQ ID NO:18. In another embodiment, the Fc-containing polypeptide is an antibody fragment comprising SEQ ID NO:19. In another embodiment, the Fc-containing polypeptide is an antibody fragment consisting of (or consisting essentially of) SEQ ID NO:18 or SEQ ID NO:19. In a one embodiment, the parent Fc-containing polypeptide comprises a native Fc region. In another embodiment, the parent Fc-containing polypeptide comprises a F243A mutation. In another embodiment, the parent Fc-containing polypeptide comprises a V264A mutation.

The invention also comprises a method of increasing the anti-inflammatory properties of an Fc-containing polypeptide, comprising introducing mutations at positions 243 and 264 of a parent Fc-containing polypeptide, wherein the numbering is according to the EU index as in Kabat, wherein said Fc containing polypeptide has increased anti-inflammatory activity when compared to a parent Fc-containing polypeptide. In a one embodiment, the Fc-containing polypeptide comprises mutations F243A and V264A. In another embodiment, the Fc-containing polypeptide comprises mutations F243Y and V264G. In another embodiment, the Fc-containing polypeptide comprises mutations 243T and V264G. In another embodiment, the Fc-containing polypeptide comprises mutations F243L and V264A. In another embodiment, the Fc-containing polypeptide comprises mutations F243L and V264N. In another embodiment, the Fc-containing polypeptide comprises mutations F243V and V264G. In one embodiment, the Fc-containing polypeptide of the invention is an antibody or an antibody fragment. In one embodiment, the Fc-containing polypeptide is an antibody or antigen binding fragment thereof that binds to an antigen selected from the group consisting of: TNF-α, IL-1, IL-2, IL-4, IL-5, IL-6, IL-8, IL-9, IL-10, IL-12, IL-15, IL-17, IL-18, IL-20, IL-21, IL-22, IL-23, IL-23R, IL-25, IL-27, IL-33, CD2, CD4, CD11A, CD14, CD18, CD19, CD23, CD25, CD40, CD40L, CD20, CD52, CD64, CD80, CD147, CD200, CD200R, TSLP, TSLPR, PD-1, PDL1, CTLA4, VLA-4, VEGF, PCSK9, α4β7-integrin, E-selectin, Fact II, ICAM-3, beta2-integrin, IFNγ, C5, CBL, LCAT, CR3, MDL-1, GITR, ADDL, CGRP, TRKA, IGF1R, RANKL, GTC, or the receptor for any of the above mentioned molecules. In a one embodiment, the Fc-containing polypeptide will bind to TNF-α. In another embodiment, the Fc-containing polypeptide will bind to Her2. In another embodiment, the Fc-containing polypeptide will bind to PCSK9. In one embodiment, the Fc-containing polypeptide of the invention is an antibody fragment comprising SEQ ID NO:18. In another embodiment, the Fc-containing polypeptide of the invention is an antibody fragment comprising SEQ ID NO:19. In another embodiment, the Fc-containing polypeptide of the invention is an antibody fragment consisting of (or consisting essentially of) SEQ ID NO:18 or SEQ ID NO:19. In one embodiment, the parent Fc-containing polypeptide comprises a native Fc region. In another embodiment, the parent Fc-containing polypeptide comprises a F243A mutation. In another embodiment, the parent Fc-containing polypeptide comprises a V264A mutation.

The invention also comprises a method of increasing the anti-inflammatory properties of an Fc-containing polypeptide comprising: selecting a parent Fc-containing polypeptide that is useful in treating inflammation (for example, an antibody or immunoadhesin that binds to an antigen that is involved in inflammation) and introducing mutations at positions 243 and 264 of the Fc-region, wherein the numbering is according to the EU index as in Kabat, wherein the Fc-containing polypeptide has increased anti-inflammatory activity when compared to the parent Fc-containing polypeptide. In a one embodiment, the Fc-containing polypeptide comprises mutations F243A and V264A. In another embodiment, the Fc-containing polypeptide comprises mutations F243Y and V264G. In another embodiment, the Fc-containing polypeptide comprises mutations 243T and V264G. In another embodiment, the Fc-containing polypeptide comprises mutations F243L and V264A. In another embodiment, the Fc-containing polypeptide comprises mutations F243L and V264N. In another embodiment, the Fc-containing polypeptide comprises mutations F243V and V264G. In one embodiment, the Fc-containing polypeptide of the invention is an antibody or an antibody fragment. In one embodiment, the Fc-containing polypeptide is an antibody or antigen binding fragment thereof that binds to an antigen selected from the group consisting of: TNF-α, IL-1, IL-2, IL-4, IL-5, IL-6, IL-8, IL-9, IL-10, IL-12, IL-15, IL-17, IL-18, IL-20, IL-21, IL-22, IL-23, IL-23R, IL-25, IL-27, IL-33, CD2, CD4, CD11A, CD14, CD18, CD19, CD23, CD25, CD40, CD40L, CD20, CD52, CD64, CD80, CD147, CD200, CD200R, TSLP, TSLPR, PD-1, PDL1, CTLA4, VLA-4, VEGF, PCSK9, α4β7-integrin, E-selectin, Fact II, ICAM-3, beta2-integrin, IFNγ, C5, CBL, LCAT, CR3, MDL-1, GITR, ADDL, CGRP, TRKA, IGF1R, RANKL, GTC, or the receptor for any of the above mentioned molecules. In a one embodiment, the Fc-containing polypeptide will bind to TNF-α. In another one embodiment, the Fc-containing polypeptide will bind to Her2. In another one embodiment, the Fc-containing polypeptide will bind to PCSK9. In one embodiment, the Fc-containing polypeptide is an antibody fragment comprising SEQ ID NO:18. In another embodiment, the Fc-containing polypeptide is an antibody fragment comprising SEQ ID NO:19. In another embodiment, the Fc-containing polypeptide is an antibody fragment consisting of (or consisting essentially of) SEQ ID NO:18 or SEQ ID NO:19. In one embodiment, the parent Fc-containing polypeptide comprises a native Fc region. In another embodiment, the parent Fc-containing polypeptide comprises a F243A mutation. In another embodiment, the parent Fc-containing polypeptide comprises a V264A mutation.

The invention also comprises a method of treating an inflammatory condition in a subject in need thereof comprising: administering to the subject a therapeutically effective amount of an Fc-containing polypeptide comprising mutations at positions 243 and 264, wherein the numbering is according to the EU index as in Kabat. In one embodiment, the Fc-containing polypeptide decreases the expression of a gene selected from the group consisting of: IL-1β, IL-6, RANKL, TRAP, ATP6v0d2, MDL-1, DAP12, CD11b, TIMP-1, MMP9, CTSK, PU-1, MCP1, MIP1α, Cxcl1-Groa, CXcl2-Grob, CD18, TNF, FcγRI, FcγRIIb, FcγRIII and FcγRIV. In a one embodiment, the Fc-containing polypeptide comprises mutations F243A and V264A. In another embodiment, the nucleic acid encodes the mutations F243Y and V264G. In another embodiment, the nucleic acid encodes the mutations 243T and V264G. In another embodiment, the nucleic acid encodes the mutations F243L and V264A. In another embodiment, the nucleic acid encodes the mutations F243L and V264N. In another embodiment, the nucleic acid encodes the mutations F243V and V264G. In one embodiment, the Fc-containing polypeptide is administered parenterally. In one embodiment, the Fc-containing polypeptide is administered subcutaneously. In one embodiment, the Fc-containing polypeptide is an antibody or antigen binding fragment thereof. In one embodiment, the Fc-containing polypeptide is an antibody or antigen binding fragment thereof that is useful in treating an inflammatory condition. In one embodiment, the antibody or antigen binding fragment thereof binds to an antigen selected from the group consisting of: TNF-α, IL-1, IL-2, IL-4, IL-5, IL-6, IL-8, IL-9, IL-10, IL-12, IL-15, IL-17, IL-18, IL-20, IL-21, IL-22, IL-23, IL-23R, IL-25, IL-27, IL-33, CD2, CD4, CD11A, CD14, CD18, CD19, CD23, CD25, CD40, CD40L, CD20, CD52, CD64, CD80, CD147, CD200, CD200R, TSLP, TSLPR, PD-1, PDL1, CTLA4, VLA-4, VEGF, PCSK9, α4β7-integrin, E-selectin, Fact II, ICAM-3, beta2-integrin, IFNγ, C5, CBL, LCAT, CR3, MDL-1, GITR, ADDL, CGRP, TRKA, IGF1R, RANKL, GTC, or the receptor for any of the above mentioned molecules. In one embodiment, the Fc-containing polypeptide will bind to TNF-α. In another embodiment, the Fc-containing polypeptide will bind to Her2. In another embodiment, the Fc-containing polypeptide will bind to PCSK9. In one embodiment, the Fc-containing polypeptide is an antibody fragment comprising SEQ ID NO:18. In another embodiment, the Fc-containing polypeptide is an antibody fragment comprising SEQ ID NO:19. In another embodiment, the Fc-containing polypeptide is an antibody fragment consisting of (or consisting essentially of) SEQ ID NO:18 or SEQ ID NO:19

Another invention disclosed herein relates to a pharmaceutical composition comprising an Fc-containing polypeptide, wherein at least 70% of the N-glycans on the Fc-containing polypeptide comprise an oligosaccharide structure selected from the group consisting of $SA_{(1-4)}Gal_{(1-4)}GlcNAc_{(2-4)}Man_3GlcNAc_2$ and $SAGalGlcNAcMan5GlcNAc_2$, wherein the Fc-containing polypeptide comprises mutations at amino acid positions 243 and 264 of the Fc region, wherein the numbering is according to the EU index as in Kabat. In one embodiment, the mutations are F243A and V264A. In another embodiment, the mutations are F243Y and V264G. In another embodiment, the nucleic acid encodes the mutations 243T and V264G. In another embodiment, the mutations are F243L and V264A. In another embodiment, the mutations are F243L and V264N. In another embodiment, the mutations are F243V and V264G. In one embodiment, at least 47 mole % of the N-glycans have the structure $SA_2Gal_2GlcNAc_2Man_3GlcNAc_2$. In another embodiment, at least 47 mole % of the N-glycans have the structure $NANA_2Gal_2GlcNAc_2Man_3GlcNAc_2$. In one embodiment, the sialylated N-glycans comprise a mixture of α-2,3 and α-2,6 linked sialic acid. In another embodiment, the sialylated N-glycans comprise only α-2,6 linked sialic acid. In another embodiment, the sialylated N-glycans comprise α-2,6 linked sialic acid and comprise no detectable level of α-2,3 linked sialic acid. In one embodiment, the sialic acid is N-acetylneuraminic acid (NANA) or N-glycolylneuraminic acid (NGNA) or a mixture thereof. In another embodiment, the sialic acid is an analog or derivative of NANA or NGNA with acetylation at position 9 on the sialic acid. In one embodiment, the N-glycans on the Fc-containing polypeptides comprise NANA and no NGNA. In one embodiment, the Fc-containing polypeptide is an antibody fragment comprising SEQ ID NO:18. In another embodiment, the Fc-containing polypeptide is an antibody fragment comprising SEQ ID NO:19. In another embodiment, the Fc-containing polypeptide is an antibody fragment consisting of (or consisting essentially of) SEQ ID NO:18 or SEQ ID NO:19

Another invention disclosed herein relates to a pharmaceutical composition comprising an Fc-containing polypeptide, wherein at least 70% of the N-glycans on the Fc-containing polypeptide comprise an oligosaccharide structure selected from the group consisting of $SA_{(1-4)}Gal_{(1-4)}GlcNAc_{(2-4)}Man_3GlcNAc_2$ and $SAGalGlcNAcMan5GlcNAc_2$, wherein the sialic acid residues are attached exclusively via an α-2,6 linkage, wherein the N-glycans lack fucose, and wherein the Fc-containing polypeptide comprises mutations at amino acid positions 243 and 264 of the Fc region, wherein the numbering is according to the EU index as in Kabat. In one embodiment, the mutations are F243A and V264A. In another embodiment, the mutations are F243Y and V264G. In another embodiment, the nucleic acid encodes the mutations 243T and V264G. In another embodiment, the mutations are F243L and V264A. In another embodiment, the mutations are F243L and V264N. In another embodiment, the mutations are F243V and V264G. In one embodiment, at least 47 mole % of the N-glycans have the structure $SA_2Gal_2GlcNAc_2Man_3GlcNAc_2$. In another embodiment, at least 47 mole % of the N-glycans have the structure $NANA_2Gal_2GlcNAc_2Man_3GlcNAc_2$. In one embodiment, the sialylated N-glycans comprise a mixture of α-2,3 and α-2,6 linked sialic acid. In another embodiment, the sialylated N-glycans comprise only α-2,6 linked sialic acid. In another embodiment, the sialylated N-glycans comprise α-2,6 linked sialic acid and comprise no detectable level of α-2,3 linked sialic acid. In one embodiment, the sialic acid is N-acetylneuraminic acid (NANA) or N-glycolylneuraminic acid (NGNA) or a mixture thereof. In another embodiment, the sialic acid is an analog or derivative of NANA or NGNA with acetylation at position 9 on the sialic acid. In one embodiment, the N-glycans on the Fc-containing polypeptides comprise NANA and no NGNA. In one embodiment, the Fc-containing polypeptide is an antibody fragment comprising SEQ ID NO:18. In another embodiment, the Fc-containing polypeptide is an antibody fragment comprising SEQ ID NO:19. In another embodiment, the Fc-containing polypeptide is an antibody fragment consisting of (or consisting essentially of) SEQ ID NO:18 or SEQ ID NO:19

The invention also comprises an Fc-containing polypeptide comprising a heavy chain and a light chain, wherein the heavy chain comprises the amino acid sequence of SEQ ID NO:9 or a variant thereof and the light chain comprises the amino acid sequence of SEQ ID NO:2 or a variant thereof, wherein the variant comprises one or more of the following properties when compared to an antibody comprising the heavy chain amino acid sequence of SEQ ID NO:1 and the light chain amino acid sequence of SEQ ID NO:2: reduced effector function, increased anti-inflammatory properties; increased sialylation; increased bioavailability (absorption or exposure) when administered parenterally, and reduced binding to FcγRI, FcγRIIa, FcγRIIb and FcγRIIIa. The invention also comprises an Fc-containing polypeptide comprising a heavy chain and a light chain, wherein the heavy chain comprises the amino acid sequence of SEQ ID NO:12 or a variant thereof and the light chain comprises the amino acid sequence of SEQ ID NO:11 or a variant thereof, wherein the variant comprises one or more of the following properties when compared to an antibody comprising the heavy chain amino acid sequence of SEQ ID NO:10 and the light chain amino acid sequence of SEQ ID NO:11: reduced effector function, increased anti-inflammatory properties, increased sialylation, increased bioavailability (absorption or exposure) when administered parenterally, and reduced binding to FcγR1, FcγRIIa, FcγRIIb, FcγRIIIa and FcγRIIIb. The invention also comprises an Fc-containing polypeptide comprising a heavy chain and a light chain, wherein the heavy chain comprises the amino acid sequence of SEQ ID NO:15 or a variant thereof, and the light chain comprises the amino acid sequence of SEQ ID NO:14 or a variant thereof, wherein the variant comprises one or more of the following properties when compared to an antibody comprising the heavy chain amino acid sequence of SEQ ID NO:13 and the light chain amino acid sequence of SEQ ID NO:14: reduced effector function, increased anti-inflammatory properties, increased sialylation, increased bioavailability (absorption or exposure) when administered parenterally, and reduced binding to FcγR1, FcγRIIa, FcγRIIb, FcγRIIIa and FcγRIIIb. In one embodiment, the variant comprises up to 0, 1, 2, 3, 4, 5, 6, 7, 8, 9, 10 or more conservative or non conservative amino acid substitutions. In one embodiment, the variant comprises at least 75%, 80%, 85%, 90%, 95%, 98% or 99% sequence identity with the claimed sequence The invention also comprises a method of increasing the anti-inflammatory properties of an Fc-containing polypeptide, comprising introducing a mutation at position 243 or a mutation at position 264 of a parent Fc-containing polypeptide, wherein the numbering is according to the EU index as in Kabat, wherein said Fc containing polypeptide has increased anti-inflammatory function when compared to the parent Fc-containing polypeptide. The invention also comprises a method of increasing the anti-inflammatory properties of an Fc-containing polypeptide comprising: selecting a parent Fc-containing polypeptide that is useful in treating inflammation (for example, an antibody or immunoadhesin that binds to an antigen that is involved in inflammation) and introducing a mutation at position 243 or a mutation at position 264 of a parent Fc-containing polypeptide, wherein the numbering is according to the EU index as in Kabat, wherein the Fc-containing polypeptide has increased anti-inflammatory properties when compared to the parent Fc-containing polypeptide. In one embodiment, the Fc-containing polypeptide comprises mutation F243A. In another embodiment, the Fc-containing polypeptide comprises mutation V264A. In one embodiment, the parent Fc-containing polypeptide comprises a native Fc region.

The invention also comprises a method of treating an inflammatory condition in a subject in need thereof comprising: administering to the subject a therapeutically effective amount of an Fc-containing polypeptide a mutation at position 243 or a mutation at position 264 of a parent Fc-containing polypeptide, wherein the numbering is according to the EU index as in Kabat. In one embodiment, the Fc-containing polypeptide is administered parenterally. In one embodiment, the Fc-containing polypeptide is administered subcutaneously. In one embodiment, the Fc-containing polypeptide comprises mutation F243A. In another embodiment, the Fc-containing polypeptide comprises mutation V264A. In one embodiment, the parent Fc-containing polypeptide comprises a native Fc region.

In any of the above embodiment, an increase in anti-inflammatory activity can be detected using any method known in the art. In one embodiment, an increase in anti-inflammatory activity is detected by measuring a decrease in the expression of a gene selected from the group consisting of: IL-1β, IL-6, RANKL, TRAP, ATP6v0d2, MDL-1, DAP12, CD11b, TIMP-1, MMP9, CTSK, PU-1, MCP1, MIP1α, Cxcl1-Groa, CXcl2-Grob, CD18, TNF, FcγRI, FcγRIIb, FcγRIII and FcγRIV.

BRIEF DESCRIPTION OF THE DRAWINGS

FIG. 15 is a graphic representation of the ADCC activity of the anti-Her2 Fc double mutant compared to the assumed additive reference curve of each of the single mutants as described in Example 17.

FIGS. 20-1 and 20-2 are graphic representations of the FcγR binding for the anti-TNFα antibodies described in Example 22. HUMIRA® is the tradename for adalimumab and HERCEPTIN® is the tradename for trastuzumab.

FIGS. 21A-21B are graphic representations of the FcγR binding for the anti-TNFα antibodies described in Example 23. HERCEPTIN® is the tradename for trastuzumab.

DETAILED DESCRIPTION OF THE INVENTION

Definitions

The term "G0" when used herein refers to a complex bi-antennary oligosaccharide without galactose or fucose, $GlcNAc_2Man_3GlcNAc_2$.

The term "G1" when used herein refers to a complex bi-antennary oligosaccharide without fucose and containing one galactosyl residue, $GalGlcNAc_2Man_3GlcNAc_2$.

The term "G2" when used herein refers to a complex bi-antennary oligosaccharide without fucose and containing two galactosyl residues, $Gal_2GlcNAc_2Man_3GlcNAc_2$.

The term "G0F" when used herein refers to a complex bi-antennary oligosaccharide containing a core fucose and without galactose, $GlcNAc_2Man_3GlcNAc_2F$.

The term "G1F" when used herein refers to a complex bi-antennary oligosaccharide containing a core fucose and one galactosyl residue, $GalGlcNAc_2Man_3GlcNAc_2F$.

The term "G2F" when used herein refers to a complex bi-antennary oligosaccharide containing a core fucose and two galactosyl residues, $Gal_2GlcNAc_2Man_3GlcNAc_2F$.

Figure 4:
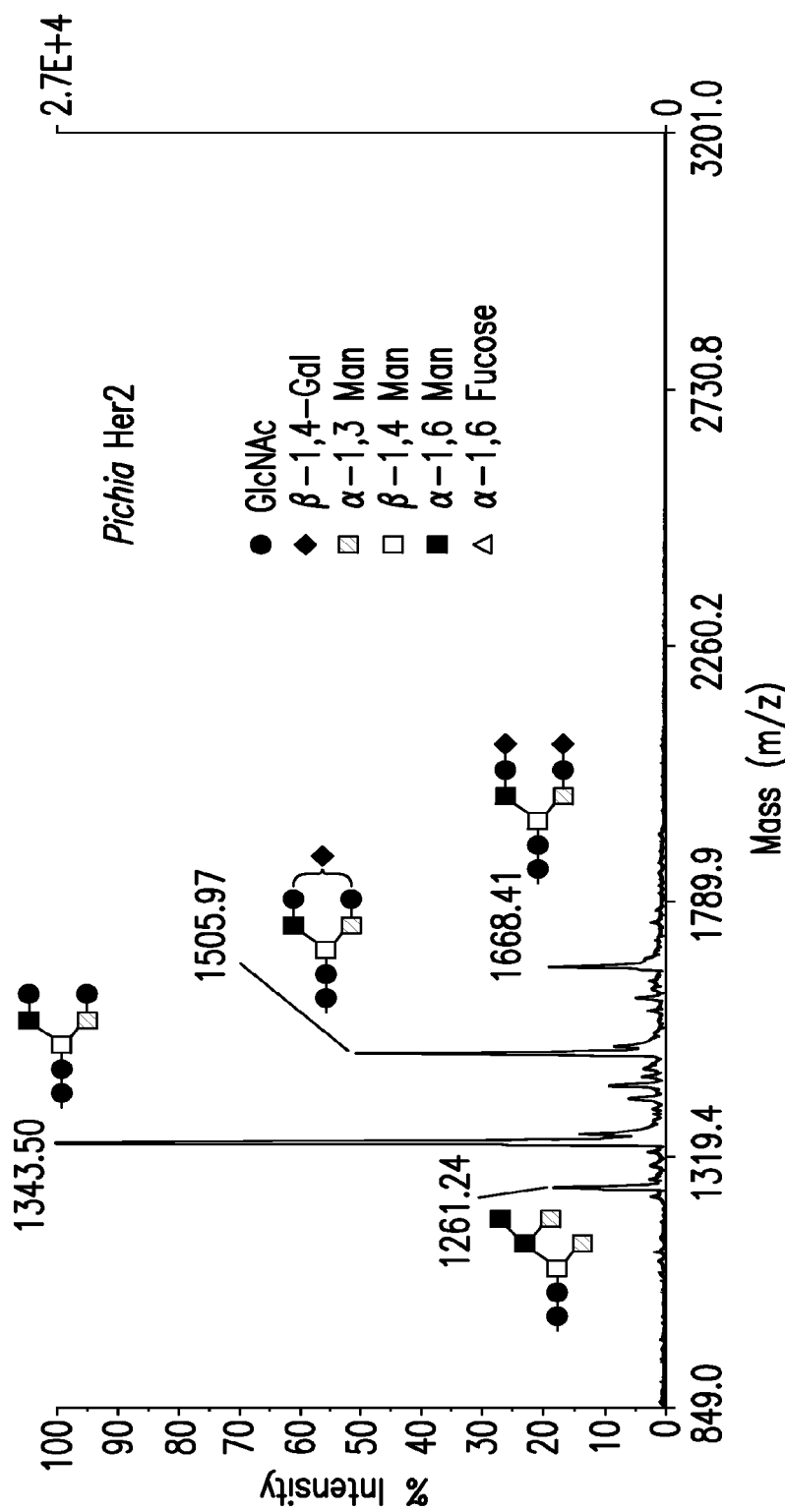
FIG. 4 illustrates a MALDI-TOF MS analysis of N-glycans of a Pichia pastoris Her2 antibody produced in GFI 5.0 strain YDX477. The peaks are $Man_5GlcNAc_2$, 1261.24 (GS2.0), $GlcNAc_2Man_3GlcNAc_2$, 1343.50 (G0) (predominant), $GalGlcNAc_2Man_3GlcNAc_2$, 1505.97 (G1), and $Gal_2GlcNAc_2Man_3GlcNAc_2$, 1668.47 (G2).
Figure 5:
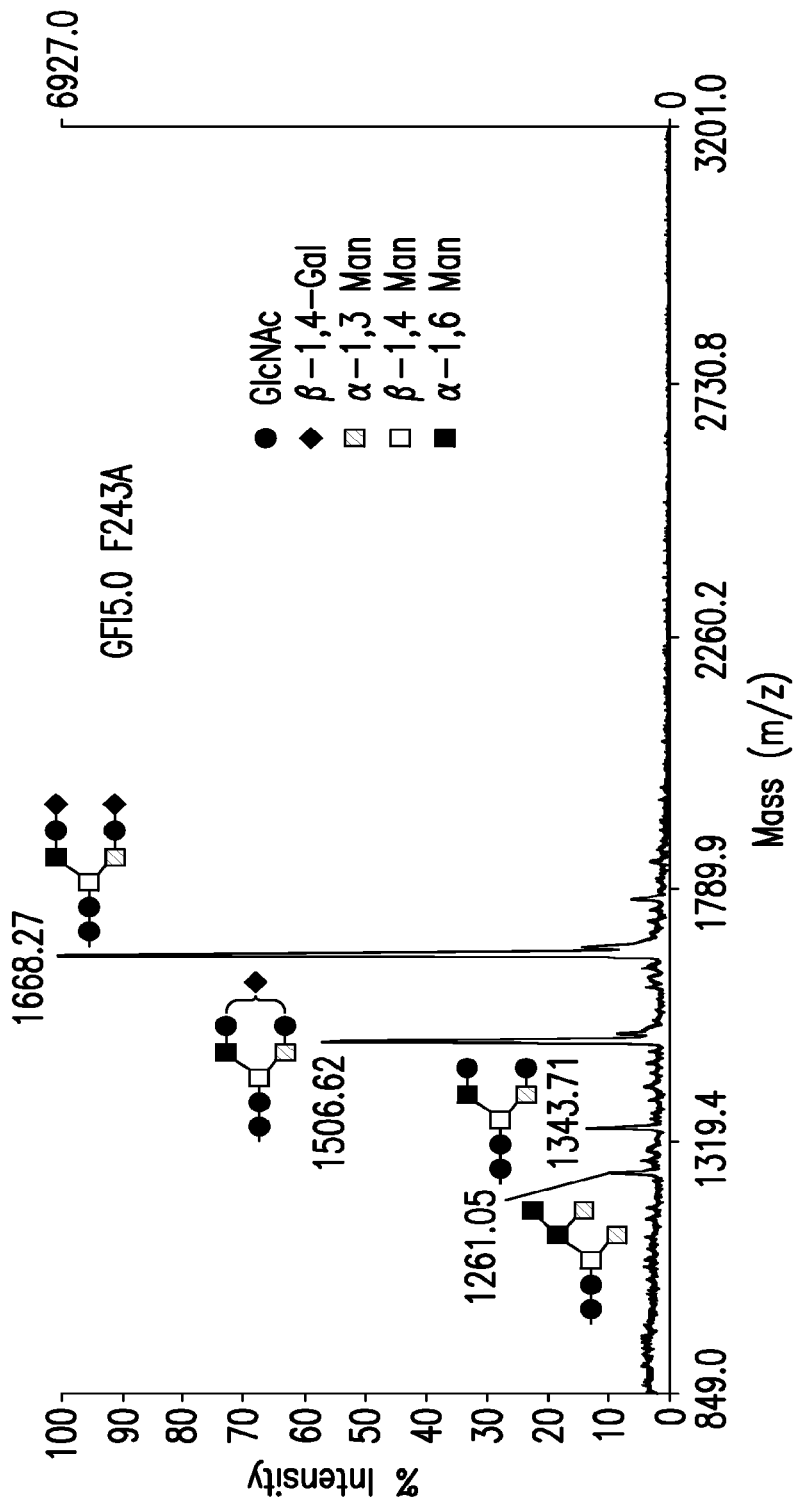
FIG. 5 illustrates a MALDI-TOF MS analysis of N-glycans of a single Fc mutein, F243A, antibody produced in GFI 5.0 strain YDX551. The peaks are $Man_5GlcNAc_2$, 1261.05, $GlcNAc_2Man_3GlcNAc_2$, 1343.71, $GalGlcNAc_2Man_3GlcNAc_2$, 1506.62, and $Gal_2GlcNAc_2Man_3GlcNAc_2$, 1668.97 (predominant).
Figure 6:
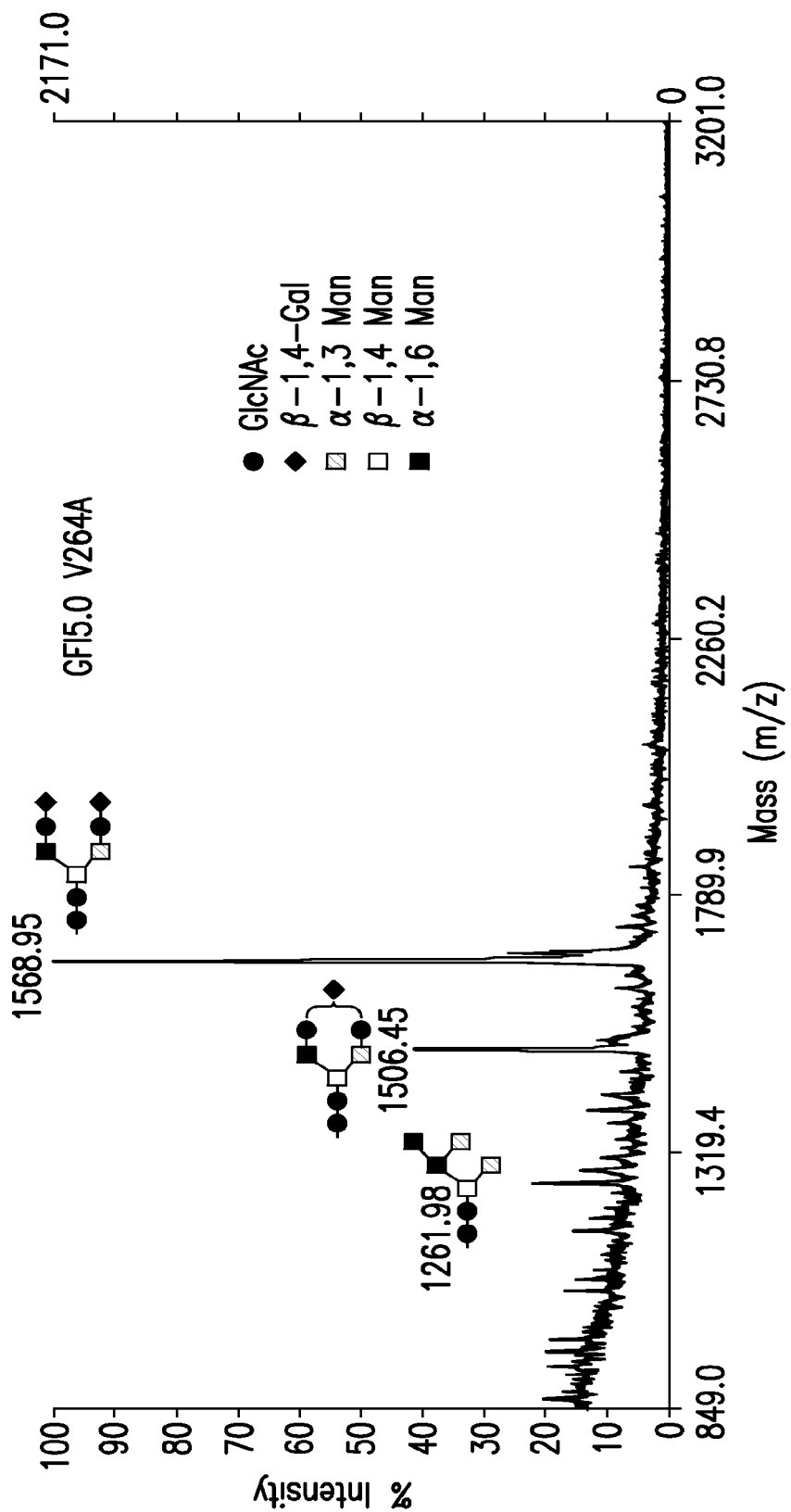
FIG. 6 illustrates a MALDI-TOF MS analysis of N-glycans of a single Fc mutein, V264A, antibody produced in GFI 5.0 strain YDX551. The peaks are $Man_5GlcNAc_2$, 1261.98, $GalGlcNAc_2Man_3GlcNAc_2$, 1505.45, and $Gal_2GlcNAc_2Man_3GlcNAc_2$, 1668.85 (predominant).

The term "Man5" when used herein refers to the oligosaccharide represented by $Man_5GlcNac_2$ and having the structure shown for peak 1261.24 of the MALDI-TOF MS shown in FIG. 4.

The term "GFI 5.0" when used herein refers to glycoengineered Pichia pastoris strains that produce glycoproteins having predominantly $Gal_2GlcNAc_2Man_3GlcNAc_2$ N-glycans.

The term "GFI 6.0" when used herein refers to glycoengineered Pichia pastoris strains that produce glycoproteins having predominantly $NANA_2Gal_2GlcNAc_2Man_3GlcNAc_2$ N-glycans.

The term "GS5.0", when used herein refers to the N-glycosylation structure $Gal_2GlcNAc_2Man_3GlcNAc_2$.

The term "GS5.5", when used herein refers to the N-glycosylation structure $NANAGal_2GlcNAc_2Man_3GlcNAc_2$, which when produced in Pichia pastoris strains to which α 2,6 sialyl transferase has been glycoengineered result in α 2,6-linked sialic acid and which when produced in Pichia pastoris strains to which α 2,3 sialyl transferase has been glycoengineered result in α 2,3-linked sialic acid.

The term "GS6.0", when used herein refers to the N-glycosylation structure $NANA_2Gal_2GlcNAc_2Man_3GlcNAc_2$, which when produced in Pichia pastoris strains to which α 2,6 sialyl transferase has been glycoengineered result in α 2,6-linked sialic acid and which when produced in Pichia pastoris strains to which α 2,3 sialyl transferase has been glycoengineered result in α 2,3-linked sialic acid.

The term "wild type" or "wt" when used herein in connection to a Pichia pastoris strain refers to a native Pichia pastoris strain that has not been subjected to genetic modification to control glycosylation.

The term "antibody", when used herein refers to an immunoglobulin molecule capable of binding to a specific antigen through at least one antigen recognition site located in the variable region of the immunoglobulin molecule. As used herein, the term encompasses not only intact polyclonal or monoclonal antibodies, consisting of four polypeptide chains, i.e. two identical pairs of polypeptide chains, each pair having one "light" chain (LC) (about 25 kDa) and one "heavy" chain (HC) (about 50-70 kDa), but also fragments thereof, such as Fab, Fab', F(ab')2, Fv, single chain (ScFv), mutants thereof, fusion proteins comprising an antibody portion, and any other modified configuration of an immunoglobulin molecule that comprises an antigen recognition site and at least the portion of the $C_H2$ domain of the heavy chain immunoglobulin constant region which comprises an N-linked glycosylation site of the $C_H2$ domain, or a variant thereof. As used herein the term includes an antibody of any class, such as IgG (for example, IgG1, IgG2, IgG3 or IgG4), IgM, IgA, IgD and IgE, respectively.

The term "consensus sequence of $C_H2$" when used herein refers to the amino acid sequence of the $C_H2$ domain of the heavy chain constant region containing an N-linked glycosylation site which was derived from the most common amino acid sequences found in $C_H2$ domains from a variety of antibodies.

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The Fc region of an immunoglobulin comprises two constant domains, CH2 and CH3, and can optionally comprise a hinge region. In one embodiment, the Fc region comprises the amino acid sequence of SEQ ID NO:18. In one embodiment, the Fc region comprises the amino acid sequence of SEQ ID NO:19. In another embodiment, the Fc region comprises the amino acid sequence of SEQ ID NO:18, with the addition of a lysine (K) residue at the 5' end. The Fc region contains a single N-linked glycosylation site in the Ch2 domain that corresponds to the Asn297 site of a full-length heavy chain of an antibody.

The term "Fc-containing polypeptide" refers to a polypeptide, such as an antibody or immunoadhesin, which comprises an Fc region. This term encompasses polypeptides comprising or consisting of (or consisting essentially of) an Fc region. Polypeptides comprising an Fc region can be generated by papain digestion of antibodies or by recombinant DNA technology.

The term "parent antibody", "parent immunoglobulin" or "parent Fc-containing polypeptide" when used herein refers to an antibody or Fc-containing polypeptide which lacks the Fc region mutations disclosed herein. A parent Fc-containing polypeptide may comprise a native sequence Fc region or an Fc region with pre-existing amino acid sequence modifications. A native sequence Fc region comprises an amino acid sequence identical to the amino acid sequence of an Fc region found in nature. Native sequence Fc regions include the native sequence human IgG1 Fc region, the native sequence human IgG2 Fc region, the native sequence human IgG3 Fc region and the native sequence human IgG4 Fc region as well as naturally occurring variants thereof. When used as a comparator, a parent antibody or a parent Fc-containing polypeptide can be expressed in any cell. In one embodiment, the parent antibody or a parent Fc-containing polypeptide is expressed in the same cell as the Fc-containing polypeptide of the invention.

As used herein, the term "immunoadhesin" designates antibody-like molecules which combine the "binding domain" of a heterologous "adhesin" protein (e.g. a receptor, ligand or enzyme) with an immunoglobulin constant domain. Structurally, the immunoadhesins comprise a fusion of the adhesin amino acid sequence with the desired binding specificity which is other than the antigen recognition and binding site (antigen combining site) of an antibody (i.e. is "heterologous") and an immunoglobulin constant domain sequence. The term "ligand binding domain" as used herein refers to any native cell-surface receptor or any region or derivative thereof retaining at least a qualitative ligand binding ability of a corresponding native receptor. In a specific embodiment, the receptor is from a cell-surface polypeptide having an extracellular domain that is homologous to a member of the immunoglobulin supergenefamily. Other receptors, which are not members of the immunoglobulin supergenefamily but are nonetheless specifically covered by this definition, are receptors for cytokines, and in particular receptors with tyrosine kinase activity (receptor tyrosine kinases), members of the hematopoietin and nerve growth factor which predispose the mammal to the disorder in question. In one embodiment, the disorder is cancer. Methods of making immunoadhesins are well known in the art. See, e.g., WO00/42072.

The term "Her2" or "Her2 antibody" when used herein refers to an antibody having an amino acid sequence similar to that for a commercially available Her2 antibody produced in mammalian cells, i.e. CHO cells, known as trastuzumab.

The term "*Pichia* Her2 antibody" or "*Pichia* anti-Her2 antibody" when used herein refers to an antibody having an amino acid sequence similar to that for a commercially available Her2 antibody (trastuzumab) produced in glyco-engineered *Pichia pastoris*.

The term "Fc mutein antibody" when used herein refers to an antibody comprising one of the single Fc muteins or the double Fc mutein described herein.

The term "Fc mutein" when used herein refers to an Fc-containing polypeptide in which one or more point mutations have been made to the Fc region.

The term "Fc mutation" when used herein refers to a mutation made to the Fc region of an Fc-containing polypeptide. Examples of such a mutation include the F243A or V264A mutations described herein.

The term "single Fc mutein" when used herein refers to an Fc-containing polypeptide incorporating a mutation at position 243 or 264 of the Fc region. The term "F243A" refers to a mutation from F (wild-type) to A at position 243 of the Fc region of an Fc-containing polypeptide. The term "V264A" refers to a mutation from V (wild-type) to A at position 264 of the Fc region of an Fc-containing polypeptide. The position 243 and 264 represent the amino acid positions in the CH2 domain of the Fc region of an Fc-containing polypeptide.

The term "double Fc mutein" when used herein refers to an Fc-containing polypeptide comprising mutations at positions 243 and 264 of the Fc region. The term "F243A/V264A" refers to a double Fc mutein comprising the two specified mutations.

Throughout the present specification and claims, the numbering of the residues in an immunoglobulin heavy chain or an Fc-containing polypeptide is that of the EU index as in Kabat et al., Sequences of Proteins of Immunological Interest, 5th Ed. Public Health Service, National Institutes of Health, Bethesda, MD (1991), expressly incorporated herein by reference. The "EU index as in Kabat" refers to the residue numbering of the human IgG1 EU antibody.

The term "effector function" as used herein refers to a biochemical event that results from the interaction of an antibody Fc region with an Fc receptor or ligand. Exemplary "effector functions" include C1q binding; complement dependent cytotoxicity; Fc receptor binding; antibody-dependent cell-mediated cytotoxicity (ADCC); phagocytosis; down regulation of cell surface receptors (e. g. B cell receptor; BCR), etc. Such effector functions can be assessed using various assays known in the art.

The term "glycoengineered *Pichia pastoris*" when used herein refers to a strain of *Pichia pastoris* that has been genetically altered to express human-like N-glycans. For example, the GFI 5.0, GFI 5.5 and GFI 6.0 strains described above.

The terms "N-glycan", "glycoprotein" and "glycoform" when used herein refer to an N-linked oligosaccharide, e.g., one that is attached by an asparagine-N-acetylglucosamine linkage to an asparagine residue of a polypeptide. Predominant sugars found on glycoproteins are glucose, galactose, mannose, fucose, N-acetylgalactosamine (GalNAc), N-acetylglucosamine (GlcNAc) and sialic acid (SA, including NANA, NGNA and derivatives and analogs thereof, including acetylated NANA or acetylated NGNA). In glycoengineered *Pichia pastoris*, sialic acid is exclusively N-acetyl-neuraminic acid (NANA) (Hamilton et al., Science 313 (5792): 1441-1443 (2006)). N-glycans have a common pentasaccharide core of $Man_3GlcNAc_2$, wherein "Man" refers to mannose, "Glc" refers to glucose, "NAc" refers to N-acetyl, and GlcNAc refers to N-acetylglucosamine. N-glycans differ with respect to the number of branches (antennae) comprising peripheral sugars (e.g., GlcNAc, galactose, fucose and sialic acid) that are added to the $Man_3GlcNAc_2$ ("Man3") core structure which is also referred to as the "trimannose core", the "pentasaccharide core" or the "paucimannose core". N-glycans are classified according to their branched constituents (e.g., high mannose, complex or hybrid).

As used herein, the term "sialic acid" or "SA" refers to any member of the sialic acid family, including without limitation: N-acetylneuraminic acid (Neu5Ac or NANA), N-glycolylneuraminic acid (NGNA) and any analog or derivative thereof (including those arising from acetylation at any position on the sialic acid molecule). Sialic acid is a generic name for a group of about 30 naturally occurring acidic carbohydrates that are essential components of a large number of glycoconjugates. Schauer, Biochem. Society Transactions, 11, 270-271 (1983). Sialic acids are usually the terminal residue of the oligosaccharides. N-acetylneuraminic acid (NANA) is the most common sialic acid form and N-glycolylneuraminic acid (NGNA) is the second most common form. Schauer, Glycobiology, 1, 449-452 (1991). NGNA is widespread throughout the animal kingdom and, according to species and tissue, often constitutes a significant proportion of the glycoconjugate-bound sialic acid. Certain species such as chicken and man are exceptional, since they lack NGNA in normal tissues. Corfield, et al., Cell Biology Monographs, 10, 5-50 (1982). In human serum samples, the percentage of sialic acid in the form of NGNA is reported to be 0.01% of the total sialic acid. Schauer, "Sialic Acids as Antigenic Determinants of Complex Carbohydrates", found in The Molecular Immunology of Complex Carbohydrates, (Plenum Press, New York, 1988).

The term "human-like N-glycan", as used herein, refers to the N-linked oligosaccharides which closely resemble the oligosaccharides produced by non-engineered, wild-type human cells. For example, wild-type *Pichia pastoris* and other lower eukaryotic cells typically produce hypermannosylated proteins at N-glycosylation sites. The host cells described herein produce glycoproteins (for example, antibodies) comprising human-like N-glycans that are not hypermannosylated. In some embodiments, the host cells of the present invention are capable of producing human-like N-glycans with hybrid and/or complex N-glycans. The specific type of "human-like" glycans present on a specific glycoprotein produced from a host cell of the invention will depend upon the specific glycoengineering steps that are performed in the host cell.

The term "high mannose" type N-glycan when used herein refers to an N-glycan having five or more mannose residues.

The term "complex" type N-glycan when used herein refers to an N-glycan having at least one GlcNAc attached to the 1,3 mannose arm and at least one GlcNAc attached to the 1,6 mannose arm of a "trimannose" core. Complex N-glycans may also have galactose ("Gal") or N-acetylgalactosamine ("GalNAc") residues that are optionally modified with sialic acid or derivatives (e.g., "NANA" or "NeuAc", where "Neu" refers to neuraminic acid and "Ac" refers to acetyl). Complex N-glycans may also have intrachain substitutions comprising "bisecting" GlcNAc and core fucose ("Fuc"). As an example, when a N-glycan comprises a bisecting GlcNAc on the trimannose core, the structure can be represented as $Man_3GlcNAc_2(GlcNAc)$ or $Man_3GlcNAc_3$. When an N-glycan comprises a core fucose attached to the trimannose core, the structure may be represented as $Man_3GlcNAc_2(Fuc)$. Complex N-glycans may also have multiple antennae on the "trimannose core," often referred to as "multiple antennary glycans."

The term "hybrid" N-glycan when used herein refers to an N-glycan having at least one GlcNAc on the terminal of the 1,3 mannose arm of the trimannose core and zero or more than one mannose on the 1,6 mannose arm of the trimannose core.

When referring to "mole percent" of a glycan present in a preparation of a glycoprotein, the term means the molar percent of a particular glycan present in the pool of N-linked oligosaccharides released when the protein preparation is treated with PNGase and then quantified by a method that is not affected by glycoform composition, (for instance, labeling a PNGase released glycan pool with a fluorescent tag such as 2-aminobenzamide and then separating by high performance liquid chromatography or capillary electrophoresis and then quantifying glycans by fluorescence intensity). For example, 50 mole percent $NANA_2$ $Gal_2GlcNAc_2Man_3GlcNAc_2$ means that 50 percent of the released glycans are $NANA_2$ $Gal_2GlcNAc_2Man_3GlcNAc_2$ and the remaining 50 percent are comprised of other N-linked oligosaccharides.

The term "anti-inflammatory antibody" as used herein, refers to an antibody intended to be used to treat inflammation. The anti-inflammatory properties of an Fc-containing polypeptide can be measured using any method known in the art. In one embodiment, the anti-inflammatory properties of an Fc-containing polypeptide are measured using an animal model, such as the models described in Kaneko et al., Science 313:670-673 (2006), Anthony et al., Science 320: 373-376 (2008), and Examples 20-21 herein. In another embodiment, the anti-inflammatory properties of an Fc-containing polypeptide are measured by determining the level of a biomarker related to inflammation (including without limitation: CRP, pro-inflammatory cytokines such as tumor necrosis factors (TNF-alpha), interferon-gamma, interleukin 6 (IL-6, IL-8, IL-10, chemokines, the coagulation marker D-dimer, sCD14, intestinal fatty acid binding peptide (IFABP), and hyaluronic acid. In one embodiment, the anti-inflammatory properties of an Fc-containing polypeptide is measured by determining the level of C-reactive protein (CRP) using a method known in the art. A decrease in the level of C-reactive protein indicates that the Fc-containing polypeptide has anti-inflammatory properties.

"Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity (see, e.g., Watson et al. (1987) Molecular Biology of the Gene, The Benjamin/Cummings Pub. Co., p. 224 (4th Ed.)). In addition, substitutions of structurally or functionally similar amino acids are less likely to disrupt biological activity. Exemplary conservative substitutions are listed below:

| Original residue | Conservative substitution |
| --- | --- |
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

Glycosylation of immunoglobulin G (IgG) in the Fc region, Asn297 (according to the EU numbering system), has been shown to be a requirement for optimal recognition and activation of effector pathways including antibody dependent cellular cytotoxicity (ADCC) and complement dependent cytotoxicity (CDC), Wright & Morrison, Trends in Biotechnology, 15: 26-31 (1997), Tao & Morrison, J. Immunol., 143(8):2595-2601 (1989). As such, glycosylation engineering in the constant region of IgG has become an area of active research for the development of therapeutic monoclonal antibodies (mAbs). It has been established that the presence of N-linked glycosylation at Asn297 is critical for mAb activity in immune effector function assays including ADCC, Rothman (1989), Lifely et al., Glycobiology 5:813-822 (1995), Umana (1999), Shields (2002), and Shinkawa (2003), and complement dependent cytotoxicity (CDC), Hodoniczky et al., Biotechnol. Prog., 21(6): 1644-1652 (2005), and Jefferis et al., Chem. Immunol., 65: 111-128 (1997). This effect on function has been attributed to the specific conformation adopted by the glycosylated Fc domain, which appears to be lacking when glycosylation is absent. More specifically, IgG which lacks glycosylation in the Fc $C_H2$ domain does not bind to FcγR, including FcγRI, FcγRII, and FcγRIII, Rothman (1989).

Not only does the presence of glycosylation appear to play a role in the effector function of an antibody, the particular composition of the N-linked oligosaccharide is also important. For example, the presence of fucose shows a marked effect on in vitro FcγRIIIa binding and in vitro ADCC, Rothman (1989), and Li et al., Nat. Biotechnol. 24(2): 2100-215 (2006). Recombinant antibodies produced by mammalian cell culture, such as CHO or NSO, contain N-linked oligosaccharides that are predominately fucosylated, Hossler et al., Biotechnology and Bioengineering, 95(5):946-960 (2006), Umana (1999), and Jefferis et al., Biotechnol. Prog. 21:11-16 (2005). Additionally, there is evidence that sialylation in the Fc region may impart anti-inflammatory properties to antibodies. Intravenous immunoglobulin (IVIG) purified over a lectin column to enrich for the sialylated form showed a distinct anti-inflammatory effect limited to the sialylated Fc fragment and was linked to an increase in expression of the inhibitory receptor FcγRIIb, Nimmerjahn and Ravetch., J. Exp. Med. 204:11-15 (2007).

Figure 1:
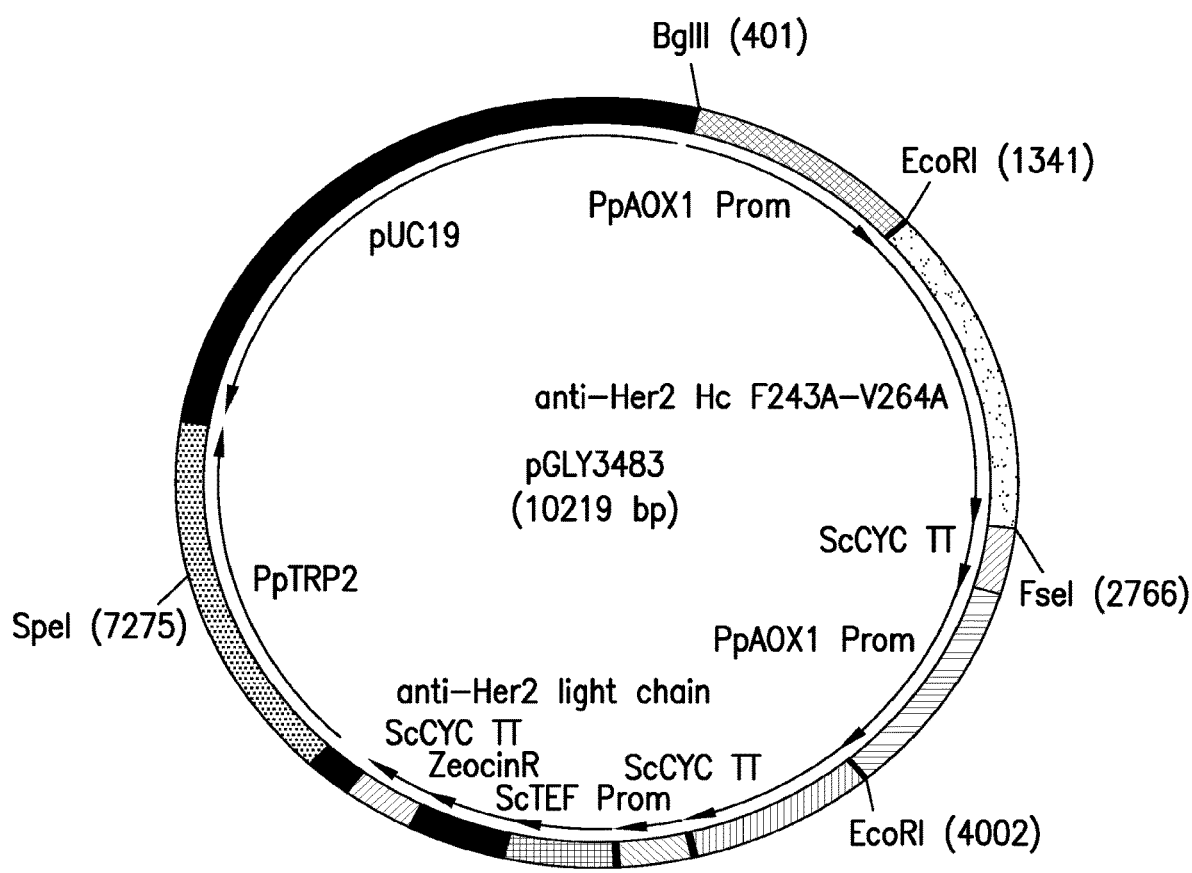
FIG. 1 is a graphic representation of pGLY3483, the F243A and V264A double mutein expression plasmid. Both heavy and light chains were under the control of a methanol inducible promoter, AOX1. The PpTrp2 gene was the locus applied to integrate the entire cassette. With the exception of the mutations on the heavy chain, expression plasmid structure was the same for the wild type (parent), single F243A mutein, single V264A mutein, and the double mutein expression plasmids.

Glycosylation in the Fc region of an antibody derived from mammalian cell lines typically consists of a heterogeneous mix of glycoforms, with the predominant forms typically being comprised of the complex fucosylated glycoforms: G0F, G1F, and, to a lesser extent, G2F. Possible conditions resulting in incomplete galactose transfer to the G0F structure include, but are not limited to, non-optimized galactose transfer machinery, such as β-1,4 galactosyl transferase, and poor UDP-galactose transport into the Golgi apparatus, suboptimal cell culture and protein expression conditions, and steric hindrance by amino acid residues neighboring the oligosaccharide. While each of these conditions may modulate the ultimate degree of terminal galactose, it is thought that subsequent sialic acid transfer to the Fc oligosaccharide is inhibited by the closed pocket configuration of the $C_H2$ domain. See, for example, FIG. 1, Jefferis, R., Nature Biotech., 24 (10): 1230-1231, 2006. Without the correct terminal monosaccharide, specifically galactose, or with insufficient terminal galactosylated forms, there is little possibility of producing a sialylated form, capable of acting as a therapeutic protein, even when produced in the presence of sialyl transferase. Protein engineering and structural analysis of human IgG-Fc glycoforms has shown that glycosylation profiles are affected by Fc conformation, such as the finding that increased levels of galactose and sialic acid on oligosaccharides derived from CHO-produced IgG3 could be achieved when specific amino acids from the Fc pocket were mutated, to an alanine including F241, F243, V264, D265 and R301. Lund et al., J. Immunol. 157(11); 4963-4969 (1996). It was further shown that certain mutations had some effect on cell mediated superoxide generation and complement mediated red cell lysis, which are used as surrogate markers for FcγRI and C1q binding, respectively.

It has been reported that yeast have been genetically engineered to produce host strains capable of secreting glycoproteins with highly uniform glycosylation. Choi et al., PNAS, USA 100(9): 5022-5027 (2003) describes the use of libraries of α 1,2 mannosidase catalytic domains and N-acetylglucosaminyltransferase I catalytic domains in combination with a library of fungal type II membrane protein leader sequences to localize the catalytic domains to the secretory pathway. In this way, strains were isolated that produced in vivo glycoproteins with uniform $Man_5GlcNAc_2$ or $GlcNAcMan_5GlcNAc_2$ N-glycan structures. Hamilton et al., Science 313 (5792): 1441-1443 (2006) described the production of a glycoprotein, erythropoietin, produced in *Pichia pastoris*, as having a glycan composition that consisted predominantly of a bisialylated glycan structure, GS6.0, $NANA_2Gal_2GlcNAc_2Man_3GlcNAc_2$ (90.5%) and monosialylated, GS5.5, $NANAGal_2GlcNAc_2Man_3GlcNAc_2$ (7.9%). However, an antibody produced in a similar strain will have a markedly lower content of sialylated N-glycan due to the relatively low level of terminal galactose substrate in the antibody as seen in FIG. 4. It has also recently been shown that sialylation of a Fc oligosaccharide imparts anti-inflammatory properties on therapeutic intravenous gamma globulin and its Fc fragments, Kaneko et al., Science 313(5787): 670-673 (2006), and that the anti-inflammatory activity is dependent on the α 2,6-linked form, but not the α 2,3 form, of sialic acid, Anthony et al., Science, 320: 373-376 (2008).

Host Organisms and Cell Lines

The Fc-containing polypeptides of this invention can be made in any host organism or cell line. In one embodiment, an Fc-containing polypeptide of the invention is made in a host cell which is capable of producing sialylated N-glycans.

In one embodiment, an Fc-containing polypeptide of the invention is made in a mammalian cell where the cell either endogenously or through genetic or process manipulation produces glycoproteins containing either a mixture of terminal α2-6 and α2-3 sialic acid, or only terminal α2-6 sialic acid. The propagation of mammalian cells in culture (tissue culture) has become a routine procedure. Examples of useful mammalian host cell lines are monkey kidney CV1 line transformed by SV40 (COS-7, ATCC® CRL 1651); human embryonic kidney line (293 or 293 cells subcloned for growth in suspension culture); baby hamster kidney cells (BHK, ATCC® CCL 10); Chinese hamster ovary cells/-DHFR (CHO); mouse sertoli cells (TM4,); monkey kidney cells (CV1 ATCC® CCL 70); African green monkey kidney cells (VERO-76, ATCC® CRL-1587); human cervical carcinoma cells (HELA, ATCC® CCL 2); canine kidney cells (MDCK, ATCC® CCL 34); buffalo rat liver cells (BRL 3A, ATCC® CRL 1442); human lung cells (W138, ATCC® CCL 75); human liver cells (Hep G2, HB 8065); mouse mammary tumor (MMT 060562, ATCC® CCL51); TRI cells; MRC 5 cells; FS4 cells; hybridoma cell lines; NSO; SP2/0; and a human hepatoma line (Hep G2).

In one embodiment, an Fc-containing polypeptide of the invention can be made in a plant cell which is engineered to produce sialylated N-glycans. See, e.g., Cox et al., Nature Biotechnology (2006) 24, 1591-1597 (2006) and Castilho et al., J. Biol. Chem 285(21): 15923-15930 (2010).

In one embodiment, an Fc-containing polypeptide of the invention can be made in an insect cell which is engineered to produce sialylated N-glycans. See, e.g., Harrison and Jarvis, Adv. Virus Res. 68:159-91 (2006).

In one embodiment, an Fc-containing polypeptide of the invention can be made in a bacterial cell which is engineered to produce sialylated N-glycans. See, e.g., Lizak et al., Bioconjugate Chem. 22:488-496 (2011).

In one embodiment, an Fc-containing polypeptide of the invention can be made in a lower eukaryotic host cell or organism. Recent developments allow the production of fully humanized therapeutics in lower eukaryotic host organisms, yeast and filamentous fungi, such as *Pichia pastoris*, Gerngross et al., U.S. Pat. Nos. 7,029,872 and 7,449,308, the disclosures of which are hereby incorporated by reference. See also Jacobs et al., Nature Protocols 4(1): 58-70 (2009). Applicants herein have further developed modified *Pichia pastoris* host organisms and cell lines capable of expressing antibodies comprising two mutations to the amino acids at positions 243 and 264 in the Fc region of the heavy chain. The antibodies having these mutations had increased levels and a more homogeneous composition of the α 2,6-linked sialylated N-glycans when compared to a parent antibody. Applicants have also surprisingly found that mutations at amino acids at positions 243 and 264 in the Fc region of the heavy chain resulted in an antibody which had decreased binding to all Fcγ receptors and decreased C1q binding, the former of which is a surrogate for ADCC, which was independent of the increased levels of the α 2,6-linked sialic acid. Thus, based on the increased level and more homogeneity of the terminal α 2,6-linked sialic acid N-glycan, those of ordinary skill in the art would recognize and appreciate that the materials and methods described herein can be used to produce recombinant glycosylated antibodies in lower eukaryotic cells, such as yeast and filamentous fungi, and, in particular, *Pichia pastoris*, that have enhanced anti-inflammatory properties when compared to a parent antibody.

Due to the decreased FcγR and C1q binding, the materials and methods described herein can be used to produce recombinant glycosylated antibodies with decreased effector function when compared to a parent antibody. Antibodies so produced in *Pichia pastoris* by the methods of the invention were produced at high yield, with decreased effector function, and had a predominant species of glycoprotein having a terminal α 2,6-linked sialic acid residue as compared to antibodies produced in glycoengineered *Pichia pastoris* cells lacking the specific Fc mutations or in *Pichia pastoris* host cells retaining their endogenous glycosylation machinery.

In one embodiment, an Fc-containing polypeptide of the invention is made in a host cell, more preferably a yeast or filamentous fungal host cell, that has been engineered to produce glycoproteins having a predominant N-glycan comprising a terminal sialic acid. In one embodiment of the invention, the predominant N-glycan is the α 2,6 linked form of $SA_2Gal_2GlcNAc_2Man_3GlcNAc_2$, produced in strains glycoengineered with α 2,6 sialyl transferase which do not produce any α 2,3 linked sialic acid. In other embodiments, the strain will be engineered to express an α 2,3 sialyl transferase alone or in combination with an α 2,6, sialyl transferase, resulting in α 2,3 linked or a combination of α 2,6 and α 2,3 linked sialic acid as the predominant N-glycans.

The cell lines to be used to make the Fc-containing polypeptides of the invention can be any cell line, in particular cell lines with the capability of producing one or more sialylated glycoproteins. Those of ordinary skill in the art would recognize and appreciate that the materials and methods described herein are not limited to the specific strain of *Pichia pastoris* provided as an example herein, but could include any *Pichia pastoris* strain or other yeast or filamentous fungal strains in which N-glycans with one or more terminal galactose, such as $Gal_2GlcNAc_2Man_3$, are produced. The terminal galactose acts as a substrate for the production of α 2,6-linked sialic acid, resulting in the N-glycan structure $NANA_2Gal_2GlcNAc_2Man_3GlcNAc_2$. Examples of suitable strains are described in U.S. Pat. No. 7,029,872, US 2006-0286637 and Hamilton et al., Science 313 (5792): 1441-1443 (2006), the descriptions of which are incorporated herein as if set forth at length.

In general, lower eukaryotes such as yeast are used for expression of the proteins, particularly glycoproteins because they can be economically cultured, give high yields, and when appropriately modified are capable of suitable glycosylation. Yeast particularly offers established genetics allowing for rapid transformations, tested protein localization strategies and facile gene knock-out techniques. Suitable vectors have expression control sequences, such as promoters, including 3-phosphoglycerate kinase or other glycolytic enzymes, and an origin of replication, termination sequences and the like as desired.

While the invention has been demonstrated herein using the methylotrophic yeast *Pichia pastoris*, other useful lower eukaryote host cells include *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pljperi, Pichia stiptis, Pichia methanolica, Pichia sp., Saccharomyces cerevisiae, Saccharomyces sp., Hansenula polymorpha, Kluyveromyces sp., Kluyveromyces lactis, Candida albicans, Aspergillus nidulans, Aspergillus niger, Aspergillus oryzae, Trichoderma reesei, Chrysosporiumi lucknowense, Fusarium sp., Fusarium gramineum, Fusarium venenatum* and *Neuro-*

*spora crassa*. Various yeasts, such as *K. lactis, Pichia pastoris, Pichia methanolica,* and *Hansenula polymorpha* are particularly suitable for cell culture because they are able to grow to high cell densities and secrete large quantities of recombinant protein. Likewise, filamentous fungi, such as *Aspergillus niger, Fusarium* sp, *Neurospora crassa* and others can be used to produce glycoproteins of the invention at an industrial scale.

Lower eukaryotes, particularly yeast and filamentous fungi, can be genetically modified so that they express glycoproteins in which the glycosylation pattern is human-like or humanized. As indicated above, the term "human-like N-glycan", as used herein refers, to the N-linked oligosaccharides which closely resemble the oligosaccharides produced by non-engineered, wild-type human cells. In preferred embodiments of the present invention, the host cells of the present invention are capable of producing human-like glycoproteins with hybrid and/or complex N-glycans; i.e., "human-like N-glycosylation." The specific "human-like" glycans predominantly present on glycoproteins produced from the host cells of the invention will depend upon the specific engineering steps that are performed. In this manner, glycoprotein compositions can be produced in which a specific desired glycoform is predominant in the composition. Such can be achieved by eliminating selected endogenous glycosylation enzymes and/or genetically engineering the host cells and/or supplying exogenous enzymes to mimic all or part of the mammalian glycosylation pathway as described in U.S. Pat. No. 7,449,308. If desired, additional genetic engineering of the glycosylation can be performed, such that the glycoprotein can be produced with or without core fucosylation. Use of lower eukaryotic host cells is further advantageous in that these cells are able to produce highly homogenous compositions of glycoprotein, such that the predominant glycoform of the glycoprotein may be present as greater than thirty mole percent of the glycoprotein in the composition. In particular aspects, the predominant glycoform may be present in greater than forty mole percent, fifty mole percent, sixty mole percent, seventy mole percent and, most preferably, greater than eighty mole percent of the glycoprotein present in the composition.

Lower eukaryotes, particularly yeast, can be genetically modified so that they express glycoproteins in which the glycosylation pattern is human-like or humanized. Such can be achieved by eliminating selected endogenous glycosylation enzymes and/or supplying exogenous enzymes as described by Gerngross et al., U.S. Pat. No. 7,449,308. For example, a host cell can be selected or engineered to be depleted in $\alpha 1,6$-mannosyl transferase activities, which would otherwise add mannose residues onto the N-glycan on a glycoprotein.

In one embodiment, the host cell further includes an $\alpha 1,2$-mannosidase catalytic domain fused to a cellular targeting signal peptide not normally associated with the catalytic domain and selected to target the $\alpha 1,2$-mannosidase activity to the ER or Golgi apparatus of the host cell. Passage of a recombinant glycoprotein through the ER or Golgi apparatus of the host cell produces a recombinant glycoprotein comprising a $Man_5GlcNAc_2$ glycoform, for example, a recombinant glycoprotein composition comprising predominantly a $Man_5GlcNAc_2$ glycoform. For example, U.S. Pat. Nos. 7,029,872 and 7,449,308 and U.S. Published Patent Application No. 2005/0170452 disclose lower eukaryote host cells capable of producing a glycoprotein comprising a $Man_5GlcNAc_2$ glycoform.

In a further embodiment, the immediately preceding host cell further includes a GlcNAc transferase I (GnT I) catalytic domain fused to a cellular targeting signal peptide not normally associated with the catalytic domain and selected to target GlcNAc transferase I activity to the ER or Golgi apparatus of the host cell. Passage of the recombinant glycoprotein through the ER or Golgi apparatus of the host cell produces a recombinant glycoprotein comprising a $GlcNAcMan_5GlcNAc_2$ glycoform, for example a recombinant glycoprotein composition comprising predominantly a $GlcNAcMan_5GlcNAc_2$ glycoform. U.S. Pat. Nos. 7,029,872 and 7,449,308 and U.S. Published Patent Application No. 2005/0170452 disclose lower eukaryote host cells capable of producing a glycoprotein comprising a $GlcNAcMan_5GlcNAc_2$ glycoform. The glycoprotein produced in the above cells can be treated in vitro with a hexosaminidase to produce a recombinant glycoprotein comprising a $Man_5GlcNAc_2$ glycoform.

In a further embodiment, the immediately preceding host cell further includes a mannosidase II catalytic domain fused to a cellular targeting signal peptide not normally associated with the catalytic domain and selected to target mannosidase II activity to the ER or Golgi apparatus of the host cell. Passage of the recombinant glycoprotein through the ER or Golgi apparatus of the host cell produces a recombinant glycoprotein comprising a $GlcNAcMan_3GlcNAc_2$ glycoform, for example a recombinant glycoprotein composition comprising predominantly a $GlcNAcMan_3GlcNAc_2$ glycoform. U.S. Pat. No. 7,029,872 and U.S. Published Patent Application No. 2004/0230042 discloses lower eukaryote host cells that express mannosidase II enzymes and are capable of producing glycoproteins having predominantly a $GlcNAcMan_3GlcNAc_2$ glycoform. The glycoprotein produced in the above cells can be treated in vitro with a hexosaminidase to produce a recombinant glycoprotein comprising a $Man_3GlcNAc_2$ glycoform.

In a further embodiment, the immediately preceding host cell further includes GlcNAc transferase II (GnT II) catalytic domain fused to a cellular targeting signal peptide not normally associated with the catalytic domain and selected to target GlcNAc transferase II activity to the ER or Golgi apparatus of the host cell. Passage of the recombinant glycoprotein through the ER or Golgi apparatus of the host cell produces a recombinant glycoprotein comprising a $GlcNAc_2Man_3GlcNAc_2$ glycoform, for example a recombinant glycoprotein composition comprising predominantly a $GlcNAc_2Man_3GlcNAc_2$ glycoform. U.S. Pat. Nos. 7,029,872 and 7,449,308 and U.S. Published Patent Application No. 2005/0170452 disclose lower eukaryote host cells capable of producing a glycoprotein comprising a $GlcNAc_2Man_3GlcNAc_2$ glycoform. The glycoprotein produced in the above cells can be treated in vitro with a hexosaminidase to produce a recombinant glycoprotein comprising a $Man_3GlcNAc_2$ glycoform.

In a further embodiment, the immediately preceding host cell further includes a galactosyltransferase catalytic domain fused to a cellular targeting signal peptide not normally associated with the catalytic domain and selected to target galactosyltransferase activity to the ER or Golgi apparatus of the host cell. Passage of the recombinant glycoprotein through the ER or Golgi apparatus of the host cell produces a recombinant glycoprotein comprising a $GalGlcNAc_2Man_3GlcNAc_2$ or $Gal_2GlcNAc_2Man_3GlcNAc_2$ glycoform, or mixture thereof for example a recombinant glycoprotein composition comprising predominantly a $GalGlcNAc_2Man_3GlcNAc_2$ glycoform or $Gal_2GlcNAc_2Man_3GlcNAc_2$ glycoform or mixture thereof. U.S. Pat. No. 7,029,872 and U.S. Published Patent Application No. 2006/0040353 discloses lower eukaryote host cells capable of producing a glycoprotein comprising a $Gal_2GlcNAc_2$ $Man_3GlcNAc_2$ glycoform. The glycoprotein produced in the above cells can be treated in vitro with a galactosidase to produce a recombinant glycoprotein comprising a $GlcNAc_2Man_3$ $GlcNAc_2$ glycoform, for example a recombinant glycoprotein composition comprising predominantly a $GlcNAc_2Man_3GlcNAc_2$ glycoform.

In a further embodiment, the immediately preceding host cell further includes a sialyltransferase catalytic domain fused to a cellular targeting signal peptide not normally associated with the catalytic domain and selected to target sialyltransferase activity to the ER or Golgi apparatus of the host cell. In a preferred embodiment, the sialyltransferase is an alpha2,6-sialyltransferase. Passage of the recombinant glycoprotein through the ER or Golgi apparatus of the host cell produces a recombinant glycoprotein comprising predominantly a $NANA_2Gal_2GlcNAc_2Man_3GlcNAc_2$ glycoform or $NANAGal_2GlcNAc_2Man_3GlcNAc_2$ glycoform or mixture thereof. For lower eukaryote host cells such as yeast and filamentous fungi, it is useful that the host cell further include a means for providing CMP-sialic acid for transfer to the N-glycan. U.S. Published Patent Application No. 2005/0260729 discloses a method for genetically engineering lower eukaryotes to have a CMP-sialic acid synthesis pathway and U.S. Published Patent Application No. 2006/0286637 discloses a method for genetically engineering lower eukaryotes to produce sialylated glycoproteins. To enhance the amount of sialylation, it can be advantageous to construct the host cell to include two or more copies of the CMP-sialic acid synthesis pathway or two or more copies of the sialylatransferase. The glycoprotein produced in the above cells can be treated in vitro with a neuraminidase to produce a recombinant glycoprotein comprising predominantly a $Gal_2GlcNAc_2Man_3GlcNAc_2$ glycoform or $GalGlcNAc_2Man_3GlcNAc_2$ glycoform or mixture thereof.

Any one of the preceding host cells can further include one or more GlcNAc transferase selected from the group consisting of GnT III, GnT IV, GnT V, GnT VI, and GnT IX to produce glycoproteins having bisected (GnT III) and/or multiantennary (GnT IV, V, VI, and IX) N-glycan structures such as disclosed in U.S. Published Patent Application Nos. 2005/0208617 and 2007/0037248. Further, the proceeding host cells can produce recombinant glycoproteins (for example, antibodies) comprising SA(1-4)Gal(1-4)GlcNAc (2-4) $Man_3GlcNAc_2$, including antibodies comprising NANA (1-4)Gal(1-4)GlcNAc(2-4) $Man_3GlcNAc_2$, NGNA (1-4)Gal(1-4)GlcNAc(2-4)$Man_3GlcNAc_2$ or a combination of NANA (1-4)Gal(1-4)GlcNAc(2-4) $Man_3GlcNAc_2$ and NGNA(1-4)Gal(1-4)GlcNAc(2-4) $Man_3GlcNAc_2$. In one embodiment, the recombinant glycoprotein will comprise N-glycans comprising a structure selected from the group consisting of SA(1-4)Gal(1-4)GlcNAc(2-4) $Man_3GlcNAc_2$ and devoid of any α2-3 linked SA.

In further embodiments, the host cell that produces glycoproteins that have predominantly $GlcNAcMan_5GlcNAc_2$ N-glycans further includes a galactosyltransferase catalytic domain fused to a cellular targeting signal peptide not normally associated with the catalytic domain and selected to target the galactosyltransferase activity to the ER or Golgi apparatus of the host cell. Passage of the recombinant glycoprotein through the ER or Golgi apparatus of the host cell produces a recombinant glycoprotein comprising predominantly the $GalGlcNAcMan_5GlcNAc_2$ glycoform.

In a further embodiment, the immediately preceding host cell that produced glycoproteins that have predominantly the $GalGlcNAcMan_5GlcNAc_2$ N-glycans further includes a sialyltransferase catalytic domain fused to a cellular targeting signal peptide not normally associated with the catalytic domain and selected to target sialyltransferase activity to the ER or Golgi apparatus of the host cell. Passage of the recombinant glycoprotein through the ER or Golgi apparatus of the host cell produces a recombinant glycoprotein comprising a $SAGalGlcNAcMan5GlcNAc_2$ glycoform (for example $NANAGalGlcNAcMan_5GlcNAc_2$ or $NGNAGalGlcNAcMan_5GlcNAc_2$ or a mixture thereof).

Any of the preceding host cells can further include one or more sugar transporters such as UDP-GlcNAc transporters (for example, *Kluyveromyces lactis* and *Mus musculus* UDP-GlcNAc transporters), UDP-galactose transporters (for example, *Drosophila melanogaster* UDP-galactose transporter), and CMP-sialic acid transporter (for example, human sialic acid transporter). Because lower eukaryote host cells such as yeast and filamentous fungi lack the above transporters, it is preferable that lower eukaryote host cells such as yeast and filamentous fungi be genetically engineered to include the above transporters.

Further, any of the preceding host cells can be further manipulated to increase N-glycan occupancy. See e, g., Gaulitzek et al., Biotechnol. Bioengin. 103:1164-1175 (2009); Jones et al., Biochim. Biospyhs. Acta 1726:121-137 (2005); WO2006/107990. In one embodiment, any of the preceding host cells can be further engineered to comprise at least one nucleic acid molecule encoding a heterologous single-subunit oligosaccharyltransferase (for example, *Leishmania* sp. STT3A protein, STT3B protein, STT3C protein, STT3D protein or combinations thereof) and a nucleic acid molecule encoding the heterologous glycoprotein, and wherein the host cell expresses the endogenous host cell genes encoding the proteins comprising the endogenous OTase complex. In one embodiment, any of the preceding host cells can be further engineered to comprise at least one nucleic acid molecule encoding a *Leishmania* sp. STT3D protein and a nucleic acid molecule encoding the heterologous glycoprotein, and wherein the host cell expresses the endogenous host cell genes encoding the proteins comprising the endogenous OTase complex.

Host cells further include lower eukaryote cells (e.g., yeast such as *Pichia pastoris*) that are genetically engineered to produce glycoproteins that do not have α-mannosidase-resistant N-glycans. This can be achieved by deleting or disrupting one or more of the β-mannosyltransferase genes (e.g., BMT1, BMT2, BMT3, and BMT4) (See, U.S. Published Patent Application No. 2006/0211085) and glycoproteins having phosphomannose residues by deleting or disrupting one or both of the phosphomannosyl transferase genes PNO1 and MNN4B (See for example, U.S. Pat. Nos. 7,198,921 and 7,259,007), which in further aspects can also include deleting or disrupting the MNN4A gene. Disruption includes disrupting the open reading frame encoding the particular enzymes or disrupting expression of the open reading frame or abrogating translation of RNAs encoding one or more of the β-mannosyltransferases and/or phosphomannosyltransferases using interfering RNA, antisense RNA, or the like. Further, cells can produce glycoproteins with α-mannosidase-resistant N-glycans through the addition of chemical hinhibios or through modification of the cell culture condition. These host cells can be further modified as described above to produce particular N-glycan structures.

Host cells further include lower eukaryote cells (e.g., yeast such as *Pichia pastoris*) that are genetically modified to control O-glycosylation of the glycoprotein by deleting or disrupting one or more of the protein O-mannosyltransferase (Dol-P-Man:Protein (Ser/Thr) Mannosyl Transferase genes)

(PMTs) (See U.S. Pat. No. 5,714,377) or grown in the presence of Pmtp inhibitors and/or an α-mannosidase as disclosed in Published International Application No. WO 2007/061631, or both. Disruption includes disrupting the open reading frame encoding the Pmtp or disrupting expression of the open reading frame or abrogating translation of RNAs encoding one or more of the Pmtps using interfering RNA, antisense RNA, or the like. The host cells can further include any one of the aforementioned host cells modified to produce particular N-glycan structures.

Pmtp inhibitors include but are not limited to a benzylidene thiazolidinediones. Examples of benzylidene thiazolidinediones that can be used are 5-[[3,4-bis(phenylmethoxy) phenyl]methylene]-4-oxo-2-thioxo-3-thiazolidineacetic Acid; 5-[[3-(1-Phenylethoxy)-4-(2-phenylethoxy)]phenyl]methylene]-4-oxo-2-thioxo-3-thiazolidineacetic Acid; and 5-[[3-(1-Phenyl-2-hydroxy)ethoxy)-4-(2-phenylethoxy)]phenyl]methylene]-4-oxo-2-thioxo-3-thiazolidineacetic acid.

In particular embodiments, the function or expression of at least one endogenous PMT gene is reduced, disrupted, or deleted. For example, in particular embodiments the function or expression of at least one endogenous PMT gene selected from the group consisting of the PMT1, PMT2, PMT3, and PMT4 genes is reduced, disrupted, or deleted; or the host cells are cultivated in the presence of one or more PMT inhibitors. In further embodiments, the host cells include one or more PMT gene deletions or disruptions and the host cells are cultivated in the presence of one or more Pmtp inhibitors. In particular aspects of these embodiments, the host cells also express a secreted α-1,2-mannosidase.

PMT deletions or disruptions and/or Pmtp inhibitors control O-glycosylation by reducing O-glycosylation occupancy, that is, by reducing the total number of O-glycosylation sites on the glycoprotein that are glycosylated. The further addition of an α-1,2-mannosidase that is secreted by the cell controls O-glycosylation by reducing the mannose chain length of the O-glycans that are on the glycoprotein. Thus, combining PMT deletions or disruptions and/or Pmtp inhibitors with expression of a secreted α-1,2-mannosidase controls O-glycosylation by reducing occupancy and chain length. In particular circumstances, the particular combination of PMT deletions or disruptions, Pmtp inhibitors, and α-1,2-mannosidase is determined empirically as particular heterologous glycoproteins (Fabs and antibodies, for example) may be expressed and transported through the Golgi apparatus with different degrees of efficiency and thus may require a particular combination of PMT deletions or disruptions, Pmtp inhibitors, and α-1,2-mannosidase. In another aspect, genes encoding one or more endogenous mannosyltransferase enzymes are deleted. This deletion(s) can be in combination with providing the secreted α-1,2-mannosidase and/or PMT inhibitors or can be in lieu of providing the secreted α-1,2-mannosidase and/or PMT inhibitors.

Thus, the control of O-glycosylation can be useful for producing particular glycoproteins in the host cells disclosed herein in better total yield or in yield of properly assembled glycoprotein. The reduction or elimination of O-glycosylation appears to have a beneficial effect on the assembly and transport of whole antibodies and Fab fragments as they traverse the secretory pathway and are transported to the cell surface. Thus, in cells in which O-glycosylation is controlled, the yield of properly assembled antibodies or Fab fragments is increased over the yield obtained in host cells in which O-glycosylation is not controlled.

To reduce or eliminate the likelihood of N-glycans and O-glycans with β-linked mannose residues, which are resistant to a-mannosidases, the recombinant glycoengineered *Pichia pastoris* host cells are genetically engineered to eliminate glycoproteins having α-mannosidase-resistant N-glycans by deleting or disrupting one or more of the β-mannosyltransferase genes (e.g., BMT1, BMT2, BMT3, and BMT4) (See, U.S. Pat. Nos. 7,465,577 and 7,713,719). The deletion or disruption of BMT2 and one or more of BMT1, BMT3, and BMT4 also reduces or eliminates detectable cross reactivity to antibodies against host cell protein.

Yield of glycoprotein can in some situations be improved by overexpressing nucleic acid molecules encoding mammalian or human chaperone proteins or replacing the genes encoding one or more endogenous chaperone proteins with nucleic acid molecules encoding one or more mammalian or human chaperone proteins. In addition, the expression of mammalian or human chaperone proteins in the host cell also appears to control O-glycosylation in the cell. Thus, further included are the host cells herein wherein the function of at least one endogenous gene encoding a chaperone protein has been reduced or eliminated, and a vector encoding at least one mammalian or human homolog of the chaperone protein is expressed in the host cell. Also included are host cells in which the endogenous host cell chaperones and the mammalian or human chaperone proteins are expressed. In further aspects, the lower eukaryotic host cell is a yeast or filamentous fungi host cell. Examples of the use of chaperones of host cells in which human chaperone proteins are introduced to improve the yield and reduce or control O-glycosylation of recombinant proteins has been disclosed in Published International Application No. WO 2009105357 and WO2010019487 (the disclosures of which are incorporated herein by reference). Like above, further included are lower eukaryotic host cells wherein, in addition to replacing the genes encoding one or more of the endogenous chaperone proteins with nucleic acid molecules encoding one or more mammalian or human chaperone proteins or overexpressing one or more mammalian or human chaperone proteins as described above, the function or expression of at least one endogenous gene encoding a protein O-mannosyltransferase (PMT) protein is reduced, disrupted, or deleted. In particular embodiments, the function of at least one endogenous PMT gene selected from the group consisting of the PMT1, PMT2, PMT3, and PMT4 genes is reduced, disrupted, or deleted.

In addition, O-glycosylation may have an effect on an antibody or Fab fragment's affinity and/or avidity for an antigen. This can be particularly significant when the ultimate host cell for production of the antibody or Fab is not the same as the host cell that was used for selecting the antibody. For example, O-glycosylation might interfere with an antibody's or Fab fragment's affinity for an antigen, thus an antibody or Fab fragment that might otherwise have high affinity for an antigen might not be identified because O-glycosylation may interfere with the ability of the antibody or Fab fragment to bind the antigen. In other cases, an antibody or Fab fragment that has high avidity for an antigen might not be identified because O-glycosylation interferes with the antibody's or Fab fragment's avidity for the antigen. In the preceding two cases, an antibody or Fab fragment that might be particularly effective when produced in a mammalian cell line might not be identified because the host cells for identifying and selecting the antibody or Fab fragment was of another cell type, for example, a yeast or fungal cell (e.g., a *Pichia pastoris* host cell). It is well known that O-glycosylation in yeast can be significantly different from O-glycosylation in mammalian cells. This is particularly relevant when comparing wild type yeast O-glycosylation with mucin-type or dystroglycan type O-glycosylation in mammals. In particular cases, O-glycosylation might enhance the antibody or Fab fragments affinity or avidity for an antigen instead of interfere with antigen binding. This effect is undesirable when the production host cell is to be different from the host cell used to identify and select the antibody or Fab fragment (for example, identification and selection is done in yeast and the production host is a mammalian cell) because in the production host the O-glycosylation will no longer be of the type that caused the enhanced affinity or avidity for the antigen. Therefore, controlling O-glycosylation can enable use of the materials and methods herein to identify and select antibodies or Fab fragments with specificity for a particular antigen based upon affinity or avidity of the antibody or Fab fragment for the antigen without identification and selection of the antibody or Fab fragment being influenced by the O-glycosylation system of the host cell. Thus, controlling O-glycosylation further enhances the usefulness of yeast or fungal host cells to identify and select antibodies or Fab fragments that will ultimately be produced in a mammalian cell line.

Those of ordinary skill in the art would further appreciate and understand how to utilize the methods and materials described herein in combination with other *Pichia pastoris* and yeast cell lines that have been genetically engineered to produce specific N-glycans or sialylated glycoproteins, such as, but, not limited to, the host organisms and cell lines described above that have been genetically engineered to produce specific galactosylated or sialylated forms. See, for example, US 2006-0286637, Production of Sialylated N-Glycans in Lower Eukaryotes, in which the pathway for galactose uptake and utilization as a carbon source has been genetically modified, the description of which is incorporated herein as if set forth at length.

Additionally, the methods herein can be used to produce the above described recombinant Fc-containing polypeptides in other lower eukaryotic cell lines which have been engineered to produce human-like and human glycoproteins that do not have α 2,6 sialyltransferase activity. The methods can also be used to produce the above described recombinant Fc-containing polypeptides in eukaryotic cell lines in which production of sialylated N-glycans is an innate feature.

Levels of α 2,3 and α 2,6 linked sialic acid on the Fc-containing polypeptides can be measured using well known techniques including nuclear magnetic resonance (NMR), normal phase high performance liquid chromatography (HPLC), and high performance anion exchange chromatography with pulsed amperometric detection (HPAEC-PAD).

Biological Properties of Fc Muteins

For many Fc-containing polypeptides the lack of or significant decrease in effector function, as shown by decreased FcγR and C1q binding, Idusogie et al., J. Immunology 164(8): 4178-84 (2000) and Shields et al., J. Biol. Chem. 276: 6591-6604 (2001), and increased anti-inflammatory properties would be desirable characteristics. Applicants herein have discovered that specific modifications of amino acid positions 243 and 264 in the Fc region of an IgG can impart a lack of, or a significant decrease in, effector function irrespective of the presence of sialylation at the terminal glycan positions. Specifically, Applicants have found that modification to residues F243 and V264 in the Fc region to alanine resulted in an antibody with decreased binding to Fcγ receptors and C1q. It is notable that antibodies produced with these Fc region modifications exhibited decreased binding to Fcγ receptors, regardless of whether they were found to have the α 2,6-linked sialic acid form as the terminal glycan.

As such, Applicants have developed a double Fc mutein, F243A/V264A, which will produce Fc-containing polypeptides having the aforesaid desired characteristics. The Examples herein comprise transforming a host cell with a polynucleotide vector encoding a Fc-containing polypeptide comprising mutations at positions 243 and 264 of the Fc region, and culturing the transformed host cell to produce the Fc-containing polypeptide.

Production of Fc-Containing Polypeptides

The Fc-containing polypeptides of the invention can be made according to any method known in the art suitable for generating polypeptides comprising a Fc region. In one embodiment, the Fc-containing polypeptide is an antibody or an antibody fragment (including, without limitation a polypeptide consisting of or consisting essentially of the Fc region of an antibody). In another embodiment, the Fc-containing polypeptide is an immunoadhesin. Methods of preparing antibody and antibody fragments are well known in the art. Methods of introducing point mutations into a polypeptide, for example site directed mutagenesis, are also well known in the art.

In the Examples disclosed herein, an IgG1 heavy and light chain containing a consensus $C_H2$ sequence and the Fc double mutants described herein were expressed in two different glycoengineered *Pichia pastoris* strains. As described in the Examples that follow, the heavy and light chain gene sequences were under the control of a methanol inducible promoter, AOX1, and incorporated a bleomycin (Zeocin) selection marker. This strategy integrates the entire expression cassette into the Trp2 locus by homologous DNA recombination.

Figure 2:
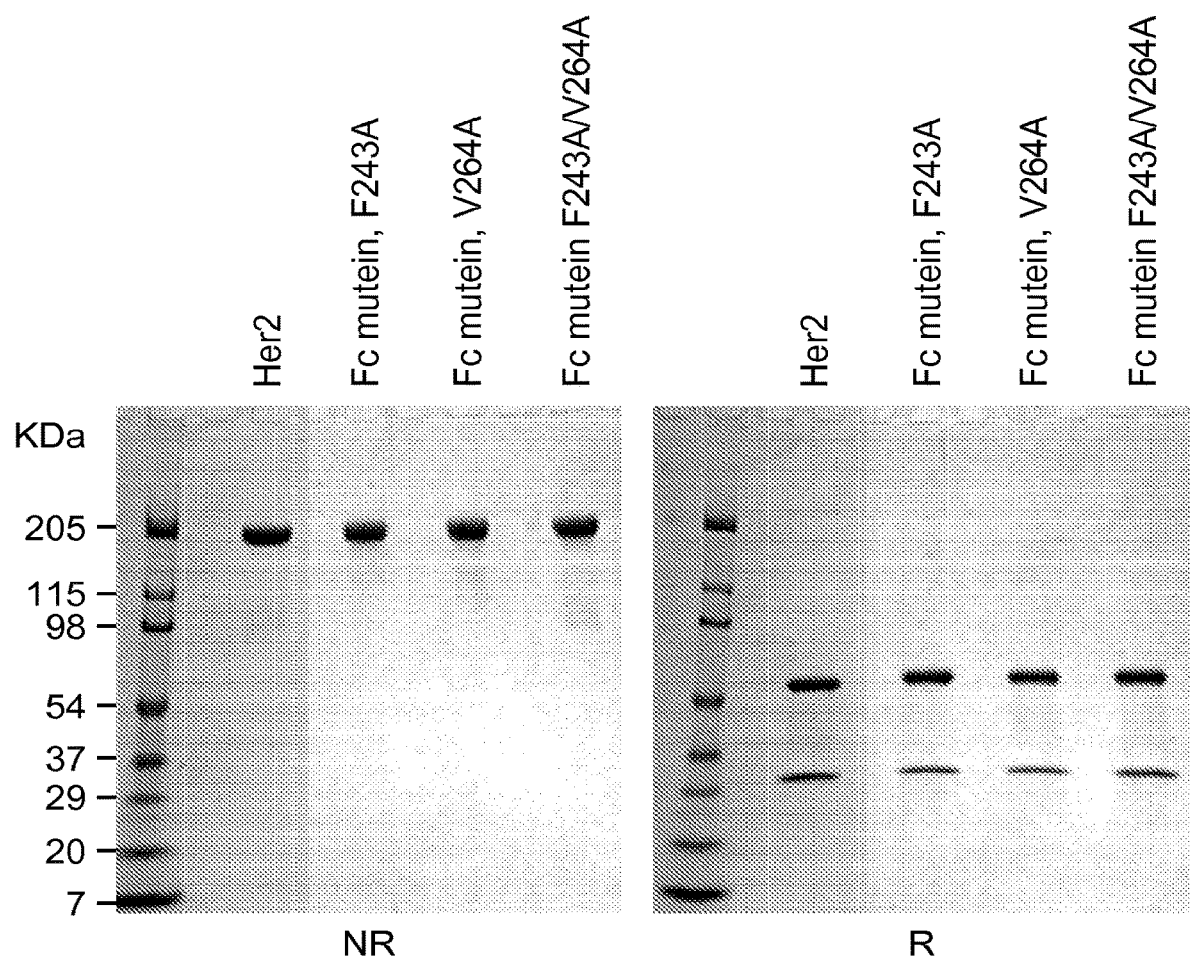
FIG. 2 is a representation of the gels from an SDS-PAGE analysis characterizing the non-reduced (NR) and reduced (R) antibodies produced by the materials and methods herein. Lane 1 contains an anti-Her2 monoclonal antibody, Her2; Lane 2 contains a single Fc mutein, F243A; Lane 3 contains a single Fc mutein, V264A; and Lane 4 contains a double Fc mutein, F243A/V264A.
Figure 3:
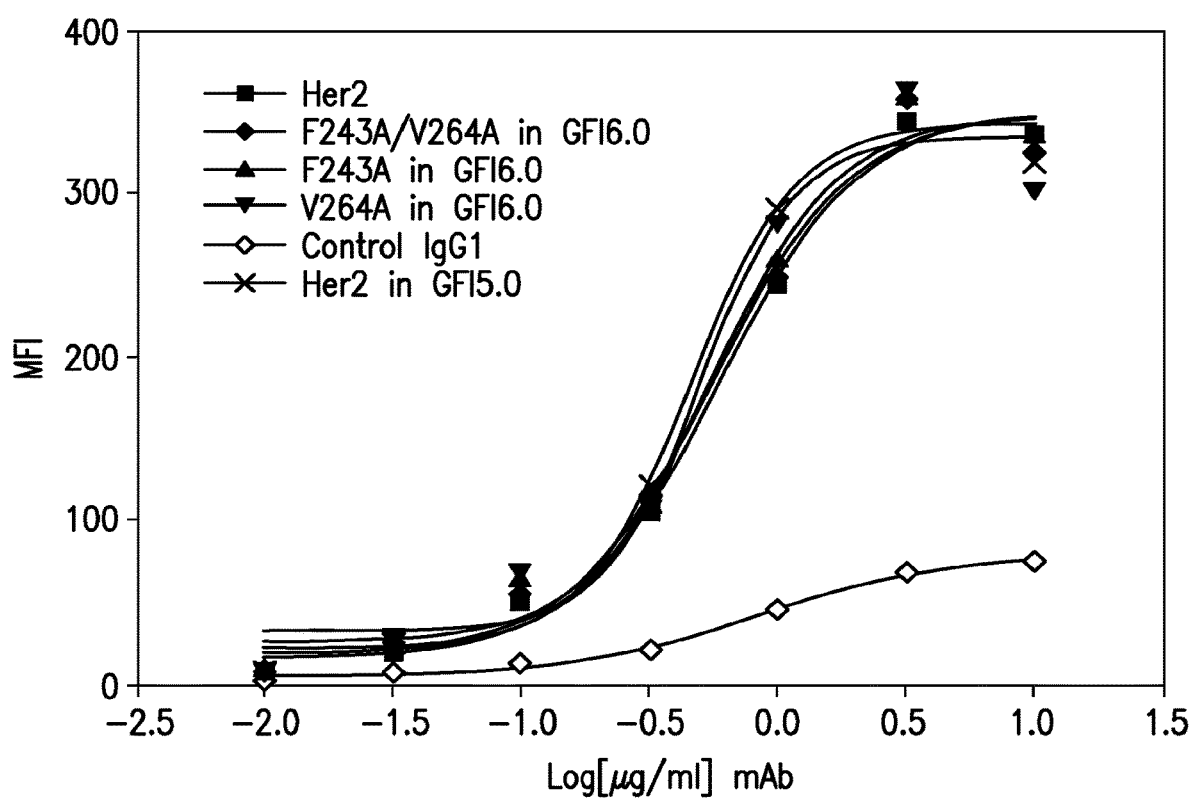
FIG. 3 illustrates antigen affinity for various antibodies produced by the materials and methods herein as determined by a cell based assay using an SK-BR3 cell line, a Her2-overexpressing human breast cancer line. ■—Her2; ♦—F243A/V264A GS6.0 glycosylation; ▲—F243A with GS6.0 glycosylation; ▼—V264A with GS6.0 glycosylation; ◊—Control IgG; x—Pichia pastoris Her2 produced with GFI 5.0 glycosylation.

Secreted antibodies were captured from the fermentation broth by protein A affinity chromatography followed by a Source 30S cation exchange purification step. Purified antibodies were characterized by SDS-PAGE (FIG. 2) and size exclusion chromatography (SEC) and reverse phase HPLC to assess proper assembly. As seen in FIG. 2, the antibodies produced by the materials and methods herein had a purity profile on SDS-PAGE that was similar to that for a mammalian cell (CHO) produced Her2 antibody. IgG analysis by SEC and reverse phase HPLC further demonstrated that antibodies made from the Fc mutein glycoengineered strains were properly assembled and were similar to the mammalian cell produced antibody in terms of assembly (data not shown). Antigen affinity for the various antibodies made by the materials and methods herein was determined by a cell based assay using a SK-BR3 cell line, which in this instance was a Her2-overexpressing human breast cancer line. As expected, all of the antibodies, including the Fc muteins, bound equally well to the SK-BR3 cell line (FIG. 3).

N-Glycan Analysis of Fc Muteins

For many glycoproteins, including certain antibodies, sialylation of the terminal N-linked glycan of an IgG Fc region is essential for producing glycoproteins and antibodies that have the correct conformation to impart therapeutic activity. See, for example, Anthony et al., Science, 320: 373-376 (2008), where terminal sialylation was correlated to anti-inflammatory activity for an IVIG preparation. Sialylation requires the presence of a penultimate galactose, upon which the sialyl transferase acts to form the sialylated glycan. Thus, glycoproteins lacking one or more terminal galactose glycoforms cannot produce antibodies having the α 2,6-linked sialic acid composition associated with anti-inflammatory activity.

Typically, antibodies produced in mammalian cell culture, such as CHO cells, have a glycoform composition comprising: G0F (37%), G1F (43%), G2F (9%), G0 (4%), G1 (3%) and Man5 (3%), which have little or no terminal galactose to act as a substrate for the transfer of sialic acid. In the case of CHO cell production, the terminal glycan produced is the α2,3-linked form; CHO cells do not express an α2,6 sialyl transferase necessary to produce the a 2,6-linked form of sialic acid, which has been associated with anti-inflammatory activity. However, overexpression of a specific α2,6 sialyltranferase in CHO can give rise to a mixture of α2,3-linked and α2,6-linked sialic acid (Bragonzi et al., BBA 1474:273-282 (2000); Biochem. Biophys. Res. Comm. 289: 243-249 (2001)). Glycoengineered *Pichia pastoris* GFI5.0 strains, which are capable of producing high levels of galactosylated non-antibody proteins, such as erythropoietin (Hamilton et al., Science 313: 1441-1443 (2006)), produce antibodies with relatively low amounts of a terminal galactose that can be acted upon to form the α 2,6-linked sialylated form (FIG. 4). Antibodies produced in such *Pichia pastoris* strains typically have a composition including glycoforms G0 (60%), G1 (17%), G2 (4%) and Man5 (8%). Even antibodies produced in *Pichia pastoris* GFI6.0 strains, which have a glycan composition comprising G0 (43.5%), G1 (20.8%), G2(2.7%), NANAGalGlcNAcMan$_5$GlcNAc$_2$ (5.5%), and NANAGal$_2$GlcNAc$_2$Man$_3$GlcNAc$_2$ (4.9%), have relatively low levels of the α 2,6-linked sialylated form. Thus, antibodies produced in GFI 5.0 and 6.0 strains have much lower levels of galactosylation and sialylation compared to non-antibody proteins (such as erythropoietin) produced in the same strains.

The N-glycan composition of the Her2 antibody and corresponding Fc mutein antibodies produced herein in glycoengineered *Pichia pastoris* GFI5.0 and GFI6.0 strains were analyzed by matrix-assisted laser desorption ionization/time-of-flight (MALDI-TOF) mass spectrometry after release from the antibody with peptide-N-glycosidase F (FIGS. 4-8). Released carbohydrate composition of the Her2 and the Fc mutein antibodies was quantitated by HPLC on an ALLTECH® PREVAIL™ carbo (Alltech Associates, Deerfield IL) column.

Figure 7:
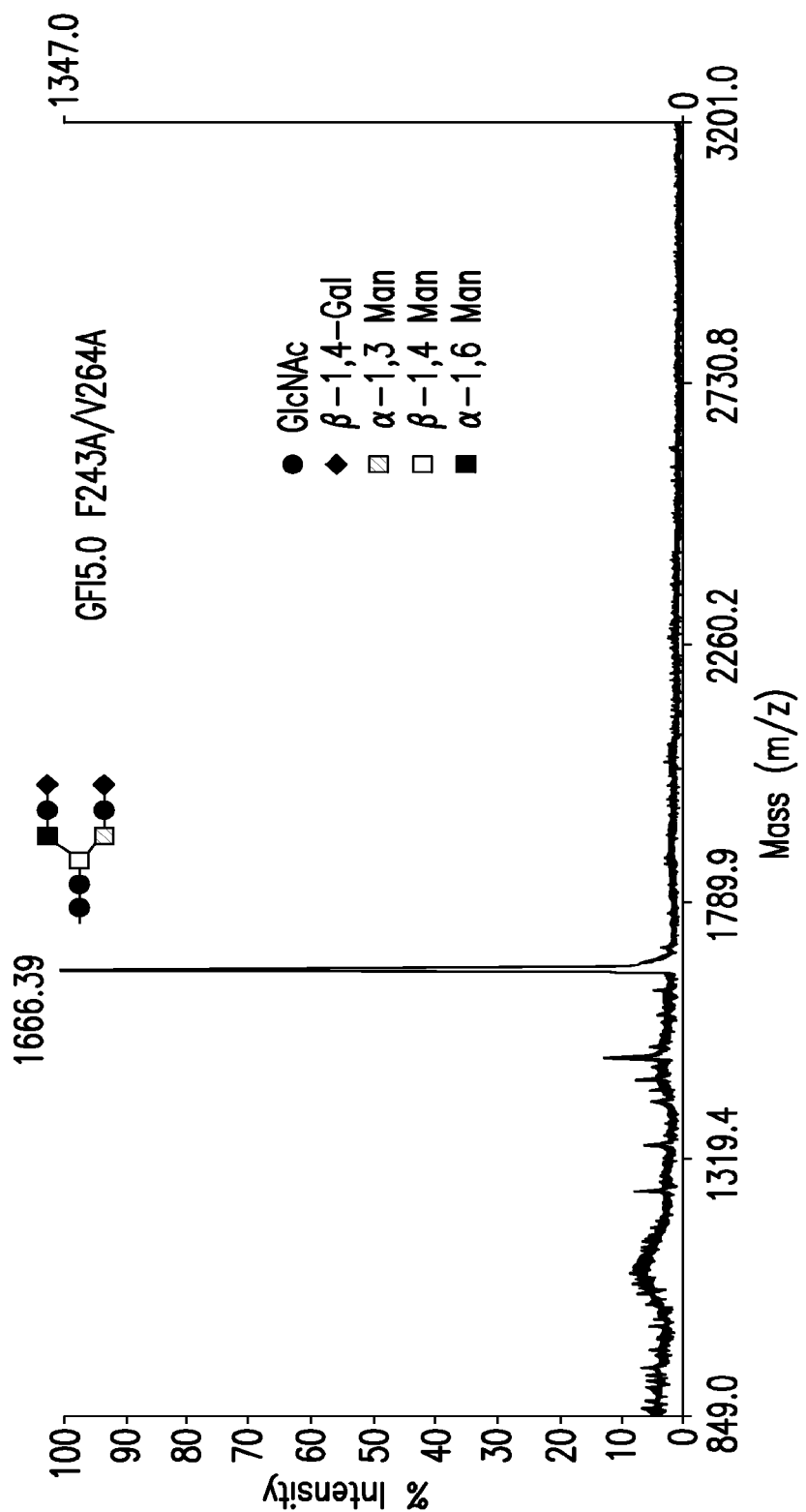
FIG. 7 illustrates a MALDI-TOF MS analysis of N-glycans of a double Fc mutein, F243A/V264A, antibody produced in GFI 5.0 strain YDX557. The major peak corresponds to $Gal_2GlcNAc_2Man_3GlcNAc_2$, 1668.39.
Figure 8:
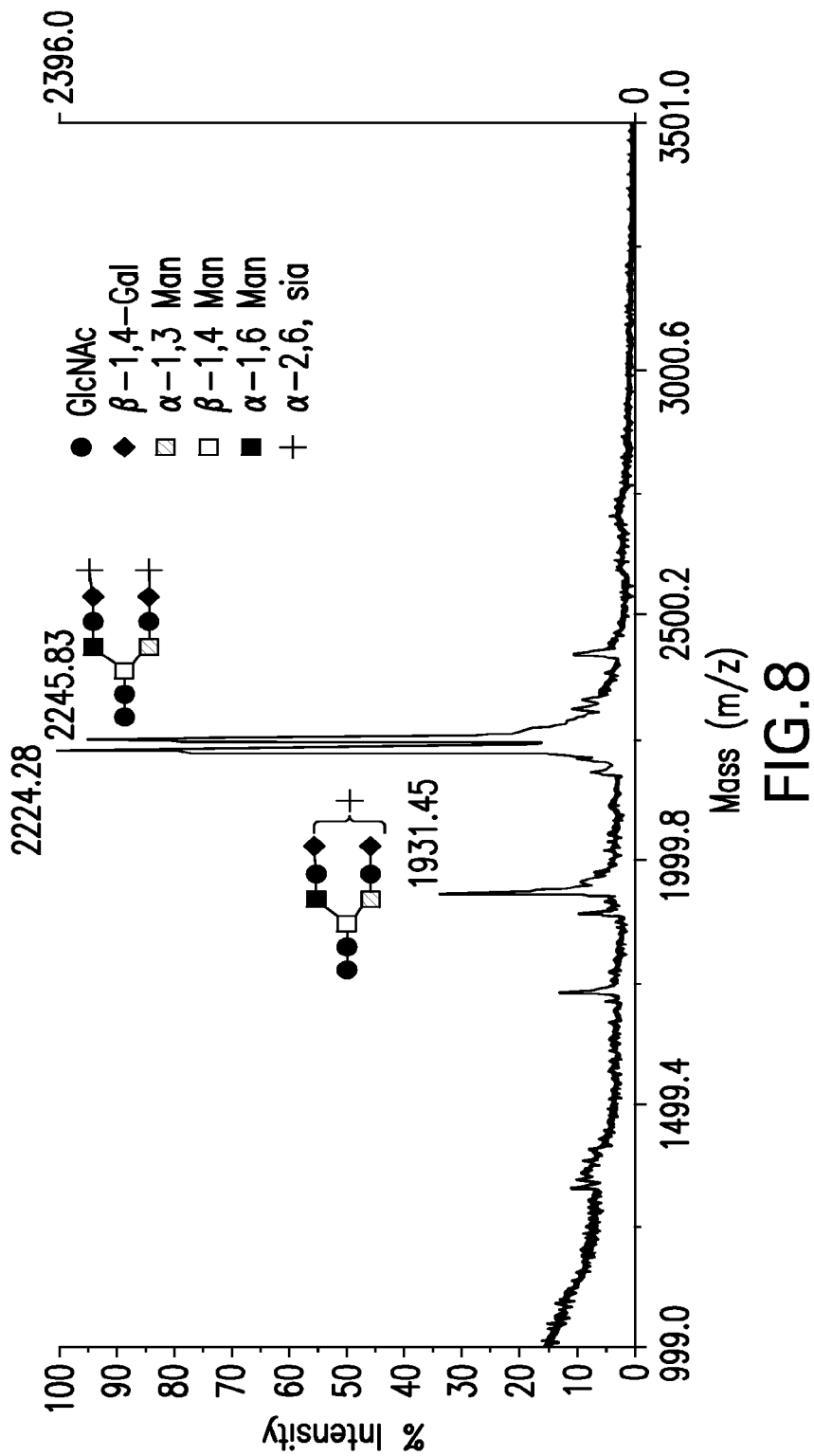
FIG. 8 illustrates a MALDI-TOF MS analysis of N-glycans of a double Fc mutein, F243A/V264A, antibody produced in GFI 6.0 strain YGLY4563. The double peaks at 2224.28 and 2245.83 (predominant) correspond to $NANAGal_2GlcNAc_2Man_3GlcNAc_2$ and $NANA_2Gal_2GlcNAc_2Man_3GlcNAc_2$, respectively.

Glycoforms of the *Pichia pastoris* Her2 antibody from the GFI5.0 strain included biantennary G0, G1, and G2 and other neutral glycans, with G0 as the dominant glycoform (FIG. 4). This glycan composition is consistent with that produced commercially in CHO cells, with the exception that the *Pichia pastoris* derived antibody inherently lacks fucose. Conversely, the glycoforms from the Fc mutein antibodies produced in GFI5.0 have dissimilar glycan compositions. The single Fc mutein antibodies, either F243A or V264A, exhibited an increase in galactosylated N-glycans, which can serve as the substrate for the α 2,6 sialyl transferase, as seen from the highest peak on MALDI-TOF mass spectrometry (FIGS. 5 and 6), while the N-glycan composition for the Fc double mutein antibody, F243A/V264A, exhibited an even greater increase with over 80% of the total N-glycans galactosylated (FIG. 7). The level of G2 (bi-galactosylated N-glycan) present on the Fc double mutein antibody represented the greatest proportion of G2 seen for any antibody evaluated by Applicants. When these same Fc mutein antibodies were expressed in the GFI6.0 strain, α 2,6-linked sialic acid was added to G1 (mono-galactosylated) or G2 (bi-galactosylated) N-glycans. For the single Fc mutein antibody, nearly all of the G2 N-glycan had been converted to a sialylated glycan (data not shown). While antibodies produced from the single Fc muteins exhibited a very high level of α 2,6-linked sialylation (40-51%, see Table 3), the level was less than that for the antibodies produced from the Fc double mutein (FIG. 8 and Table 3) where 74% sialylation was achieved with bioreactor fermentation and 91% or greater sialylation was achieved in small scale fermentation.

Without wishing to be bound by any theory, Applicants believe that the sialic acid transfer to the Fc oligosaccharide is enhanced by the more open pocket configuration of the $C_H2$ domain imparted by the Fc double mutein as compared to the Fc single mutein. It should also be noted that the α 2,6 form of sialic acid produced from a GFI6.0 strain is the same form produced in humans and differs from the α 2,3-linked sialic acid form present on antibodies produced in CHO cell lines, Jassal et al., Biochem. Biophys. Res. Comm. 289: 243-249, 2001.

FcγR Binding of Fc Muteins

Using an ELISA based assay, Applicants compared Fc gamma receptor (FcγR) binding for the *Pichia pastoris* Her2 antibody, single and double Fc mutein antibodies and the Her2 antibody. As shown in the experiments described in Examples 11 and 15, the Fc double mutein had a decrease in affinity to FcγRI. As FcγRI is a receptor shown to stimulate an immune response upon antibody binding, these data suggest that double mutein antibodies will be less capable of promoting an immune response.

For FcγRIIb, a receptor that has lower antibody affinity as compared to FcγRI and has been shown to inhibit an immune response, the double Fc mutein binds with reduced affinity. For FcγRIIa, the double Fc mutein also appears to bind with reduced affinity. These data suggest that the conformational structure of the double mutein antibodies has been altered such that the ability to inhibit an immune response via FcγRIIa and FcγRIIb/c has been significantly decreased or eliminated.

FcγRIIIa-F158 and FcγRIIIa-V158 are polymorphisms of a receptor known to stimulate an immune response, but have lower antibody affinity as compared to FcγR1. The Fc double mutein had little affinity for FcγRIIIa-F158 while still retaining some affinity for FcγRIIIa-V158. Taken together, these data suggest that the double Fc mutein is less prone to activating and recruiting immune cells such as macrophages, monocytes and natural killer cells as compared to parent antibody.

C1q Binding of Fc Muteins

Antibody-C1q binding is an important parameter for complement dependent cytotoxicity. Binding activity (affinity) of an immunoglobulin (IgG) molecule to C1q may be determined by a cell based assay such as the one provided herein in Example 13. Those of ordinary skill in the art would recognize and appreciate that the disclosed assay can be easily adapted for use with any IgG molecule.

ADCC Effects on Fc Muteins

Figure 9A:
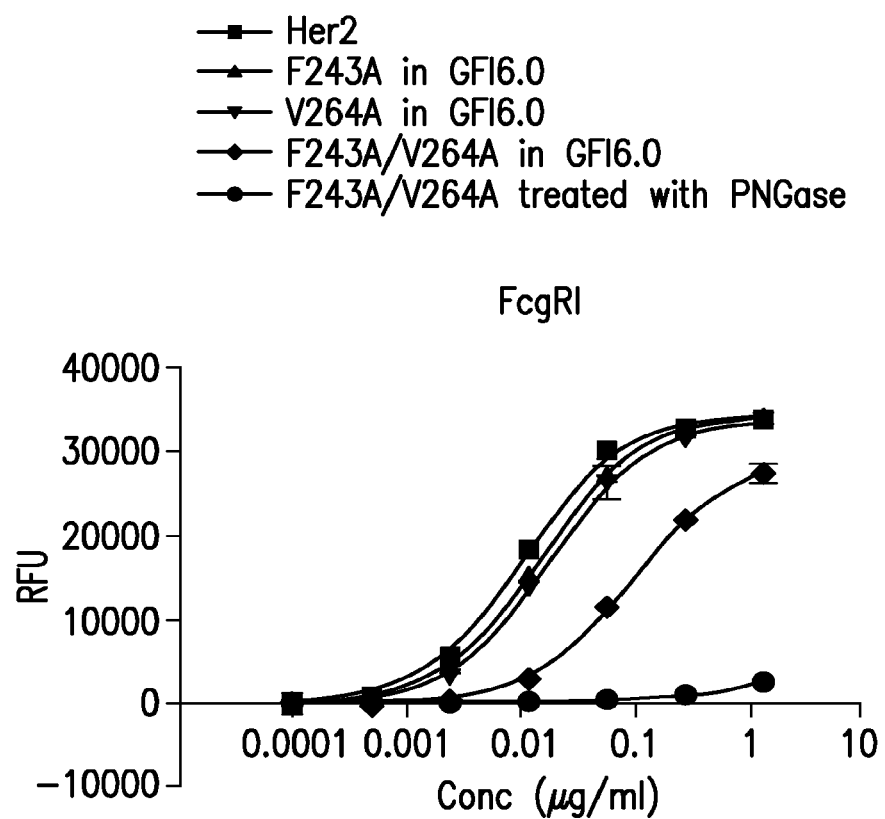
FIGS. 9A-9D are graphic representations of the FcγR binding for various antibodies produced by the materials and methods described in Example 11: FcγRIIIaLF (FIG. 9A); FcγRI (FIG. 9B); FcγRIIb/c (FIG. 9C); and FcγRIIIaLV (FIG. 9D). For FIGS. 9A-9D: ■—Her2; ▲—F243A produced in GFI 6.0; ▼V264A produced in GFI 6.0; ♦—F243A/V264A produced in GFI 6.0; ●—F243A/V264A produced in GFI 6.0 and treated with PNGase.
Figure 9B:
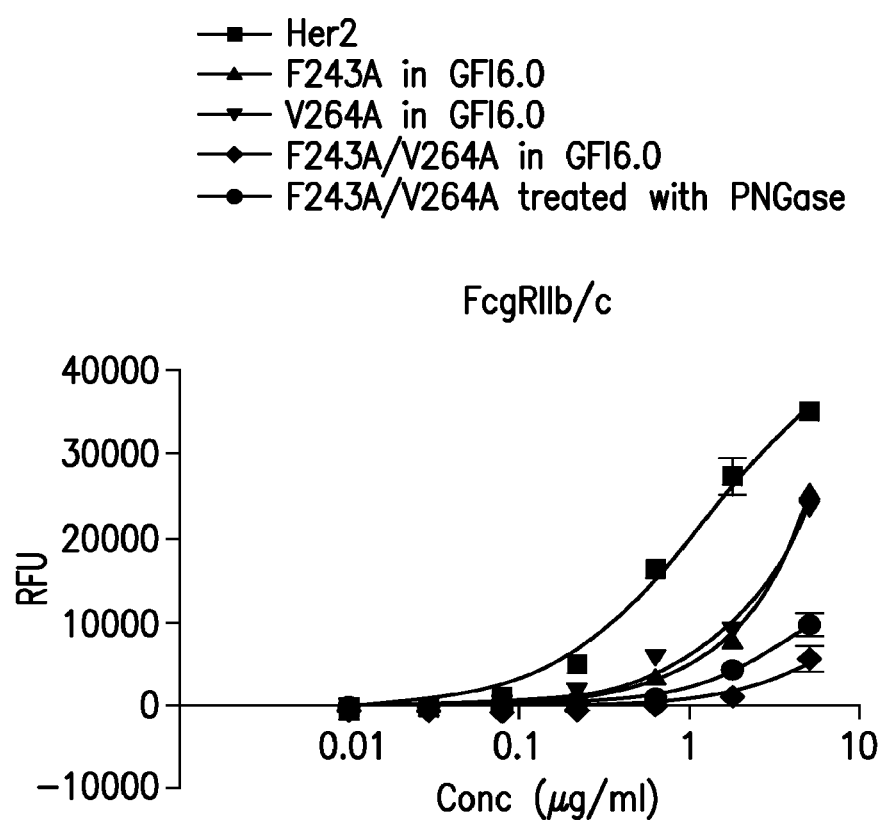
Figure 9C:
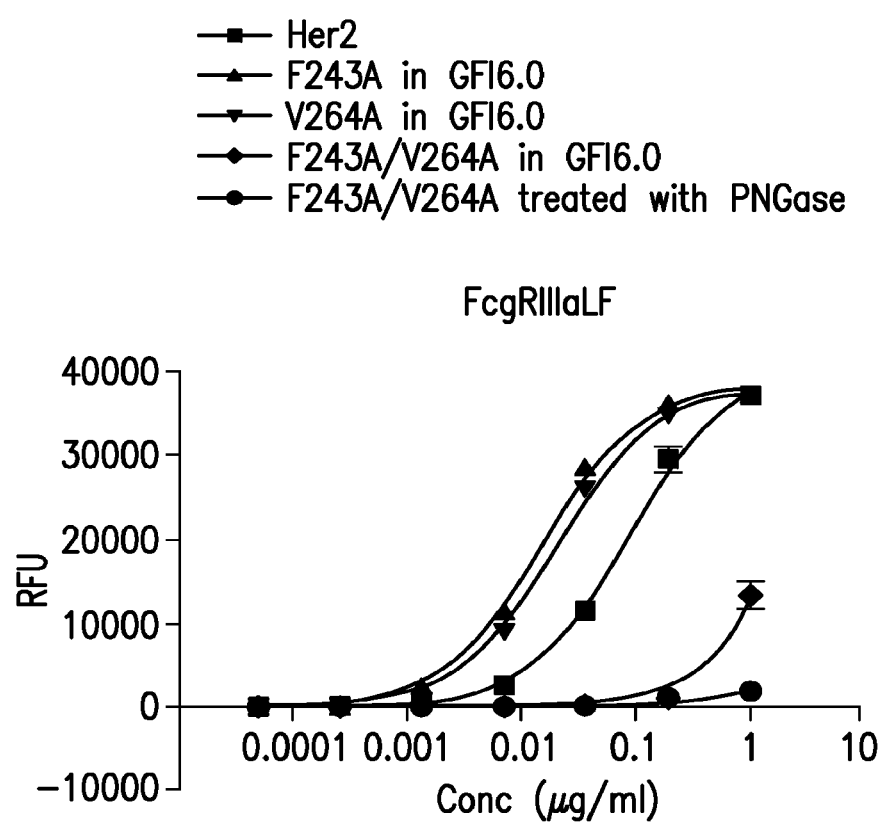

It is well established that the FcγRIIIa (CD16) receptor is responsible for antibody-dependent cell-mediated cytotoxicity (ADCC) (Daeron et al., Annu. Rev. Immunol. 15: 203-234, 1997). Applicants have found that antibodies produced from the double Fc mutein described herein have decreased FcγRIIIa binding (FIGS. 9C and D; Tables 4 and 5) and, as such, have likely lost the ability to effect FcγRIIIa-mediated ADCC.

Example 13 provides an in vitro assay for measuring B-cell depletion and fluorescence released ADCC.

Bioavailability of Fc Muteins

Bioavailability refers to the extent to and rate at which an active moiety, whether it be a drug or metabolite, enters human circulation and thereby accessing the site of action. Bioavailability of a drug is mainly affected by the properties of the dosage form as opposed to the drug's physiochemical properties, which in turn can determine its absorption potential. Chemical equivalence suggests that the drug products contain the same active ingredient(s) and in the same amount, although other inactives may differ. Similarly, bioequivalence suggests that the two drug products, when given to the same patient in the same dosing regimen, will produce equivalent concentrations of drug in circulation and tissues. Conversely, two drug products that are not identical may be capable of producing the same therapeutic effect (and adverse effects) when given to the same patient. Thus, the bioavailability of a drug is relative to a determination of any equivalence in that it may be possible to achieve therapeutic equivalence even when bioavailabilities differ. For drugs having a narrow therapeutic index, i.e. the ratio of the minimum toxic concentration to the median effective concentration, bioavailability differences may result in therapeutic nonequivalence.

Figure 12:
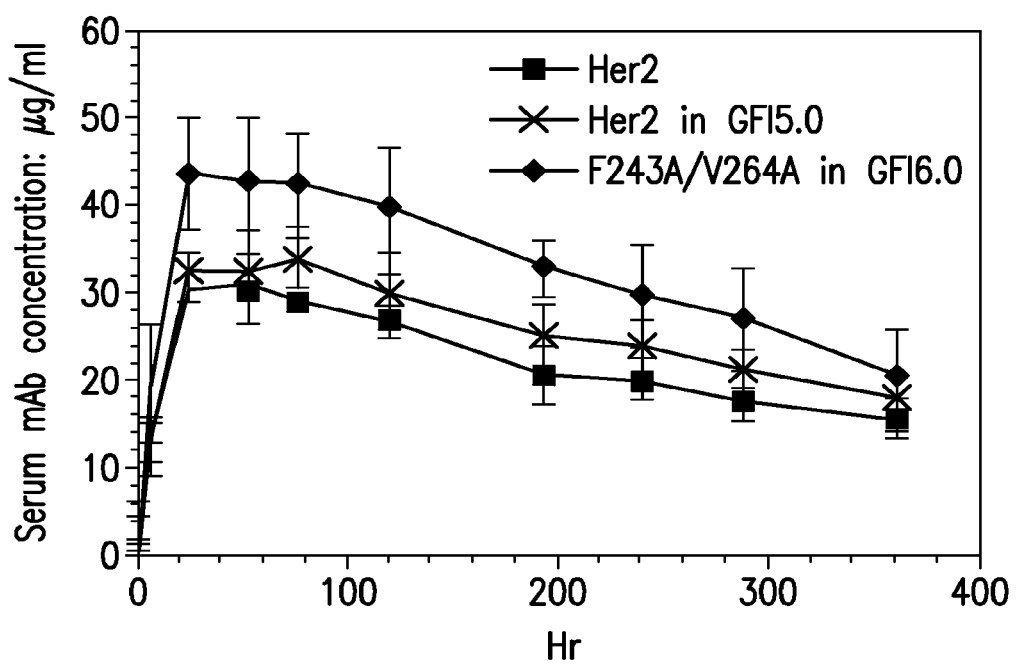
FIG. 12 is a graphic representation of serum monoclonal antibody concentration over time for mice injected with: ■—Her2; X—Her2 produced in GFI 5.0; ♦—F243A/V264A produced in GFI 6.0 as described in Example 14.
Figure 13A:
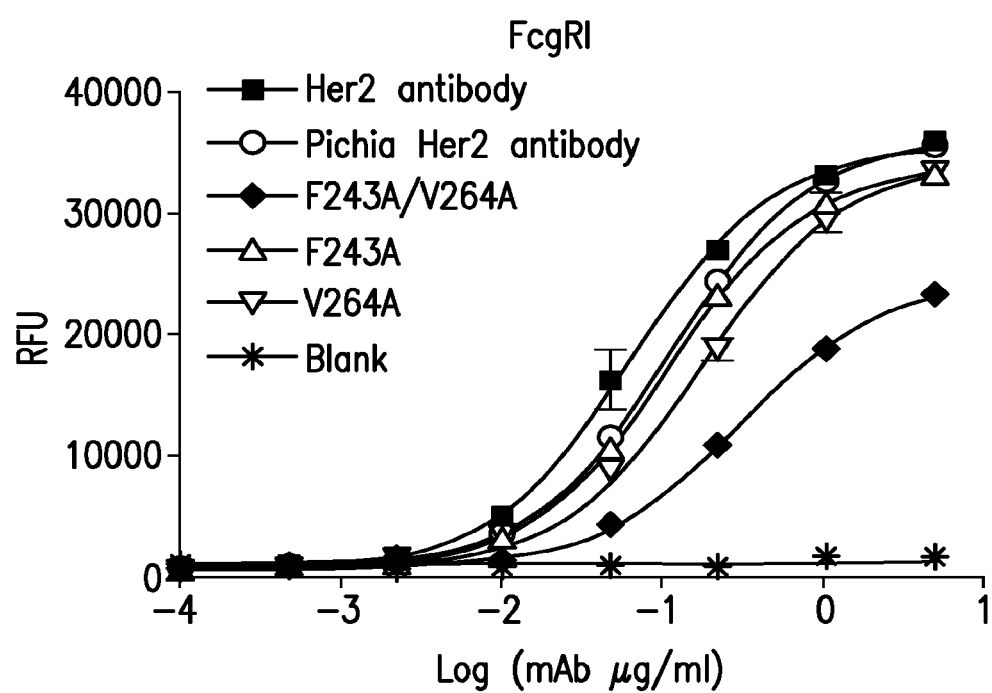
FIGS. 13A-13E are graphic representations of the FcγR binding for various antibodies described in Example 15.
Figure 13B:
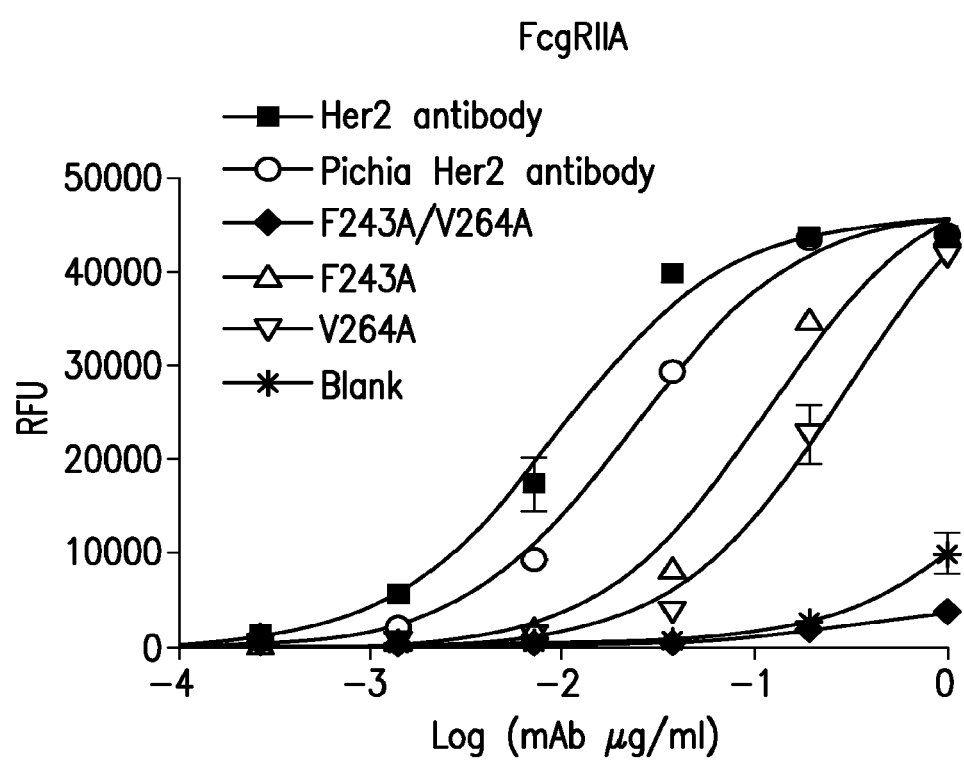
Figure 13C:
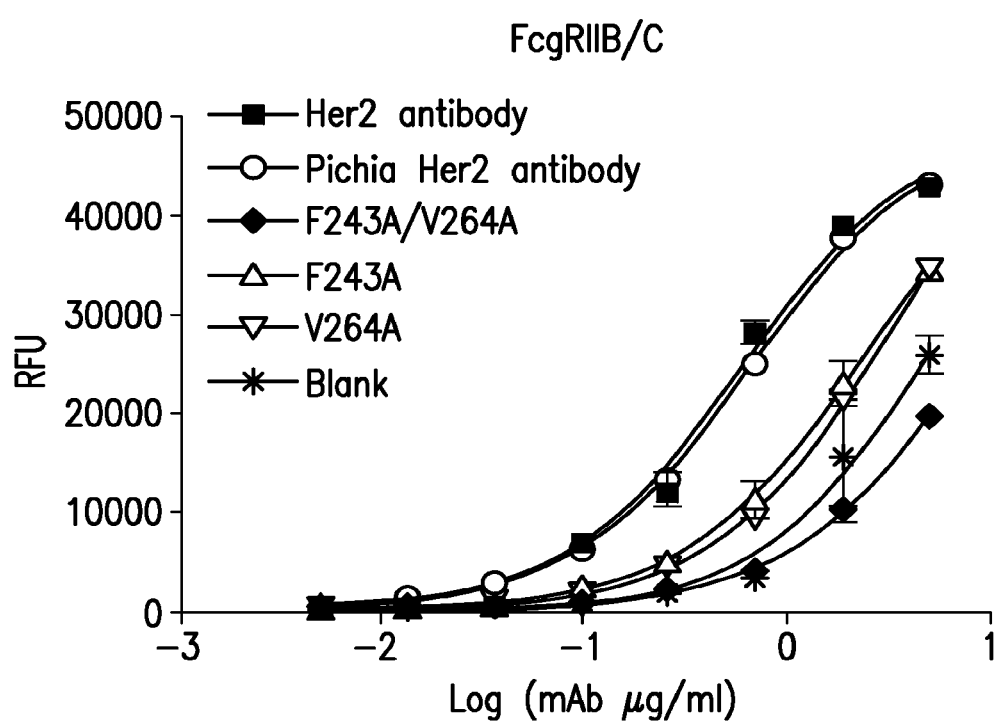
Figure 13D:
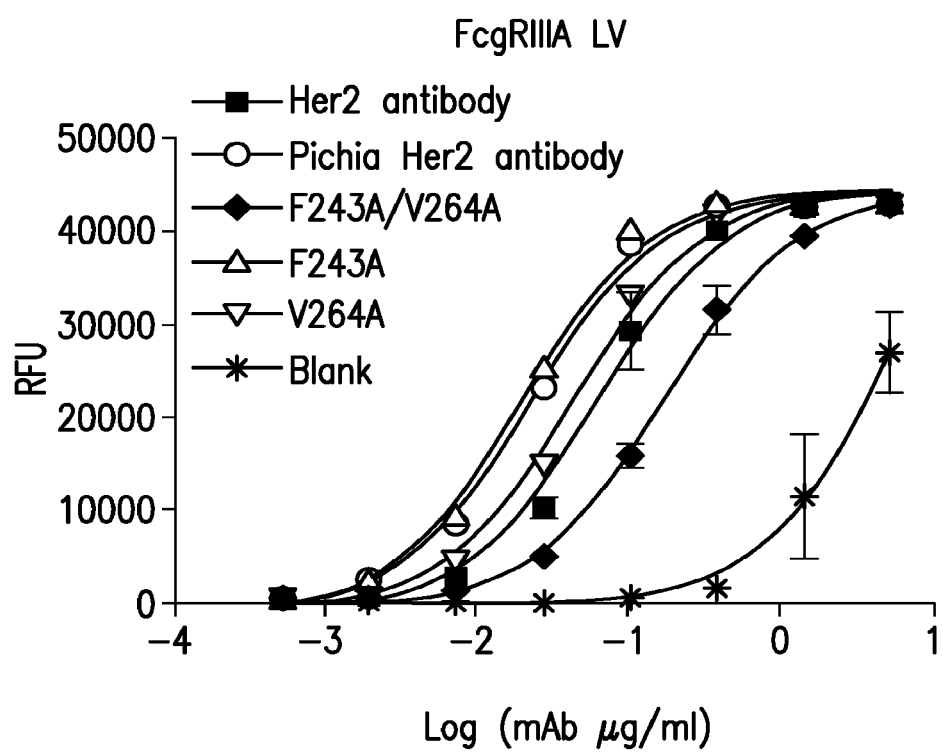
Figure 13E:
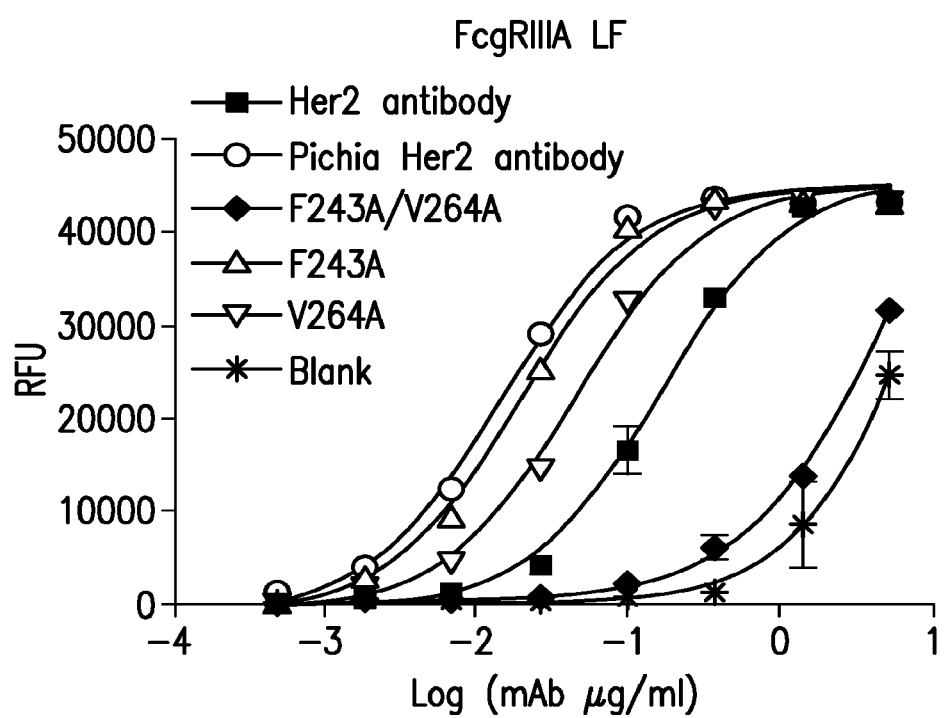
Figure 14A:
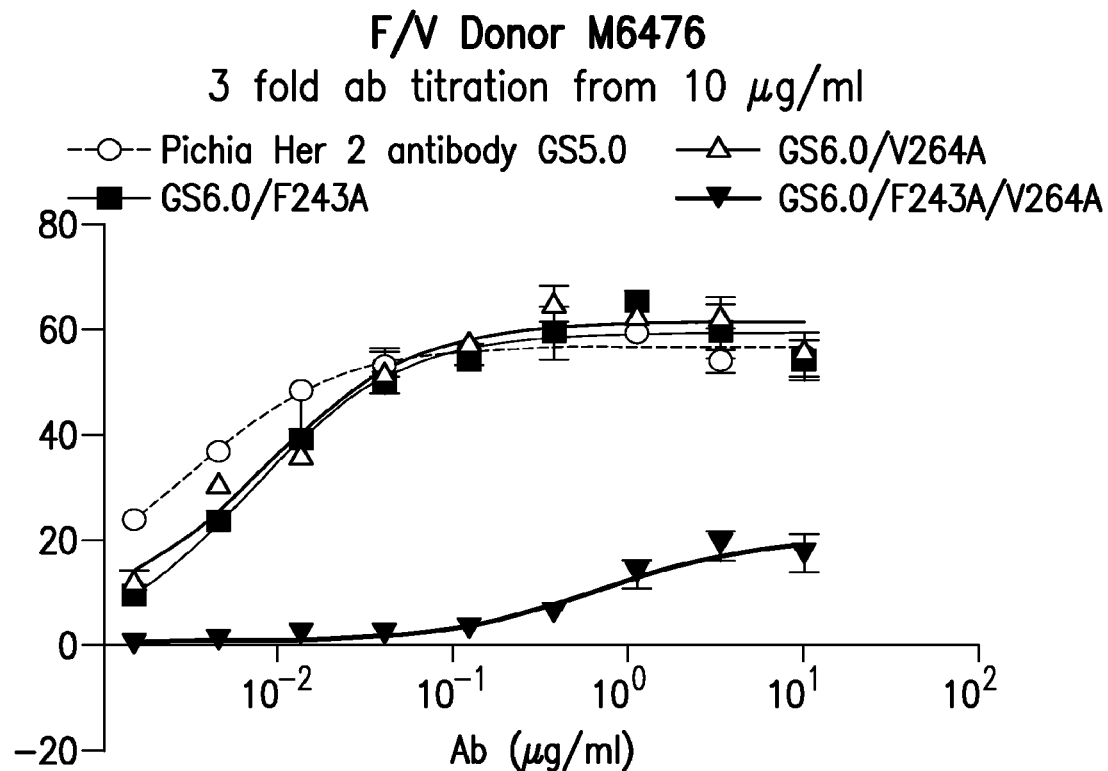
FIGS. 14A-14E are graphic representations of the ADCC response for the various antibodies produced by the materials and methods described in Example 16. The results in FIGS. 14A and 14B were from experiments using heterozygous FN effector cells. The results in FIGS. 14C and 14D were from experiments using F/F effector cells. The results in FIG. 14E were from an experiment using V/V effector cells.
Figure 14B:
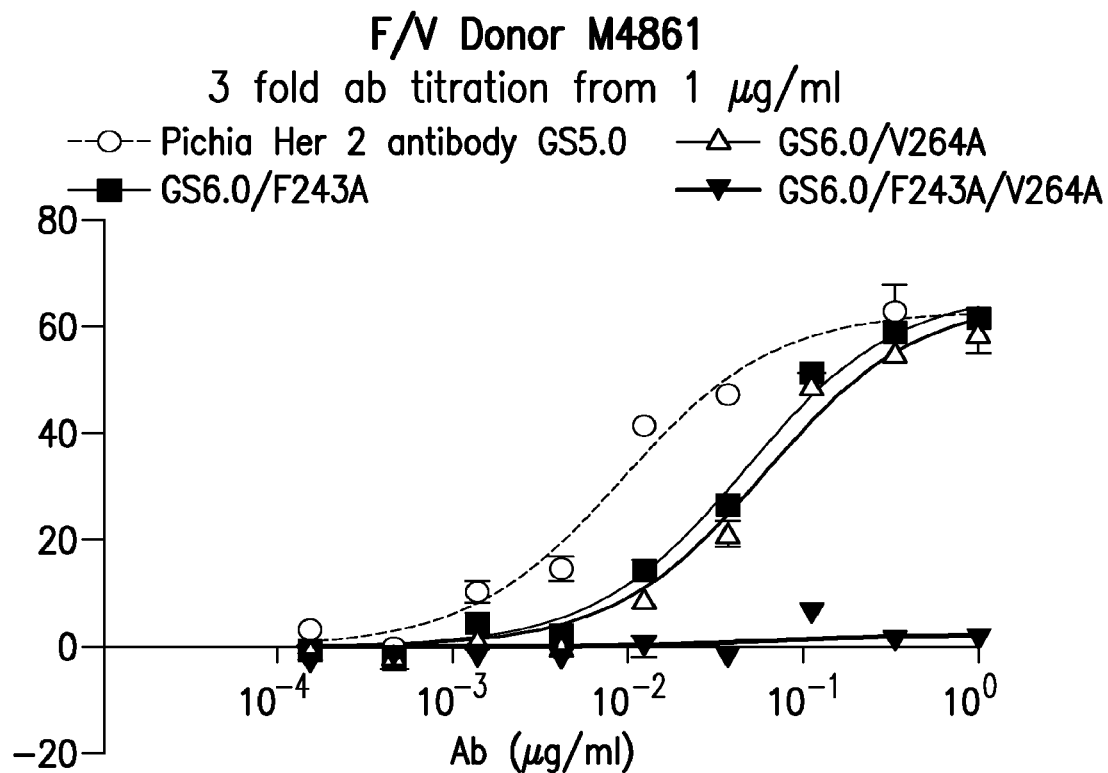
Figure 14C:
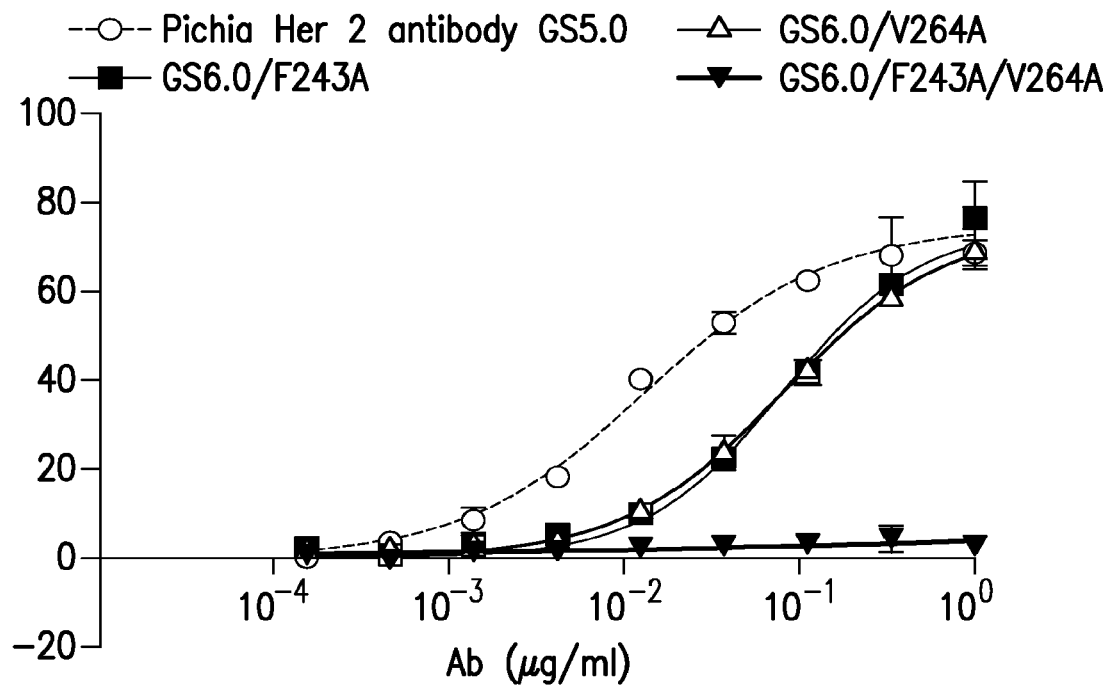
Figure 14D:
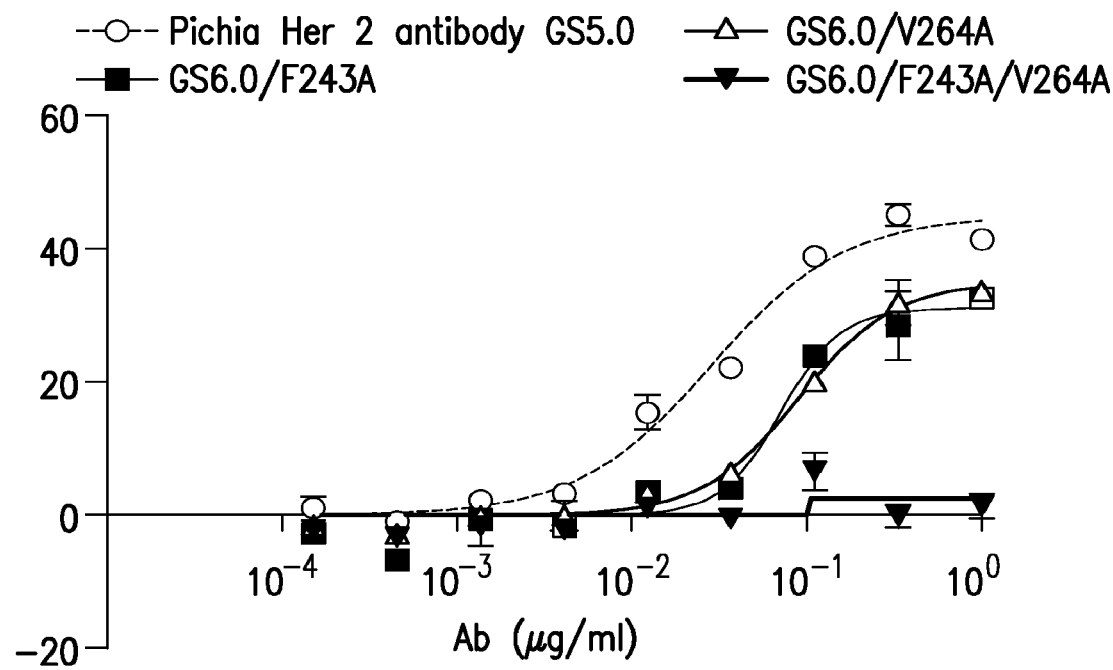
Figure 14E:
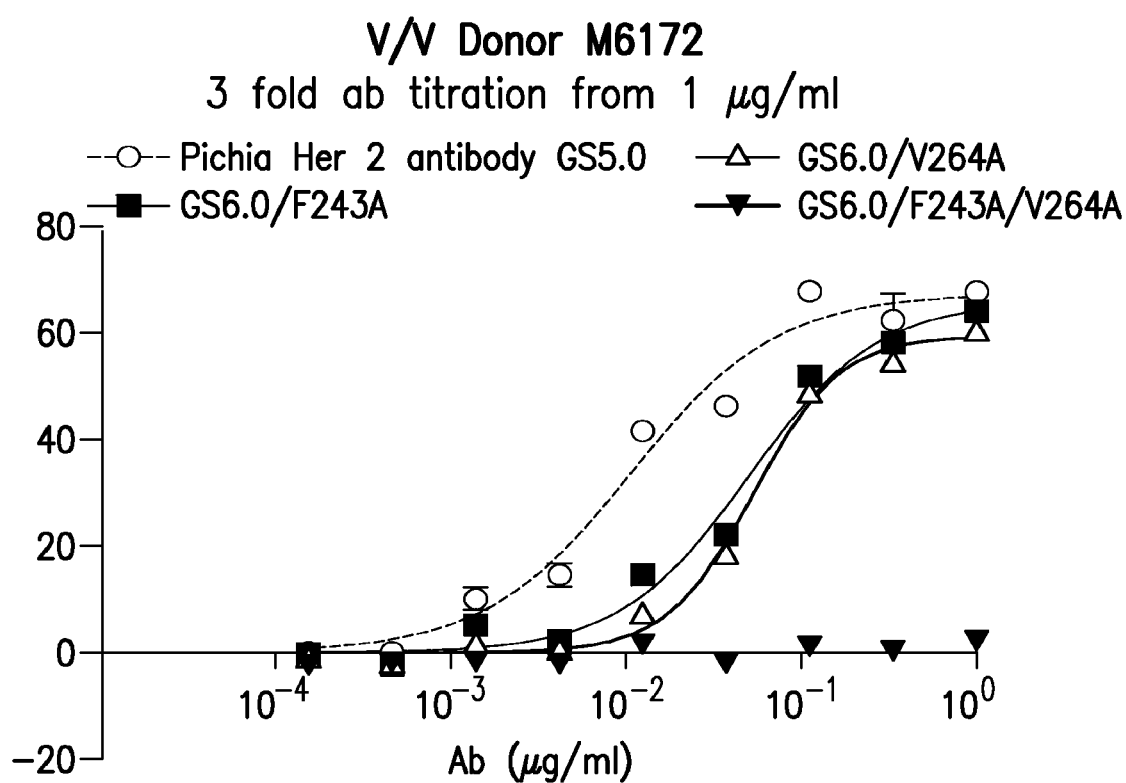
Figure 16A:
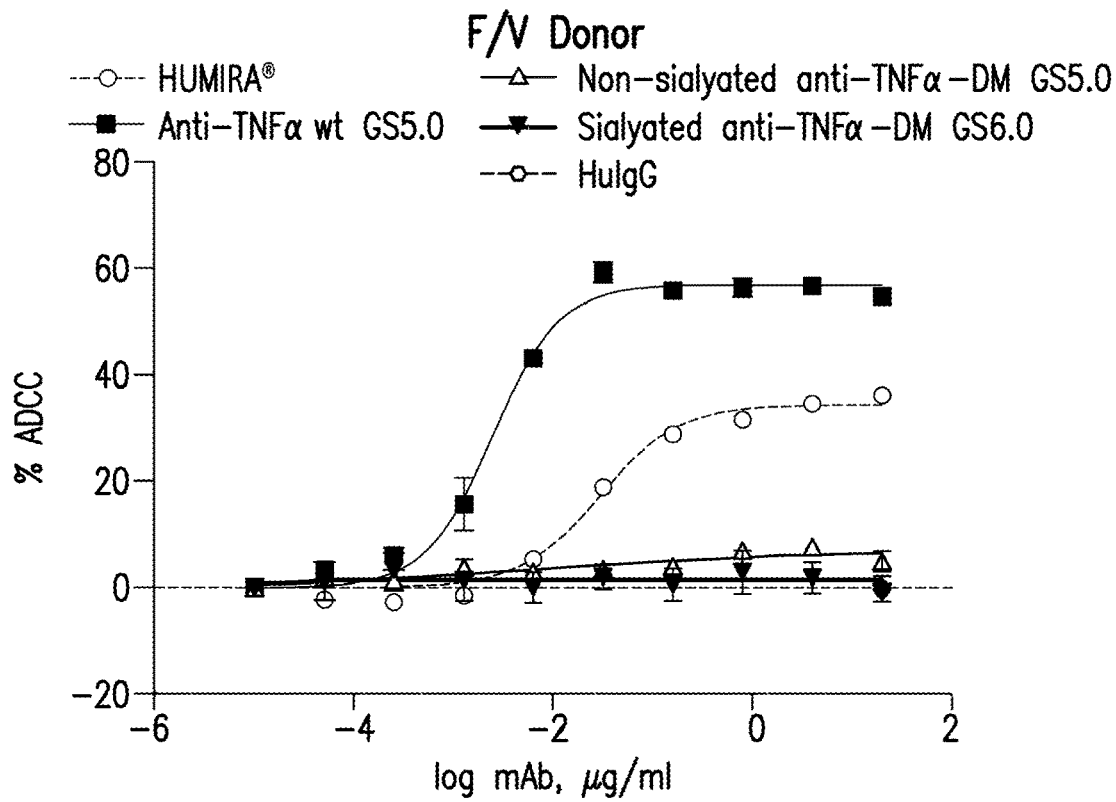
FIGS. 16A-16D are graphic representations of the ADCC response for the various antibodies produced by the materials and methods described in Example 18. HUMIRA® is the tradename for adalimumab.
Figure 16B:
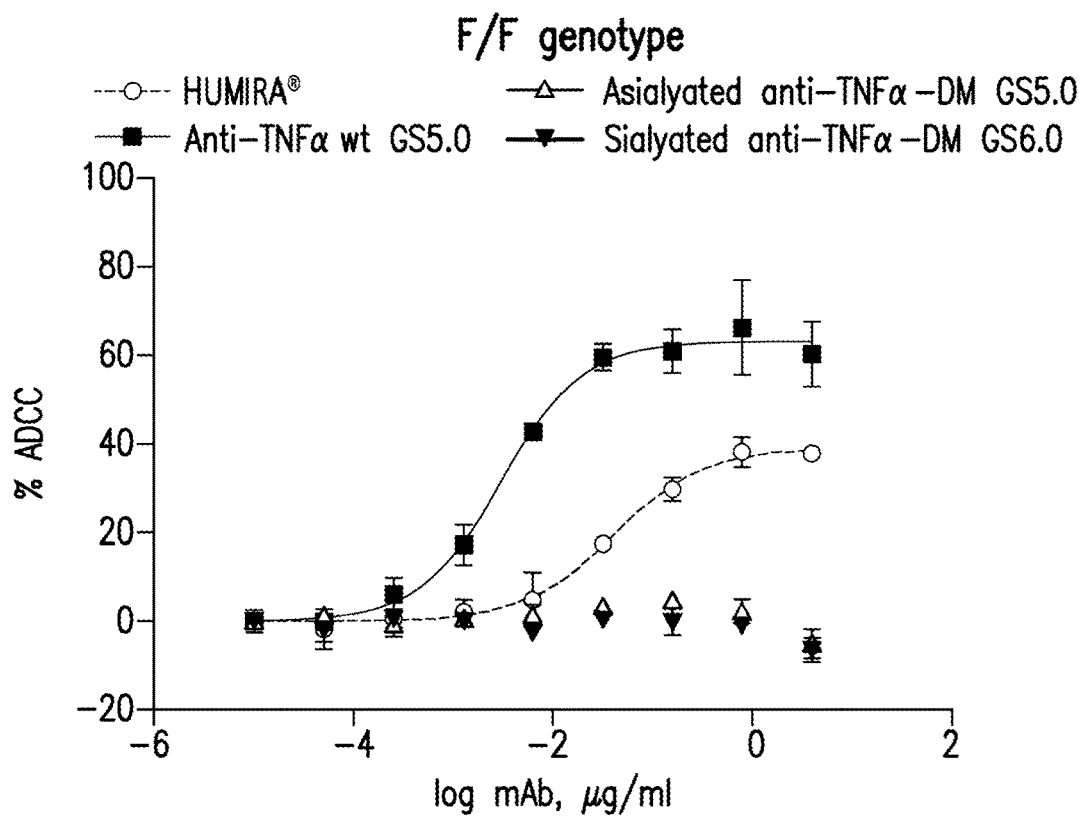
Figure 16C:
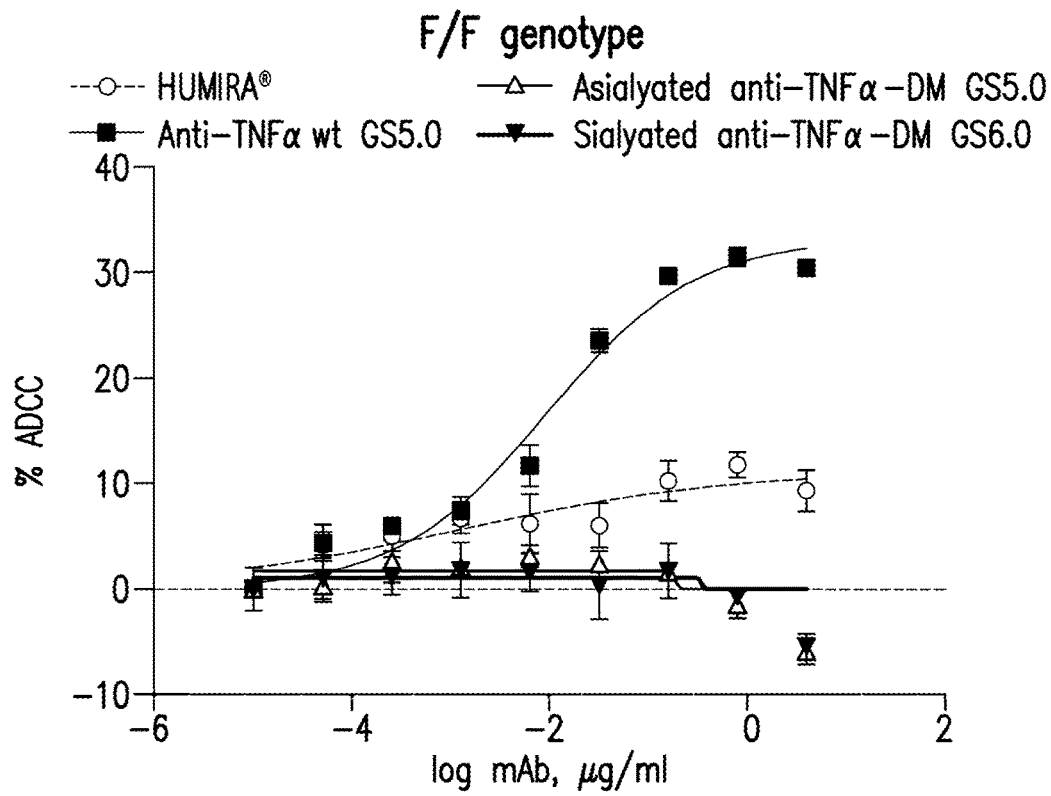
Figure 16D:
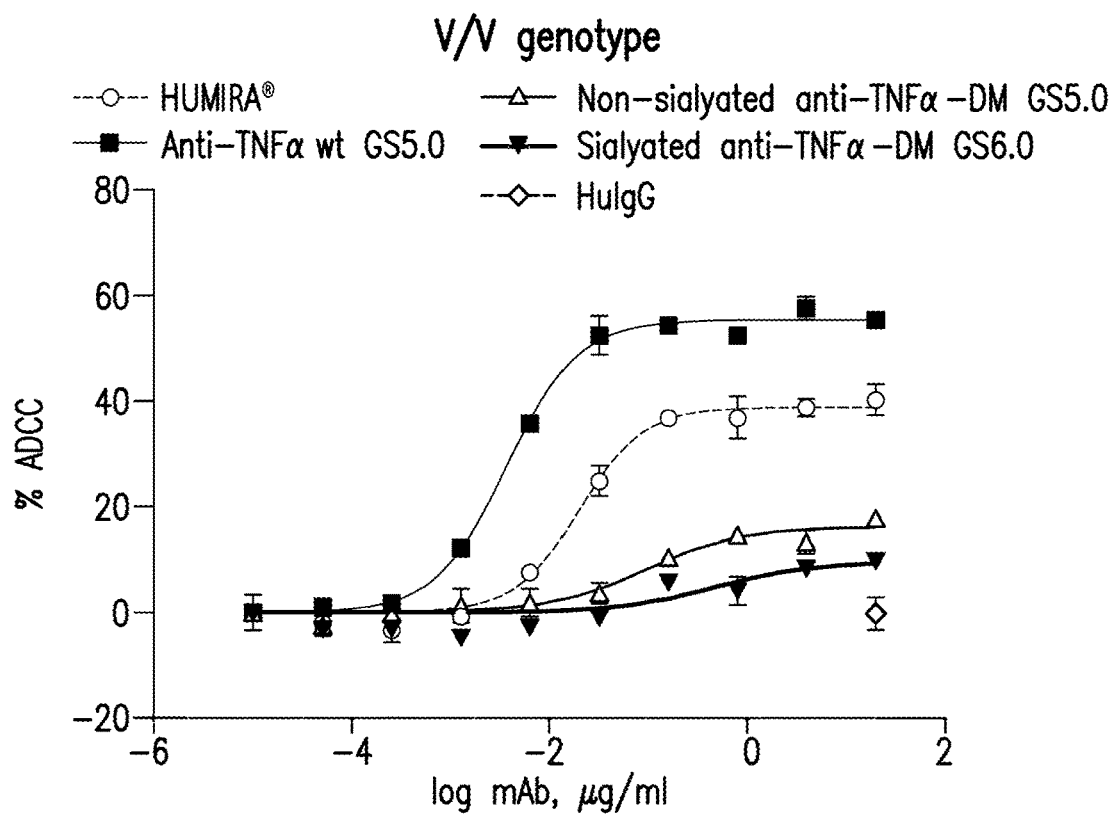

Applicants have surprisingly found that the Fc double mutein antibodies produced in *Pichia pastoris* by the materials and methods herein, when injected subcutaneously, had better bioavailability (absorption or exposure) than a comparable antibody produced in CHO cells by known commercial methods. In general, subcutaneous administration is preferable versus intravenous administration in that a subcutaneous formulation may be self-administered by the patient. As shown in FIG. 12, the serum concentrations from mice treated (as set forth in Example 14) with an Fc double mutein antibody increased about 30% as compared to serum concentrations for a CHO produced counterpart and was greater than that for an antibody produced in *Pichia pastoris* lacking the increased α 2,6-linked sialylated form.

Production of Human Glycosylated Antibodies Having Increased Levels of Sialylation As a result of the findings herein, Applicants have developed a method of producing antibodies in that have increased α 2,6-linked sialylation through the modification of the Fc region of the antibody such that a strain is created that can produce in vivo antibodies that have increased galactosylation and sialylation at position Asn297. Without wishing to be bound by any theory, Applicants propose that the lack of sialic acid and the low level of galactose present on the N-glycan at position Asn 297 of an antibody is due, not to a low efficiency of the respective glycosyl transferase, but rather to the steric hindrance inherent in the structure of the Fc region. Applicants believe that the structure of the Fc region prevents the addition of galactose and sialic acid during the short period of time when the antibody passes through the secretory pathway. Previous reports have suggested that high levels of galactosylation of a CD20 mAb was possible in vitro when longer incubation times than would typically be used in vivo are used in conjunction with galactosyltransferase Li et al., Nat. Biotechnol. 24(2): 210-215 (2006). It was thought that galactose transfer occurred when the antibody was in an open configuration with less steric hindrance. Structural or conformational changes resulting from the double mutation, i.e. double Fc mutein, result in a permanently open conformation allowing for greatly increased galactose and sialic acid transfer.

From Applicants studies herein, it appears that the individual mutation of amino acid F243 or V264 had a similar impact on increasing galactosylation and sialylation of the Fc region of an IgG1 molecule. Lund et al., J. Immunology 157(11): 4963-4969 (1996) reported a moderate increase of sialylated IgG3 produced in a CHO-K1 cell line by altering single amino acids in the Fc region, Phe241, Phe243, Val264, Aps265 or Tyr296 resulting in levels of 12-42% monosialylated and 4-31% bisialylated form. As reported herein, the antibodies produced by the materials and methods herein had a significant increase in sialylation when the specific sites, F243 or V264, were altered to alanine. Moreover, α 2,6-sialylated species levels in excess of 91% were achieved when both sites were simultaneously mutated (Table 3).

Biological Targets

It should be noted that while, in the examples that follow, Applicants exemplify the materials and methods of the invention using IgG1 antibodies having sequences similar to those for commercially available anti-Her2 and anti-TNF antibodies, the invention is not limited to the disclosed antibodies. Those of ordinary skill in the art would recognize and appreciate that the materials and methods herein could be used to produce any Fc-containing polypeptide for which the characteristics of enhanced anti-inflammatory activity or decreased effector function would be desirable. It should further be noted that there is no restriction as to the type of Fc-containing polypeptide or antibody so produced by the invention. The Fc region of the Fc-containing polypeptide could be from an IgA, IgD, IgE, IgG or IgM. In one embodiment, the Fc region of the Fc-containing polypeptide is from an IgG, including IgG1, IgG2, IgG3 or IgG4. In one embodiment, Fc region of the Fc-containing polypeptide is from an IgG1. In specific embodiments the antibodies or antibody fragments produced by the materials and methods herein can be humanized, chimeric or human antibodies.

In some embodiments, the Fc-containing polypeptides of the invention will bind to a biological target that is involved in inflammation.

In some embodiments, the Fc-containing polypeptide of the invention will bind to a pro-inflammatory cytokine. In some embodiments, the Fc-containing polypeptide of the invention will bind to a molecule selected from the group consisting of: TNF-α, IL-1, IL-2, IL-4, IL-5, IL-6, IL-8, IL-9, IL-10, IL-12, IL-15, IL-17, IL-18, IL-20, IL-21, IL-22, IL-23, IL-23R, IL-25, IL-27, IL-33, CD2, CD4, CD11A, CD14, CD18, CD19, CD23, CD25, CD40, CD40L, CD20, CD52, CD64, CD80, CD147, CD200, CD200R, TSLP, TSLPR, PD-1, PDL1, CTLA4, VLA-4, VEGF, PCSK9, α4β7-integrin, E-selectin, Fact II, ICAM-3, beta2-integrin, IFNγ, C5, CBL, LCAT, CR3, MDL-1, GITR, ADDL, CGRP, TRKA, IGF1R, RANKL, GTC, aBLys, or the receptor for any of the above mentioned molecules. In one embodiment, the Fc-containing polypeptide of the invention will bind to TNF-α. In another embodiment, the Fc-containing polypeptide of the invention will bind to Her2. In another embodiment, the Fc-containing polypeptide of the invention will bind to PCSK9. In another embodiment, the Fc-containing polypeptide of the invention will bind to TNFR. In another embodiment, the Fc-containing polypeptide of the invention will bind to LCAT. In another embodiment, the Fc-containing polypeptide of the invention will bind to TSLP. In another embodiment, the Fc-containing polypeptide of the invention will bind to PD-1. In another embodiment, the Fc-containing polypeptide of the invention will bind to IL-23.

In some embodiments, the Fc-containing polypeptides of the invention will be specific for an antigen selected from autoimmune antigens, allergens, MHC molecules or Rhesus factor D antigen. See, e.g., the antigens listed in Table 1 of WO2010/10910, which is incorporated herein by reference.

Methods of Increasing Anti-Inflammatory Properties or Decreasing Effector Function/Cytotoxicity The invention also comprises a method of increasing the anti-inflammatory properties of an Fc-containing polypeptide comprising: selecting a parent Fc-containing polypeptide that is useful in treating an inflammatory condition (for example, an antibody or immunoadhesin that binds to an antigen that is involved in inflammation) and introducing mutations at positions 243 and 264 of the Fc-containing polypeptide, wherein the numbering is according to the EU index as in Kabat, wherein the Fc-containing polypeptide has increased anti-inflammatory properties when compared to the parent Fc-containing polypeptide. In a embodiment, the Fc-containing polypeptide comprises mutations F243A and V264A. In another embodiment, the Fc-containing polypeptide comprises mutations F243Y and V264G. In another embodiment, the Fc-containing polypeptide comprises mutations F243T and V264G. In another embodiment, the Fc-containing polypeptide comprises mutations F243L and V264A. In another embodiment, the Fc-containing polypeptide comprises mutations F243L and V264N. In another embodiment, the Fc-containing polypeptide comprises mutations F243V and V264G. In one embodiment, the parent Fc-containing polypeptide is an antibody, antibody fragment or immunoadhesin that binds to an antigen that is involved in inflammation. In one embodiment, the parent Fc-containing polypeptide is an antibody, antibody fragment or immunoadhesin that is already marketed or under development for the treatment of an inflammatory conditions. In another embodiment, the parent Fc-containing polypeptide is an antibody selected from the group consisting of: Muromonab-CD3 (anti-CD3 receptor antibody), Abciximab (anti-CD41 7E3 antibody), Rituximab (anti-CD20 antibody), Daclizumab (anti-CD25 antibody), Basiliximab (anti-CD25 antibody), Palivizumab (anti-RSV (respiratory syncytial virus) antibody), Infliximab (anti-TNFα antibody), Trastuzumab (anti-Her2 antibody), Gemtuzumab ozogamicin (anti-CD33 antibody), Alemtuzumab (anti-CD52 antibody), Ibritumomab tiuxeten (anti-CD20 antibody), Adalimumab (anti-TNFα antibody), Omalizumab (anti-IgE antibody), Tositumomab-131I (iodinated derivative of an anti-CD20 antibody), Efalizumab (anti-CD11a antibody), Cetuximab (anti-EGF receptor antibody), Golimumab (anti-TNFα antibody), Bevacizumab (anti VEGF-A antibody), Natalizumab (anti α4 integrin), Efalizumab (anti CD11a), Cetolizumab (anti-TNFα antibody), Tocilizumab (anti-IL-6R), Ustenkinumab (anti IL-12/23), alemtuzumab (anti CD52), and natalizumab (anti α4 integrin), and variants thereof. In another embodiment, the parent Fc-containing polypeptide is an Fc-fusion protein selected from the group consisting of: ARCALYST®/rilonacept (IL1R-Fc fusion), ORENCIA®/abatacept (CTLA-4-Fc fusion), AMEVIVE®/alefacept (LFA-3-Fc fusion), Anakinra-Fc fusion (IL-1Ra-Fc fusion protein), etanercept (TNFR-Fc fusion protein), FGF-21-Fc fusion protein, GLP-1-Fc fusion protein, RAGE-Fc fusion protein, ActRIIA-Fc fusion protein, ActRIIB-Fc fusion protein, glucagon-Fc fusion protein, oxyntomodulin-Fc-fusion protein, GM-CSF-Fc fusion protein, EPO-Fc fusion protein, Insulin-Fc fusion protein, proinsulin-Fc fusion protein and insulin precursor-Fc fusion protein, and analogs and variants thereof.

The invention also comprises a method of reducing the effector function of an Fc-containing polypeptide, comprising introducing mutations at positions 243 and 264 of a parent Fc-containing polypeptide, wherein said Fc containing polypeptide has decreased effector function when compared to the parent Fc-containing polypeptide, wherein the numbering is according to the EU index as in Kabat. In one embodiment, the Fc-containing polypeptide comprises mutations F243A and V264A. In one embodiment, the Fc-containing polypeptide is an antibody or antigen binding fragment thereof. In one embodiment, the effector function is ADCC. In another embodiment, the effector function is CDC.

The invention also comprises a method of decreasing cytotoxicity of an Fc-containing polypeptide comprising: selecting a parent Fc-containing polypeptide that is useful in treating an inflammatory condition (for example, an antibody or immunoadhesin that binds to an antigen that is involved in inflammation) that binds to an antigen that is involved in inflammation and introducing mutations at positions 243 and 264 of the Fc-containing polypeptide, wherein the numbering is according to the EU index as in Kabat, wherein the Fc-containing polypeptide has decreased cytotoxicity when compared to the parent Fc-containing polypeptide.

In one embodiment, the parent Fc-containing polypeptide comprises a native Fc region. In another embodiment, the parent Fc-containing polypeptide comprises a F243A mutation. In another embodiment, the parent Fc-containing polypeptide comprises a V264A mutation.

Methods of Treatment

The invention also comprises a method of treating an inflammatory condition in a subject in need thereof comprising: administering to the subject a therapeutically effective amount of an Fc-containing polypeptide comprising mutations at positions 243 and 264, wherein the numbering is according to the EU index as in Kabat. In one embodiment, the Fc-containing polypeptide comprises mutations F243A and V264A. In another embodiment, the Fc-containing polypeptide comprises mutations F243Y and V264G. In another embodiment, the Fc-containing polypeptide comprises mutations F243T and V264G. In another embodiment, the Fc-containing polypeptide comprises mutations F243L and V264A. In another embodiment, the Fc-containing polypeptide comprises mutations F243L and V264N. In another embodiment, the Fc-containing polypeptide comprises mutations F243V and V264G. The Fc-containing polypeptide of the invention can be administered by any route. In one embodiment, the Fc-containing polypeptide is administered parenterally. In one embodiment, the Fc-containing polypeptide is administered subcutaneously.

In one embodiment, the inflammatory condition is unwanted inflammatory immune reactions.

In one embodiment, the inflammatory condition is an autoimmune disease. In one embodiment, the inflammatory condition will be multiple sclerosis. In one embodiment, the inflammatory condition is systemic lupus erythematosus. In one embodiment, the inflammatory condition is type I diabetes.

In one embodiment, the inflammatory condition is a primary immunodeficiency syndrome, including congenital agammaglobulinaemia and hypogammaglobulinaemia, common variable immunodeficiency, severed combined immunodeficiency, or Wiskott Aldrich syndrome.

In one embodiment, the inflammatory condition is a secondary immunodeficiency syndrome, including B-cell lymphocytic leukemia, HIV infection or an allogeneic bone marrow transplantation.

In one embodiment, the inflammatory condition is idiopathic thrombocytopenic purpura.

In one embodiment, the inflammatory condition is multiple myeloma.

In one embodiment, the inflammatory condition is Guillain-Barre syndrome.

In one embodiment, the inflammatory condition is Kawasaki disease.

In one embodiment, the inflammatory condition is chronic inflammatory demyelinating polyneuropathy (CIDP).

In one embodiment, the inflammatory condition is autoimmune neutropenia.

In one embodiment, the inflammatory condition is hemolytic anemia.

In one embodiment, the inflammatory condition is anti-Factor VIII autoimmune disease.

In one embodiment, the inflammatory condition is multifocal neuropathy.

In one embodiment, the inflammatory condition is systemic vasculitis (ANCA positive).

In one embodiment, the inflammatory condition is polymyositis.

In one embodiment, the inflammatory condition is dermatomyositis.

In one embodiment, the inflammatory condition is antiphospholipid syndrome.

In one embodiment, the inflammatory condition is sepsis syndrome.

In one embodiment, the inflammatory condition is graft-v-host disease.

In one embodiment, the inflammatory condition is allergy.

In one embodiment, the inflammatory condition is an anti-Rhesus factor D reaction.

In one embodiment, the inflammatory condition is an inflammatory condition of the cardiovascular system. The Fc-containing polypeptides of the invention may be used to treat atherosclerosis, atherothrombosis, coronary artery hypertension, acute coronary syndrome and heart failure, all of which are associated with inflammation.

In one embodiment, the inflammatory condition is an inflammatory condition of the central nervous system. In another embodiment, the inflammatory condition will be an inflammatory condition of the peripheral nervous system. For example, the Fc-containing polypeptides of the invention may be used for the treatment of, e.g., Alzheimer's disease, amyotrophic lateral sclerosis (a.k.a. ALS; Lou Gehrig's disease), ischemic brain injury, prion diseases, and HIV-associated dementia.

In one embodiment, the inflammatory condition is an inflammatory condition of the gastrointestinal tract. For example, the Fc-containing polypeptides of the invention may be used for treating inflammatory bowel disorders, e.g., Crohn's disease, ulcerative colitis, celiac disease, and irritable bowel syndrome.

In one embodiment, the inflammatory condition is psoriasis, atopic dermatitis, arthritis, including rheumatoid arthritis, osteoarthritis, and psoriatic arthritis.

In one embodiment, the inflammatory condition is steroid-dependent atopic dermatitis.

In one embodiment, the inflammatory condition is cachexia.

Examples of other inflammatory disorders that can be treated using the Fc-containing polypeptides of the invention also include: acne vulgaris, asthma, autoimmune diseases, chronic prostatitis, glomerulonephritis, hypersensitivities, pelvic inflammatory disease, reperfusion injury, sarcoidosis, transplant rejection, vasculitis, interstitial cystitis and myopathies.

In one embodiment, the Fc-containing polypeptide of the invention will be administered a dose of between 1 to 100 milligrams per kilograms of body weight. In one embodiment, the Fc-containing polypeptide of the invention will be administered a dose of between 0.001 to 10 milligrams per kilograms of body weight. In one embodiment, the Fc-containing polypeptide of the invention will be administered a dose of between 0.001 to 0.1 milligrams per kilograms of body weight. In one embodiment, the Fc-containing polypeptide of the invention will be administered a dose of between 0.001 to 0.01 milligrams per kilograms of body weight.

Pharmaceutical Formulations

The invention also comprises pharmaceutical formulations comprising an Fc-containing polypeptide of the invention and a pharmaceutically acceptable carrier.

In one embodiment, the invention relates a pharmaceutical composition comprising an Fc-containing polypeptide, wherein at least 70% of the N-glycans on the Fc-containing polypeptide comprise an oligosaccharide structure selected from the group consisting of $NANA_{(1-4)}Gal_{(1-4)}GlcNAc_{(2-4)}Man_3GlcNAc_2$, wherein the Fc-containing polypeptide comprises mutations at amino acid positions 243 and 264 of the Fc region, wherein the numbering is according to the EU index as in Kabat. In one embodiment, the mutations are F243A and V264A. In one embodiment, at least 47 mole % of the N-glycans have the structure $NANA_2Gal_2GlcNAc_2Man_3GlcNAc_2$. In one embodiment, the sialic acid residues in the sialylated N-glycans are attached via an α-2,6 linkage. In one embodiment, the sialic acid residues in the sialylated N-glycans are attached via an α-2,6 linkage and there is no detectable level of an α-2,3 linked sialic acid. In one embodiment, the sialylated N-glycans will comprise no N-glycolylneuraminic acid (NGNA).

As utilized herein, the term "pharmaceutically acceptable" means a non-toxic material that does not interfere with the effectiveness of the biological activity of the active ingredient(s), approved by a regulatory agency of the Federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils. The characteristics of the carrier will depend on the route of administration.

Pharmaceutical Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman et al. (2001) Goodman and Gilman's The Pharmacological Basis of Therapeutics, McGraw-Hill, New York, NY; Gennaro (2000), Remington: The Science and Practice of Pharmacy Lippincott, Williams, and Wilkins, New York, NY; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, NY).

The mode of administration can vary. Suitable routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial.

In certain embodiments, the Fc-containing polypeptides of the invention can be administered by an invasive route such as by injection (see above). In some embodiments of the invention, the Fc-containing polypeptides of the invention, or pharmaceutical composition thereof, is administered intravenously, subcutaneously, intramuscularly, intraarterially, intra-articularly (e.g. in arthritis joints), intratumorally, or by inhalation, aerosol delivery. Administration by non-invasive routes (e.g., orally; for example, in a pill, capsule or tablet) is also within the scope of the present invention.

In certain embodiments, the Fc-containing polypeptides of the invention can be administered by an invasive route such as by injection (see above). In some embodiments of the invention, the Fc-containing polypeptides of the invention, or pharmaceutical composition thereof, is administered intravenously, subcutaneously, intramuscularly, intraarterially, intra-articularly (e.g. in arthritis joints), intratumorally, or by inhalation, aerosol delivery. Administration by non-invasive routes (e.g., orally; for example, in a pill, capsule or tablet) is also within the scope of the present invention.

Compositions can be administered with medical devices known in the art. For example, a pharmaceutical composition of the invention can be administered by injection with a hypodermic needle, including, e.g., a prefilled syringe or autoinjector.

The pharmaceutical compositions of the invention may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556.

The pharmaceutical compositions of the invention may also be administered by infusion. Examples of well-known implants and modules form administering pharmaceutical compositions include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art.

Alternately, one may administer the antibody in a local rather than systemic manner, for example, via injection of the antibody directly into an arthritic joint, often in a depot or sustained release formulation. Furthermore, one may administer the antibody in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

The administration regimen depends on several factors, including the serum or tissue turnover rate of the therapeutic antibody, the level of symptoms, the immunogenicity of the therapeutic antibody, and the accessibility of the target cells in the biological matrix. Preferably, the administration regimen delivers sufficient therapeutic antibody to effect improvement in the target disease state, while simultaneously minimizing undesired side effects. Accordingly, the amount of biologic delivered depends in part on the particular therapeutic antibody and the severity of the condition being treated. Guidance in selecting appropriate doses of therapeutic antibodies is available (see, e.g., Wawrzynczak (1996) Antibody Therapy, Bios Scientific Pub. Ltd, Oxfordshire, UK; Kresina (ed.) (1991) Monoclonal Antibodies, Cytokines and Arthritis, Marcel Dekker, New York, NY; Bach (ed.) (1993) Monoclonal Antibodies and Peptide Therapy in Autoimmune Diseases, Marcel Dekker, New York, NY; Baert, et al. (2003) New Engl. J. Med. 348:601-608; Milgrom et al. (1999) New Engl. J. Med. 341:1966-1973; Slamon et al. (2001) New Engl. J. Med. 344:783-792; Beniaminovitz et al. (2000) New Engl. J. Med. 342:613-619; Ghosh et al. (2003) New Engl. J. Med. 348:24-32; Lipsky et al. (2000) New Engl. J. Med. 343:1594-1602).

Determination of the appropriate dose is made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. Preferably, a biologic that will be used is derived from the same species as the animal targeted for treatment, thereby minimizing any immune response to the reagent. In the case of human subjects, for example, chimeric, humanized and fully human Fc-containing polypeptides are preferred.

Fc-containing polypeptides can be provided by continuous infusion, or by doses administered, e.g., daily, 1-7 times per week, weekly, bi-weekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. A total weekly dose is generally at least 0.05 µg/kg body weight, more generally at least 0.2 µg/kg, 0.5 µg/kg, 1 µg/kg, 10 µg/kg, 100 µg/kg, 0.25 mg/kg, 1.0 mg/kg, 2.0 mg/kg, 5.0 mg/ml, 10 mg/kg, 25 mg/kg, 50 mg/kg or more (see, e.g., Yang et al., New Engl. J. Med. 349:427-434 (2003); Herold et al., New Engl. J. Med. 346:1692-1698 (2002); Liu et al., J. Neurol. Neurosurg. Psych. 67:451-456 (1999); Portielji et al., Cancer Immunol. Immunother. 52:133-144 (2003). In other embodiments, an Fc-containing polypeptide Of the present invention is administered subcutaneously or intravenously, on a weekly, biweekly, "every 4 weeks," monthly, bimonthly, or quarterly basis at 10, 20, 50, 80, 100, 200, 500, 1000 or 2500 mg/subject.

As used herein, the terms "therapeutically effective amount", "therapeutically effective dose" and "effective amount" refer to an amount of an Fc-containing polypeptide of the invention that, when administered alone or in combination with an additional therapeutic agent to a cell, tissue, or subject, is effective to cause a measurable improvement in one or more symptoms of a disease or condition or the progression of such disease or condition. A therapeutically effective dose further refers to that amount of the Fc-containing polypeptide sufficient to result in at least partial amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity.

Example 1

Strains and Reagents

*Escherichia coli* strains TOP10 or DH5α (Invitrogen, CA) were used for recombinant DNA work. Restriction endonucleases, DNA modification enzymes and PNGase F were obtained from New England Biolabs, Ipswich, MA. Oligonucleotides were ordered from Integrated DNA Technologies, Coralville, IA.

Example 2

Construction of Anti-Her 2 IgG1 Fc Muteins and *Pichia pastoris* Recombinant Expression Vector The preparation of single and double Fc muteins of Her2 IgG1 monoclonal antibody in *Pichia pastoris* was carried out using the sequences and protocols listed below.

A. Heavy and Light Chains

The heavy and light chain sequences, SEQ ID NOS: 1 and 2, respectively, used for the preparation of the Her2 monoclonal IgG1 antibody are as set forth below. The amino acid sequence of the heavy chain anti-Her2 double mutein antibody is shown in SEQ ID NO:9. The heavy and light chains were codon optimized according to *Pichia pastoris* codon usage and synthesized by GeneArt AG (Josef-Engert-Str. 11, D-93053 Regensburg, Germany) and cloned into pUC19.

The alanine Fc mutations at amino acid position F243 were carried out using a QuikChange® Site-Directed Mutagenesis Kit (Strategene, CA) using the forward and reverse primers, FcF243A-F (SEQ ID NO: 3) and FcF243A-R (SEQ ID NO: 4), respectively. Similarly, mutations at amino acid position V264 were carried out using the forward and reverse primers, V254A-F (SEQ ID NO: 5) and V264A-R (SEQ ID NO: 6), respectively. The double mutation was carried out through the use of enzymatic digestion between the F243A and V264A sites from each of the single mutein plasmids followed by ligation.

B. Signal Sequence

The signal sequence of an a-Mating Factor predomain was fused in frame to the 5' end of the light or heavy chain by PCR fusion. The sequence was codon optimized as described above. A Kozak sequence AAACG was added to the 5' end of the methionine and an EcoR1 site was added before the Kozak sequence for cloning purposes. The DNA sequence (SEQ ID NO: 7) and amino acid (SEQ ID NO: 8) translation are as shown below.

C. Recombinant Plasmids for Expression IgG1 and IgG1 Fc Muteins

The heavy and light chains with the fused signal sequence of IgG1 and its muteins were cloned under *Pichia pastoris* AOX1 promoter and in front of *S. cerevisiae* Cyc terminator, respectively. The expression cassette of the completed heavy and light chains was put together into the final expression vector. Genomic insertion into *Pichia pastoris* was achieved by linearization of the vector with SpeI and targeted integration into the Trp2 site.

A summary of the plasmids used herein is given below in Table 1. A graphic representation of the final expression plasmid for the Her2 double Fc mutein is set forth in FIG. 1.

TABLE 1

| Plasmid | Description |
| --- | --- |
| pGLY2336 | pCR2.1 topo with WT light chain with alpha-MF pre signal sequence and Kozak sequence |
| pGLY2337 | pCR2.1 topo with WT heavy chain with alpha-MF pre signal sequence and Kozak sequence |
| pGLY2338 | WT light chain expression vector |
| pGLY2987 | WT heavy chain expression vector |
| pGLY2988 | WT IgG1 expression final vector having both heavy and light chain |
| pGLY3067 | pCR2.1 topo vector with IgG1 heavy chain F243A mutation |
| pGLY3473 | pCR2.1 topo vector with IgG1 heavy chain V264A mutation |
| pGLY3474 | F243A mutein expression vector |
| pGLY3475 | V264A mutein expression vector |
| pGLY3479 | F243 and V264A double mutein expression vector |
| pGLY3481 | pGLY3474(BmHI/NotI) + pGLY2338(BglII/Not) F243A mutant with 1 copy Light chain |
| pGLY3482 | pGLY3475(BmHI/NotI) + pGLY2338(BglII/Not) V264A mutant with 1 copy Light chain |
| pGLY3483 | F243A and V264A double mutations final expression vector with both heavy and light chain |

Example 3

Glycoengineered *Pichia* GFI5.0 and GFI6.0 Hosts for Producing Anti-Her2 and its Fc Muteins Two different glycoengineered *Pichia* hosts were applied in this invention, GFI5.0 and GFI 6.0. Following the procedures disclosed in Gerngross, U.S. Pat. No. 7,029,872 and Gerngross, U.S. Pat. No. 7,449,308, one can construct vectors that are useful for genetically engineering lower eukaryotic host cells such that they are capable of expressing a desired polypeptide having a desired N-glycoform as the predominant species. GFI 5.0 and GFI6.0 strains were engineered from NRRL11430 (American Type Culture Collection (ATCC®), P.O. Box 1549, Manassas, VA 20108, USA) according to the methods described in Hamilton et al., Science, 313: 1441-1443 (2006) and Hamilton US 2006/0286637. The engineered *Pichia pastoris* strain GFI5.0 is capable of producing proteins with a biantennary N-glycan structure with terminal galactose. The genotype of the GFI5.0 strain used herein, RDP697, is as follows: ura5Δ:: ScSUC2 och1Δ::lacZ bmt2Δ::lacZ/KlMNN2-2 mnn4L1Δ:: lacZ/MmSLC35A3 pno1Δ::lacZ ADE1::lacZ/FB8/NA10/ MmSLC35A3 his1::lacZ-URA5-lacZ/XB33/SpGALE/ DmUGT arg1::HIS1/KD53/TC54. The genotype of the engineered *Pichia pastoris* strain GFI 6.0, YGLY3582, is as follows: ura5Δ::ScSUC2 och1Δ::lacZ, bmt2Δ::lacZ/ KlMNN2-2 mnn4LIΔ::lacZ/MmSLC35A3, pno1Δmnn4Δ:: lacZ met16Δ::lacZ, his1Δ::lacZ/ScGAL10/XB33/DmUGT, arg1Δ::HIS1/KD53/TC54, ADE1::lacZ/NA10/ MmSLC35A3/FB8, PRO1::lacZ-URA5-lacZ/TrMDS1, TRP2:ARG1/MmCST/HsGNE/HsCSS/HsSPS/MmST6-33Y. The GFI 6.0 strain is capable of producing proteins with a biantennary N-glycan structure on which terminal α 2,6-linked sialic acid is attached to galactose.

The abbreviations used to describe the genotypes are commonly known and understood by those skilled in the art, and include the following abbreviations:

ScSUC2 *S. cerevisiae* Invertase

OCH1 Alpha-1,6-mannosyltransferase

KlMNN2-2 *K. lactis* UDP-GlcNAc transporter
BMT1 Beta-mannose-transfer (beta-mannose elimination)
BMT2 Beta-mannose-transfer (beta-mannose elimination)
BMT3 Beta-mannose-transfer (beta-mannose elimination)
BMT4 Beta-mannose-transfer (beta-mannose elimination)
MNN4L1 MNN4-like 1 (charge elimination)
MmSLC35A3 Mouse homologue of UDP-GlcNAc transporter
PNO1 Phosphomannosylation of N-glycans (charge elimination)
MNN4 Mannosyltransferase (charge elimination)
ScGAL10 UDP-glucose 4-epimerase
XB33 Truncated HsGalT1 fused to ScKRE2 leader
DmUGT UDP-Galactose transporter
KD53 Truncated DmMNSII fused to ScMNN2 leader
TC54 Truncated RnGNTII fused to ScMNN2 leader
NA10 Truncated HsGNTI fused to PpSEC12 leader
FB8 Truncated MmMNS1A fused to ScSEC12 leader
TrMD S1 Secreted *T. reseei* MNS1
ADE1 N-succinyl-5-aminoimidazole-4-carboxamide ribotide (SAICAR) synthetase
MmCST Mouse CMP-sialic acid transporter
HsGNE Human UDP-GlcNAc 2-epimerase/N-acetylmannosamine kinase
HsCSS Human CMP-sialic acid synthase
HsSPS Human N-acetylneuraminate-9-phosphate synthase
MmST6-33 Truncated Mouse alpha-2,6-sialyl transferase fused to ScKRE2 leader
LmSTT3d Catalytic subunit of oligosaccharyltransferase from *Leishmania major*

Example 4

Yeast Transformation and Screening

The glycoengineered GFI5.0 and GS6.0 strains were grown in YPD rich media (yeast extract 1%, peptone 2% and 2% dextrose), harvested in the logarithmic phase by centrifugation, and washed three times with ice-cold 1 M sorbitol. One to five µg of a SpeI digested plasmid was mixed with competent yeast cells and electroporated using a Bio-Rad Gene Pulser Xcell™ (Bio-Rad®, 2000 Alfred Nobel Drive, Hercules, CA 94547) preset *Pichia pastoris* electroporation program. After one hour in recovery rich media at 24° C., the cells were plated on a minimal dextrose media (1.34% YNB, 0.0004% biotin, 2% dextrose, 1.5% agar) plate containing 300 µg/ml Zeocin and incubated at 24° C. until the transformants appeared.

To screen for high titer strains, 96 transformants were inoculated in buffered glycerol-complex medium (BMGY) and grown for 72 hours followed by a 24 hour induction in buffered methanol-complex medium (BMMY). Secretion of antibody was assessed by a Protein A beads assay as follows. Fifty micro liter supernatant from 96 well plate cultures was diluted 1:1 with 50 mM TRIS pH 8.5 in a non-binding 96 well assay plate. For each 96 well plate, 2 ml of magnetic BioMag Protein A suspension beads (Qiagen, Valencia, CA) were placed in a tube held in a magnetic rack. After 2-3 minutes when the beads collected to the side of the tube, the buffer was decanted off. The beads were washed three times with a volume of wash buffer equal to the original volume (100 mM TRIS, 150 mM NaCl, pH 7.0) and resuspended in the same wash buffer. Twenty µl of beads were added to each well of the assay plate containing diluted samples. The plate was covered, vortexed gently and then incubated at room temperature for 1 hour, while vortexing every 15 minutes. Following incubation, the sample plate was placed on a magnetic plate inducing the beads to collect to one side of each well. On the Biomek NX Liquid Handler (Beckman Coulter, Fullerton, CA), the supernatant from the plate was removed to a waste container. The sample plate was then removed from the magnet and the beads were washed with 100 µl wash buffer. The plate was again placed on the magnet before the wash buffer was removed by aspiration. Twenty µl loading buffer (Invitrogen E-PAGE gel loading buffer containing 25 mM NEM (Pierce™, Rockford, IL)) was added to each well and the plate was vortexed briefly. Following centrifugation at 500 rpm on the Beckman ALLEGRA® 6 centrifuge, the samples were incubated at 99° C. for five minutes and then run on an E-PAGE high-throughput pre-cast gel (Invitrogen, Carlsbad, CA). Gels were covered with gel staining solution (0.5 g Coomassie G250 Brilliant Blue, 40% MeOH, 7.5% Acetic Acid), heated in a microwave for 35 seconds, and then incubated at room temperature for 30 minutes. The gels were de-stained in distilled water overnight. High titer colonies were selected for further Sixfors fermentation screening described in detail in Example 5. A summary of the IgG1 wild type (parent) and Fc mutein producing strains is given below in Table 2.

TABLE 2

| Strains | Genotype | Description |
| --- | --- | --- |
| YDX477 | ura5Δ::ScSUC2 och1Δ::lacZ bmt2Δ::lacZ/KlMNN2-2 mnn4L1Δ::lacZ/MmSLC35A3 pno1Δ::lacZ ADE1::lacZ/FB8/NA10/MmSLC35A3 his1::lacZ-URA5-lacZ/XB33/SpGALE/DmUGT arg1::HIS1/KD53/TC54 | GFI5.0 strain producing WT IgG1 |
| YDX551 | ura5Δ::ScSUC2 och1Δ::lacZ bmt2Δ::lacZ/KlMNN2-2 mnn4L1Δ::lacZ/MmSLC35A 3 pno1Δ::lacZ ADE1::lacZ/FB8/NA10/MmSLC35A3 his1::lacZ-URA5-lacZ/XB33/SpGALE/DmUGT arg1::HIS1/KD53/TC54 | GFI5.0 strain producing anti-Her2 Fc V264A mutein |
| YDX552 | ura5Δ::ScSUC2 och1Δ::lacZ bmt2Δ::lacZ/KlMNN2-2 mnn4L1Δ::lacZ/MmSLC35A3 pno1Δ::lacZ ADE1::lacZ/FB8/NA10/MmSLC35A3 his1::lacZ-URA5-lacZ/XB33/SpGALE/DmUGT arg1::HIS1/KD53/TC54 | GFI5.0 strain producing anti-Her2 Fc F243A mutein |
| YDX557 | ura5Δ::ScSUC2 och1Δ::lacZ bmt2Δ::lacZ/KlMNN2-2 mnn4L1Δ::lacZ/MmSLC35A3 pno1Δ:: lacZ ADE1::lacZ/FB8/NA10/MmSLC35A3 his1::lacZ-URA5-lacZ/XB33/SpGALE/DmUGT arg1::HIS1/KD53/TC54 | GFI5.0 strain producing anti-Her2 Fc F243A, V264A double mutein |

TABLE 2-continued

| Strains | Genotype | Description |
|---|---|---|
| YGLY4570 | ura5Δ::ScSUC2 och1Δ::lacZ, bmt2Δ::lacZ/KlMNN2-2 mnn4L1Δ::lacZ/MmSLC35A3, pno1Δmnn4Δ::lacZ met16Δ::lacZ, his1Δ::lacZ/ScGAL10/XB33/DmUGT, arg1Δ::HIS1/KD53/TC54, ADE1::lacZ/NA10/MmSLC35A3/FB8, PRO1::lacZ-URA5-lacZ/TrMDS1, TRP2:ARG1/MmCST/HsGNE/HsCSS/HsSPS/MmST6-33 | GFI6.0 strain making anti-Her2 Fc V264A mutein |
| YGLY4568 | ura5Δ::ScSUC2 och1Δ::lacZ, bmt2Δ::lacZ/KlMNN2-2 mnn4L1Δ::lacZ/MmSLC35A3, pno1Δmnn4Δ::lacZ met16Δ::lacZ, his1Δ::lacZ/ScGAL10/XB33/DmUGT, arg1Δ::HIS1/KD53/TC54, ADE1::lacZ/NA10/MmSLC35A3/FB8, PRO1::lacZ-URA5-lacZ/TrMDS1, TRP2:ARG1/MmCST/HsGNE/HsCSS/HsSPS/MmST6-33 | GFI6.0 strain making anti-Her2 Fc F243A mutein |
| YGLY4563 | ura5Δ::ScSUC2 och1Δ::lacZ, bmt2Δ::lacZ/KlMNN2-2 mnn4L1Δ::lacZ/MmSLC35A3, pno1Δmnn4Δ::lacZ met16Δ::lacZ, his1Δ::lacZ/ScGAL10/XB33/DmUGT, arg1Δs:HIS1/KD53/TC54, ADE1::lacZ/NA10/MmSLC35A3/FB8, PRO1::lacZ-URA5-lacZ/TrMDS1, TRP2:ARG1/MmCST/HsGNE/HsCSS/HsSPS/MmST6-33 | GFI6.0 strain making anti-Her2 F243A/V264A double mutein |

Example 5

Bioreactor (Sixfors) Screening

Bioreactor fermentation screening was conducted as described as follows: Fed-batch fermentations of glycoengineered *Pichia pastoris* were executed in 0.5 liter bioreactors (Sixfors multi-fermentation system, ATR Biotech, Laurel, MD) under the following conditions: pH 6.5, 24° C., 300 ml airflow/min, and an initial stirrer speed of 550 rpm with an initial working volume of 350 ml (330 ml BMGY medium [100 mM potassium phosphate, 10 g/l yeast extract, 20 g/l peptone (BD, Franklin Lakes, NJ), 40 g/l glycerol, 18.2 g/l sorbitol, 13.4 g/l YNB (BD, Franklin Lakes, NJ), 4 mg/l biotin] and 20 ml inoculum). IRIS multi-fermentor software (ATR Biotech, Laurel, MD) was used to increase the stirrer speed from 550 rpm to 1200 rpm linearly between hours 1 and 10 of the fermentation. Consequently, the dissolved oxygen concentration was allowed to fluctuate during the fermentation. The fermentation was executed in batch mode until the initial glycerol charge (40 g/1) was consumed (typically 18-24 hours). A second batch phase was initiated by the addition of 17 ml of a glycerol feed solution to the bioreactor (50% [w/w] glycerol, 5 mg/l biotin and 12.5 ml/1 PTM1 salts (65 g/l $FeSO_4 \cdot 7H_2O$, 20 g/l $ZnCl_2$, 9 g/l $H_2SO_4$, 6 g/l $CuSO_4 \cdot 5H_2O$, 5 g/l $H_2SO_4$, 3 g/l $MnSO_4 \cdot 7H_2O$, 500 mg/l $CoCl_2 \cdot 6H_2O$, 200 mg/l $NaMoO_4 \cdot 2H_2O$, 200 mg/l biotin, 80 mg/1 NaI, 20 mg/l $H_3BO_4$). The fermentation was again operated in batch mode until the added glycerol was consumed (typically 6-8 hours). The induction phase was initiated by feeding a methanol solution (100% [w/w] methanol, 5 mg/l biotin and 12.5 ml/l PTM1 salts) at 0.6 g/hr, typically for 36 hours prior to harvest. The entire volume was removed from the reactor and centrifuged in a Sorvall™ Evolution™ RC centrifuge equipped with a SLC-6000 rotor (Thermo Scientific, Milford, MA) for 30 minutes at 8,500 rpm. The cell mass was discarded and the supernatant retained for purification and analysis. Glycan quality is assessed by MALDI-Time-of-flight (TOF) spectrometry and 2-aminobenzidine (2-AB) labeling according to Li et al., Nat. Biotech. 24(2): 210-215 (2006). Glycans were released from the antibody by treatment with PNGase-F and analyzed by MALDI-TOF to confirm glycan structures. To quantitated the relative amounts of neutral and charged glycans present, the N-glycosidase F released glycans were labeled with 2-AB and analyzed by HPLC.

Example 6

Bioreactor Cultivations

Fermentations were carried out in 3 L (Applikon, Foster City, CA) and 15 L (Applikon, Foster City, CA) glass bioreactors and a 40 L (Applikon, Foster City, CA) stainless steel, steam in place bioreactor. Seed cultures were prepared by inoculating BMGY media directly with frozen stock vials at a 1% volumetric ratio. Seed flasks were incubated at 24° C. for 48 hours to obtain an optical density ($OD_{600}$) of 20±5 to ensure that cells are growing exponentially upon transfer. The cultivation medium contained 40 g glycerol, 18.2 g sorbitol, 2.3 g $K_2HPO_4$, 11.9 g $KH_2PO_4$, 10 g yeast extract (BD, Franklin Lakes, NJ), 20 g peptone (BD, Franklin Lakes, NJ), $4 \times 10^{-3}$ g biotin and 13.4 g Yeast Nitrogen Base (BD, Franklin Lakes, NJ) per liter. The bioreactor was inoculated with a 10% volumetric ratio of seed to initial media. Cultivations were done in fed-batch mode under the following conditions: temperature set at 24±0.5° C., pH controlled at to 6.5±0.1 with $NH_4OH$, dissolved oxygen was maintained at 1.7±0.1 mg/L by cascading agitation rate on the addition of $O_2$. The airflow rate was maintained at 0.7 vvm. After depletion of the initial charge glycerol (40 g/L), a 50% glycerol solution containing 12.5 mL/L of PTM1 salts was fed exponentially at 50% of the maximum growth rate for eight hours until 250 g/L of wet cell weight was reached. Induction was initiated after a thirty minute starvation phase when methanol was fed exponentially to maintain a specific growth rate of 0.01 $h^{-1}$. When an oxygen uptake rate of 150 mM/L/h was reached, the methanol feed rate was kept constant to avoid oxygen limitation.

Example 7

Antibody Purification

Purification of secreted antibody can be performed by one of ordinary skill in the art using available published methods, for example Li et al., Nat. Biotech. 24(2):210-215 (2006), in which antibodies are captured from the fermentation supernatant by Protein A affinity chromatography and further purified using hydrophobic interaction chromatography with a phenyl SEPHAROSE™ fast flow resin.

Example 8

MALDI-TOF Analysis of Glycans

N-glycans were analyzed as described in Choi et al., Proc. Natl. Acad. Sci. USA 100: 5022-5027 (2003) and Hamilton et al., Science 301: 1244-1246 (2003). After the glycoproteins were reduced and carboxymethylated, N-glycans were released by treatment with peptide-N-glycosidase F. The released oligosaccharides were recovered after precipitation of the protein with ethanol. Molecular weights were determined by using a Voyager PRO linear MALDI-TOF (Applied Biosystems) mass spectrometer with delayed extraction according to the manufacturer's instructions. The results of the N-glycan analysis of the anti-Her2 antibodies produced according to the Examples above are shown in FIGS. 4-8.

Example 9

N-Linked Glycan Analysis by HPLC

To quantify the relative amount of each glycoform, the N-glycosidase F released glycans were labeled with 2-aminobenzidine (2-AB) and analyzed by HPLC as described in Choi et al., Proc. Natl. Acad. Sci. USA 100: 5022-5027 (2003) and Hamilton et al., Science 313: 1441-1443 (2006). The amounts of sialylated anti-Her2 antibody produced in a GFI 6.0 strain for single and double muteins produced in 3 L bioreactors and for wild-type and double mutein produced in a small scale 0.5 L bioreactor is shown in Table 3.

TABLE 3

|  | Mono-sialylated | Bi-sialylated | Total sialylated |
| --- | --- | --- | --- |
| Wild-type | 10.4% | 0% | 10.4% |
| Single mutein V264A | 43% | 8% | 51% |
| Single mutein F243A | 23% | 7% | 30% |
| Double mutein F243A/V264A | 27% | 47% | 74% |
| Double mutein F243A/V264A (0.5 L bioreactor) | 25% | 66% | >91% |

Example 10

Antigen Affinity Assay

Mammalian cells expressing antigen were harvested by trypsinization, filtered through a 40 μm cell strainer, and suspended in 1% fetal bovine serum (FBS) in phosphate buffered saline (PBS) in a 96-deep-well plate. Serial dilutions of the purified antibody were added to the cells at final concentration ranging from 10 to 0.01 lag ml-1. The antibody cell mixture was incubated for 45 minutes on ice. The cells were washed in cold PBS and stained with 2 μg ml-1 of anti-human IgG ALEXA™ FLUOR 488 (Invitrogen, Carlsbad, CA) in 1% FBS in PBS for 45 min on ice in the dark. The cells were washed again in cold PBS, suspended in 1% FBS in PBS and transferred to a U-bottom 96-well plate (USA Scientific, Ocala, FL). Mean fluorescence intensity (MFI) was detected on a Guava® ExpressPlus™ (Millipore, Billerica, MA) using an excitation wavelength of 488 nm and an emission wavelength of 525 nm. The results are shown in FIG. 3.

Example 11

FcγR Binding Assay

Fcγ receptor binding assays were carried out as described in Shields et al., J. Biol. Chem. 276: 6591-6604 (2001) with minor modifications. High protein binding 96-well plates (Corning Costar, Lowell, MA) were coated with 100 μl per well of Fcγ receptor solutions in PBS at the following concentrations: 1 μg/ml for FcγRI (R & D Systems) and FcγRIIa (*Pichia pastoris* produced), 2 μg/ml for FcγRIIb/c (*P. pastoris* produced), 0.4 μg/ml for FcγRIIIa-V158, and 0.8 μg/ml for FcγRIIIa-F158 (both *P. pastoris* produced). FcγRIIIa-V158 and FcγRIIIa-F158 receptors were expressed using *P. pastoris* as described in Li et al., Nat. Biotech. 24:210-215(2006).

FcγRIIa was also expressed in glycoengineered *Pichia* using a similar method as described in Li et al. The FcγRIIa extracellular domain was PCR amplified from human cDNA and cloned into Pcr2.1 topo vector. The Fc gamma receptors were cloned into *Pichia* expression vector using *S. cerevisiae* alpha Mating Factor prepro domain and under AOX1 promoter. The final strain, Ygly4665, was generated by transforming Pgly3249 into Ygly638 (GFI2.0 host).

The FcγRIIb/c was expressed and produced using glycoengineered *Pichia* YGLY638 (GFI2.0 host). The DNA sequence of the extracellular domain of the human Fc gamma receptor Iib/c (NP_003992) carrying its C-terminal 9 His-tag was *Pichia* codon optimized, and designated Pas197 (GeneArt, Germany). The amino acid sequence of the histidine-tagged extracellular domain of the FcγRIIb/c can be found in SEQ ID NO:17. For the plasmid construction of Pgly3246, the codon-optimized hFcγRIIb/c (AfeI/KpnI) and *Saccharomyces cerevisiae* αMfprepro (EcoRI/blunt) were cloned into Pgly2219 at EcoRI and KpnI sites. The resulting plasmid Pgly3246 was transformed into Ygly638 to generate Ygly4653. YGLY4653 were fermented and purified according to Li et al.

For FcγR1, the antibody was coated in assay diluent (1% BSA, PBS, 0.05% TWEEN® 20) in monomeric form. For all other receptors, the antibody was coated after dimerization with alkaline phosphatase conjugated anti-human IgG F(ab')2 (Jackson ImmunoResearch, West Grove, PA) for one hour at room temperature. FcγRJ bound antibody was also detected using the F(ab')2 and all plates were quantified by measuring excitation at 340 nm and emission at 465 nm after an 18 hour incubation with SUPERPHOS® (Virolabs, Chantilly, VA).

The results are shown in FIG. 9. As shown in FIG. 9A, the Fc single muteins (▲ and ▼) had FcγRI (Fc receptor gamma-chain I, CD64) binding similar to both the Her2 antibody (■) (FIG. 9A) and the *Pichia pastoris* Her2 (data not shown), while the Fc double mutein (◆) had about a fourteen fold decrease in affinity to FcγRI (FIG. 9A).

For FcγRIIb/c, the Fc single muteins (▲ and ▼) demonstrated a ten fold decrease in receptor binding properties as compared to the Her2 antibody (■) (FIG. 9B), while the double Fc mutein does not appear to bind to FcγRIIb/c.

Figure 9D:
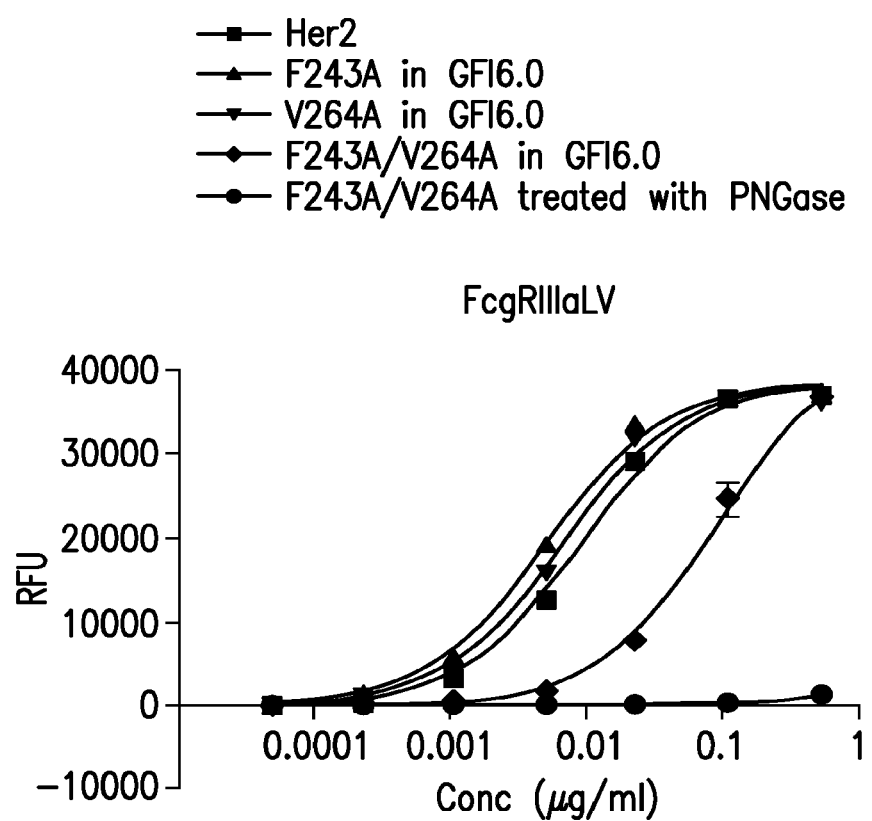

FcγRIIIa-F158 and FcγRIIIa-V158, both single Fc muteins (▲ and ▼) bind twenty fold better than the commercial HERCEPTIN® antibody (■) to FcγRIIIa-F158 (FIG. 9C), but bind FcγRIIIa-V158 only slightly better than the commercial HERCEPTIN® antibody (FIG. 9D). The Fc double mutein (◆) had little affinity (50 fold decrease) for FcγRIIIa-F158 (FIG. 9C) while still retaining some affinity for FcγRIIIa-V158, albeit thirty folder weaker than the commercial HERCEPTIN® antibody (■) and the *Pichia pastoris* Her2 antibody (data not shown) from GS5.0 (FIG. 9D).

Moreover, the affinity of the double Fc mutein for both polymorphisms of FcγRIIIa does not appear to change upon release of the sialic acid by neuraminidase (data not shown). Thus, without wishing to be bound by any theory, Applicants attribute the decrease in affinity for both polymorphisms of FcγRIIIa to structural or conformational changes resulting from the double mutation, i.e. double Fc mutein, and not due to the increased levels of the α 2,6-linked sialylated N-glycans.

Example 12

C1q Binding Assay for the Anti-Her2 Antibodies and its Fc Muteins

The C1q binding assay was conducted using the methods of Idusogie et al., J. Immunology 164: 4178-4184 (2000) as described. Serially diluted antibody was coated 100 μl per well in 50 Mm $Na_2HCO_3$ Ph9.0 to clear high binding plates. Human C1q complement (US Biological, Swampscott, MA) was coated at 2 μg/M1 in assay diluent (0.1% Bovine Gelatin, PBS, 0.05% TWEEN® 20) for two hours. C1q was detected with HRP conjugated sheep polyclonal anti-human C1q antibody (AbDSerotec) and quantified by measuring OD450.

Figure 10:
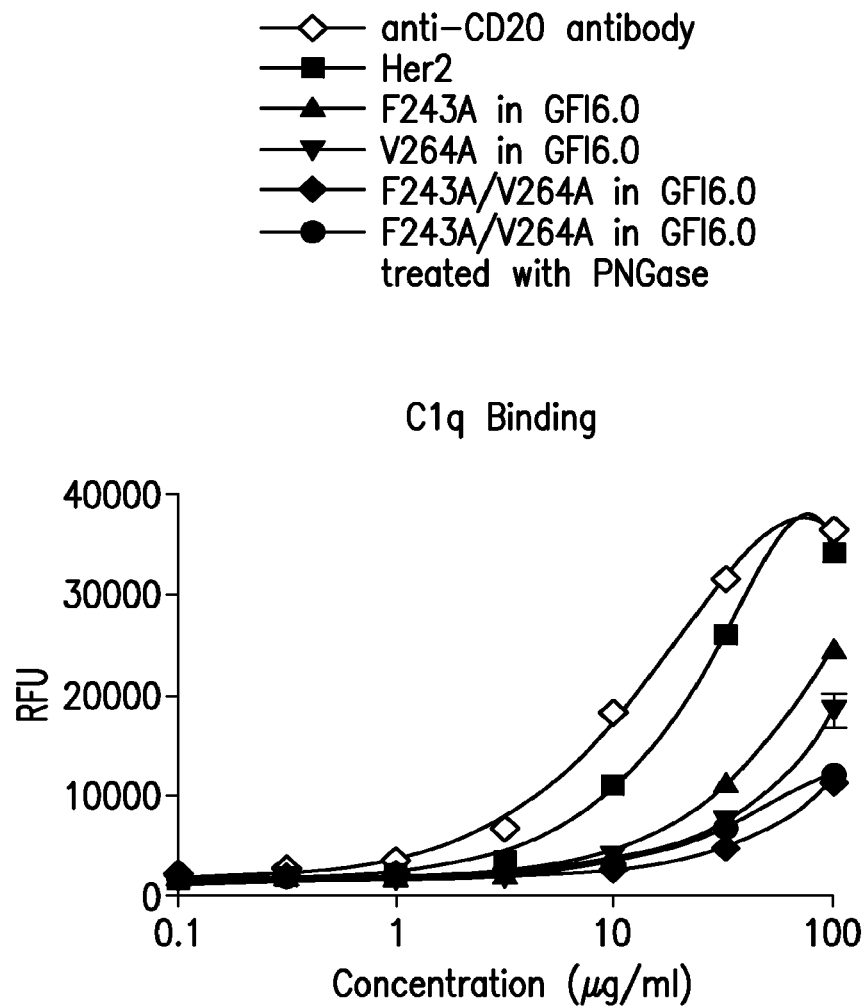
FIG. 10 is a graphic representation of the C1q binding for various antibodies produced by the materials and methods described in Example 12: ◇—anti-CD20 antibody, a positive control; ■—Her2; ▲—F243A produced with GS6.0 glycosylation; ▼—264A produced with GS6.0 glycosylation; ♦—F243A/V264A produced with GS6.0 glycosylation; ●—F243A/V264A with GS6.0 glycosylation and PNGase.

The results are shown in FIG. 10. As shown in FIG. 10, the single and double Fc mutein antibodies produced by the materials and methods described herein had decreased C1q binding relative to those produced in mammalian cell culture or non-sialylated *Pichia pastoris* strains. C1q binding for the antibodies produced from the single Fc muteins (▲ or ▼) were decreased 5-10 fold relative to the Her2 antibody while C1q binding for the double Fc mutein (♦) was virtually eliminated.

Both the *Pichia pastoris* Her2 antibody produced in a GFI5.0 strain (data not shown) and the Her2 antibody showed similar affinity to C1q.

Example 13

Antibody Dependent Cellular Toxicity for Anti-Her2 and its Fc Muteins

Antibody dependent cellular toxicity (ADCC) was measured using a europium incorporation assay. The human ovarian adenocarcinoma line SKOV3 was cultured in McCoy's 5A media supplemented with 10% fetal bovine sera (FBS). Peripheral blood mononuclear cells (PBMC) were obtained from leucopaks. The PBMCs were subjected to Ficoll-Hypaque density centrifugation, washed in PBS supplemented with 2% FBS, and resuspended in McCoy's 5A media with 10% FBS. The FcγRIIIA F158V genotype was determined for each individual donor. SKOV3 cells were labeled with Eu-DTPA. The cells were added to 96 well tissue culture plates at 5000/well and effector cells (PBMC) were added at 300,000/well (E:T 60:1). Antibodies were added at different concentrations and diluted across the plate. Controls included background, target and effector baseline counts, and 100% lysis wells. The PBMC mixtures with and without antibody were incubated for four hours at 37° C. Release of Eu-DTPA from lysed PBMC was determined by mixing 20 μl of the supernatant with DELPHIA® Enhancement Solution (Perkin Elmer, cat #1244-105) to form a highly fluorescent chelate, which is measured using time resolved fluorometry. Triplicate wells were set up for each antibody dilution and the percentage of lysis was calculated according to the formula: ((experimental release–background)/(maximal release–background))–((natural cytotoxicity–background)/(maximal release–background)). The terms are defined as follows: experimental release represents the mean count for the target cells in the presence of effector cells and antibody, background represents the mean for the supernatant from the final wash after labeling the target cells, maximal release represents the mean for target cells incubated with DELPHIA® lysis buffer (Perkin Elmer, cat #4005-0010) and natural cytotoxicity represents the mean count for the target cells in the presence of effector cells. Data points were fit to a four parameter logistic regression model using Prism 5.0 software. All curves were constrained to share the same maximum, minimum, and slope.

Those of ordinary skill in the art would recognize and appreciate that the assays in Examples 10-12 can be readily adapted for requirements pertaining to any immunoglobulin molecule. Furthermore, an in vivo ADCC assay in an animal model can be adapted for any specific IgG using the methods of Borchmann et al., Blood, 102: 3737-3742 (2003); Niwa et al., Cancer Research, 64: 2127-2133 (2004).

Figure 11:
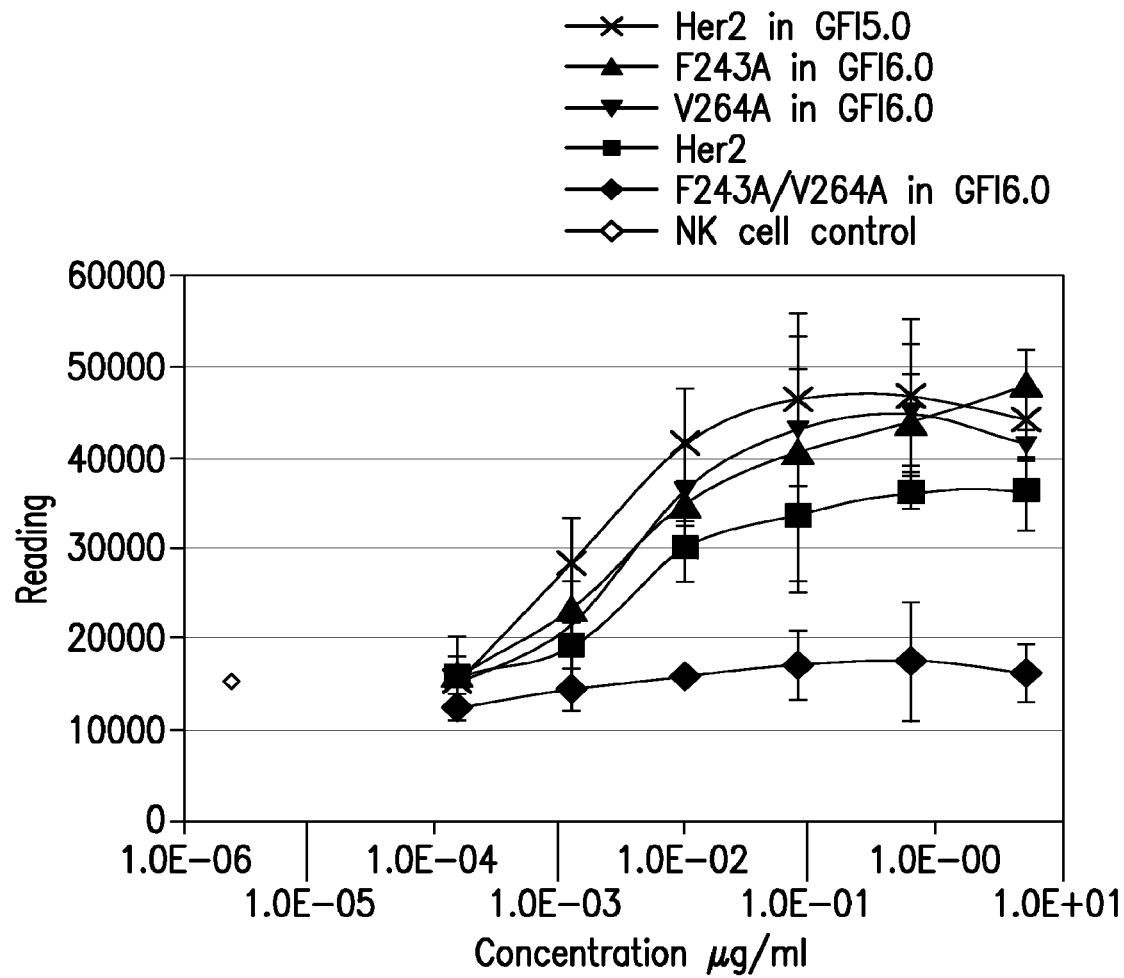
FIG. 11 is a graphic representation of the ADCC response for the various antibodies produced by the materials and methods described in Example 13: ■—Her2; ▲—F243A produced with GS6.0 glycosylation; ▼—V264A produced with GS6.0 glycosylation; ♦—F243A/V264A produced with GS6.0 glycosylation; ◇—NK cell killing without antibody; X—Her2 produced in GFI2.0.

The results are shown in FIG. 11. The single Fc muteins showed an ADCC activity profile similar to that for the Her2 antibody and approximately five fold lower than the *Pichia pastoris* Her2 antibody produced in a GFI 5.0 host. As illustrated in FIG. 11, ADCC activity is virtually absent for the antibody produced from the double Fc mutein, as expected from the FcγRIIIa binding data.

Example 14

Subcutaneous PK Study for Anti-Her2 and its Fc Muteins

The subcutaneous PK study was conducted in C57B6 mice. Antibody samples were administrated subcutaneously at the dose of 1 mg/kg (n=3). Ten μl of blood was collected with a capillary tube at the collection time points of 1, 6, 24, 53, 77, 120, 192, 240, 288 and 360 hours and transferred to a microfuge tube containing 90 μl of calcium and magnesium free PBS and 1.8 mg/ml $K_2EDTA$. Human IgG levels were determined on a Gyros® Bioaffy (Uppsala, Sweden) workstation using a sandwich immunoassay. 100 μg/ml biotinylated mouse monoclonal, anti-human kappa chain (BD Pharmingen, San Diego, CA) was used as the capture antibody and 12.5 Nm ALEXA®-647 labeled mouse monoclonal, anti-human Fc, Pan IgG (Southern Biotech, Birmingham, AL) was used as the detection antibody. The entire immunoassay was automated from capture antibody immobilization and analyte addition, to detection antibody addition and wash steps. Standards and QC were prepared in 5% mouse control plasma (EDTA) as 20× stocks and diluted 1:20 into 5% mouse plasma in assay buffer (PBS, 0.01% TWEEN® 20) prior to analysis. The linear range for accurate IgG concentration determination was established with spiked QC and found to be 5-5000 ng/ml. Accuracy and precision acceptability limits were +/−20% with a lower limit of quantitation (LLOQ) of +/−25%. Standards and QC could be frozen and thawed three times without significant loss of signal. Standards, QC and study samples were stored at −70° C. Study samples were thawed and diluted 1:20 into 5% mouse plasma in assay buffer and further diluted 1:10 if levels were outside the linear assay range. All standards, QC and study samples were assayed in duplicate and the average results reported. Concentrations were determined using a $5^{th}$ parameter logistic curve fit. Pharmacokinetic parameters were calculated for each animal with WinNonlin® using noncompartmental analysis of serum mAb concentration-time data (WinNonlin® Enterprise Version 5.01, Pharsight Corp, Mountain View, CA).

As shown in FIG. 12, mice treated with *Pichia pastoris* Her2 with GFI5.0 glycosylation and Her2 have similar t½ and serum concentrations, while mice treated with the Fc double mutein Her2, produced with GFI6.0 glycosylation, exhibited a higher Cmax (Maximum Concentration) and about a 30% increase in serum concentration as compared to mice treated with Her2 produced in CHO cells. Thus, of the three samples injected subcutaneously, the Fc double mutein antibody exhibited better bioavailability (absorption or exposure) based on the higher Cmax and serum concentrations.

Example 15

Another set of Fcγ receptor binding assays for the anti-Her2 antibody of the invention and its Fc muteins were carried out as described in Example 11, and the results are shown in FIG. 13; and Tables 4 and 5.

TABLE 4

Comparison of FcγR Binding Affinity to Her 2 Antibody

| Sample | FcγRI | FcγRIIa | FcγRIIb/c | FcγIIIa LF | FcγIIIa LV |
|---|---|---|---|---|---|
| Her2 Ab | 1.0 | 1.0 | 1.0 | 1.0 | 1.0 |
| Pichia Her 2 Ab | 0.6 | 0.4 | 0.9 | 11.3 | 2.8 |
| F243A/V264A | 0.2 | 0.02 | No binding | 0.04 | 0.4 |
| F243A | 0.6 | 0.1 | 0.3 | 8.4 | 3.3 |
| V264A | 0.6 | 0.03 | 0.2 | 3.6 | 1.4 |

Ratio calculation: STD EC50/anti-antigen mAb
Ratio > 1.0 higher affinity than Her2 Ab
Ratio < 1.0 lower affinity than Her 2 Ab

TABLE 5

Comparison of FcγR Binding Affinity to Pichia Her 2 Antibody

| Sample | FcγRI | FcγRIIa | FcγRIIb/c | FcγIIIa LF | FcγIIIa LV |
|---|---|---|---|---|---|
| Pichia Her 2 Ab | 1.0 | 1.0 | 1.0 | 1.0 | 1.0 |
| F243A/V264A | 0.5 | 0.04 | No binding | 0.003 | 0.1 |
| F243A | 1.0 | 0.2 | 0.3 | 0.74 | 1.2 |
| V264A | 0.9 | 0.1 | 0.2 | 0.3 | 0.5 |

Ratio calculation: STD EC50/anti-antigen mAb
Ratio > 1.0 higher affinity than Pichia Her2 Ab
Ratio < 1.0 lower affinity than Pichia Her 2 Ab Example 16

ADCC Evaluation of Anti-HER2 Antibodies and Fc Muteins

ADCC analysis was performed using SKOV3 target cells (ATCC®, Cat #HTB-77). On the day before the assay, primary NK effector cells (Biological Specialty, Cat #215-11-10) were pelleted at 1000 rpm for 15 minutes and resuspended to $1 \times 10^6$ cells/ml in RPMI minus phenol red media (Invitrogen, catalog #11835-030) supplemented with 10% FBS (Cellgro, Cat #35-016-CV). The resuspended NK cells were incubated overnight at 37° C. under 5% $CO_2$.

On the day of the assay, a flask of adhered SKOV3 target cells was washed with PBS, and the cells were detached using 3 ml trypsin (Cellgro, Cat #25-053-CI) and incubation for 2-5 minutes at 37° C. The cells were collected with 23 ml RPMI minus phenol red media, 10% FBS and pipetted up and down to break apart clumps. The harvested cells were centrifuged at 1800 rpm for 5 minutes and resuspended to a concentration of $1 \times 10^7$ cells/ml with RPMI minus phenol red media, 10% FBS. The target cells ($1 \times 10^7$ cells) were labeled with 100 µCi of Chromium-51 (5 mCi Sodium chromate in normal saline, Perkin Elmer, Cat #NEZ03005MC). Target cells were incubated at 37° C. for one hour with shaking every 15 minutes. Cells were centrifuged at 1800 rpm for 2 minutes and resuspended in one ml RPMI minus phenol red media, 10% FBS. Cells were washed two additional times with one ml RPMI minus phenol red media, 10% FBS with centrifugation at 1800 rpm for 2 minutes between each wash. After the final wash, the labeled target cells were resuspended in RPMI minus phenol red media, 10% FBS to a final concentration of $2.5 \times 10^5$ cells/ml.

Test antibodies used in these assays were anti-HER2 mAb produced in GFI 5.0, anti-HER2 mAb F243A produced in GFI 6.0 (GS6.0/F243A), anti-HER2 mAb V264A produced in GFI 6.0 (GS6.0/V264A), and anti-HER2 mAb F243A/V264A produced in GFI 6.0 (GS6.0/F243A/V264A). While the SKOV3 target cells were being labeled, test antibodies were diluted using a 3-fold serial titration (starting at 1 µg/ml) in RPMI minus phenol red media, 10% FBS in a polystyrene 96-well plate (Costar, Cat #353077). To the wells of a separate 96-well assay plate, 100 µl of Cr-51 labeled SKOV3 target cells (=25,000 cells) were transferred. After the antibody dilution plate was prepared, 10 µl of each dilution was transferred to the 96-well assay plate containing the labeled target cells. For the controls, 10 µl of TRITON™-X100 (10% stock, Fluka Analytical, Cat #93443) or 10 µl of media was added to "Max lysis" or "spontaneous release" control wells, respectively. Each antibody dilution was tested in duplicate, while 6 replicates of each control were tested.

Primary NK cells were pelleted at 1200 rpm for 5 minutes and gently resuspended to $2.5 \times 10^6$ cells/ml in RPMI minus phenol red media, 10% FBS. To all sample wells and "no antibody" control wells (i.e., excluding "spontaneous release" and "max lysis" controls), 100 µl of NK cells (=250,000 cells) was added for an effector:target ratio of 10:1. The assay plate was incubated at 37° C. under 5% $CO_2$ for four hours. After the incubation, the assay plate was centrifuged at 300 rpm for 5 minutes. Thirty µl of the supernatants was added to 250 µl of Microscint™ 20 (Perkin Elmer, Cat #6013621) in a 96-well Picoplate (Perkin Elmer, Cat #6005185). The Cr-51 release was measured in a Packard TOPCOUNT® scintillation counter.

Percent lysis was calculated as: ((ADCC experimental release−Spontaneous release)/(Max release−Spontaneous release))*100

The results of these assays are presented in FIG. 14. As shown in FIG. 14, the F243A single mutein antibody and the V264A single mutein antibody had a 5-10 fold reduction in ADCC activity when compared to the parent (wildtype) antibody; while the F243A/V264A double mutein antibody had more than 100 fold reduction in ADCC activity when compared to the parent (wildtype) antibody.

Example 17

Statistical Analysis of ADCC Data of Anti-HER2 Antibody and its Fc Muteins

The objective of the study was to determine if the percentage lysis for the double mutant variant is synergistic with respect to the two single mutant variants. The determination is made by comparing the $ED_{50}$ (antibody level corresponding to 50% lysis) between the double mutant variant (group 4) and the assumed additive reference curve (shown in FIG. 15 and Table 6). Since the lower limit of the $ED_{50}$ for the double mutant curve is above the top antibody level assayed and is well above the upper limit of the ED50 for additive reference curve we conclude that the effect of the double mutation is much more than additive.

Statistical Methods and Results:

The objective was to determine whether the double mutation variant of the HERCEPTIN® antibody (GS6.0/F243A/V264A) demonstrates a synergistic effect compared to the two single mutation variants (GS6.0/F243A and GS6.0N264A). There we four antibody groups: Group 1 (GS5.0), Group 2 (GS6.0/F243A), Group 3 (GS6.0N264A) and Group 4 (GS6.0/F243A/V264A).

Data from three donors is run on separate 96-well plates. The observations from each plate are normalized by converting the values to percentage of lysis as follows:

$$\% \text{ Lysis} = 100 \times \left( \frac{O_{rc} - O_N}{O_P - O_N} \right)$$

where: $O_{rc}$ is the observed response in the $r^{th}$ row and $c^{th}$ column of each plate.

$O_N$ is the average response of the negative controls for each plate.

$O_P$ is the average response of the positive controls for each plate.

Duplicate % lysis values for each antibody-level and group are then averaged.

The data from all four groups and all three donors are modeled jointly. We assume the 'antibody level-response' relationship follows a sigmoid Hill Equation (Eq. 1). We use (100% minus % lysis) as our response variable (Y) and the log antibody-levels as the explanatory variable (X). In order to make comparisons about the potency of the various mutations and fit the models, some assumptions about the model parameters for each group are made.

The form of the model used assumes:
1. The span (a) and the plateau (d), for all the 4 treatment groups are the same.
2. The same slope for all the treatment groups except the GS5.0 group which is allowed to have a different slope.
3. The $EC_{50}$ parameters ($\gamma$) are different for the different groups.

The Hill Equation:

$$Y_{ij} = \frac{a}{1 + \left( \frac{X_{ij}}{\gamma + \gamma_j} \right)^{\beta_0 + \beta_j}} + d \quad \text{(Eq. 1)}$$

With the constraints: $\gamma_1=0$, $\beta_1=0$ and $\beta_2=\beta_3=\beta_4=\beta$ Here:
$Y_{ij}$ is the $i^{th}$ response (100-% Lysis) for the $j^{th}$ treatment
$X_{ij}$ is the antibody level (on the log scale) corresponding to $Y_{ij}$
j=1 for GS5.0 j=2 for GS6.0/F243A j=3 for GS6.0/V264A j=4 for GS6.0/F243A/V264A It is further assumed that if the two single mutants (GS6.0/F243A and GS6.0/V264A) were additive than the equation for the combined effects would be:

$$Y_{i(additive)} = \frac{a}{1 + \left( \frac{X_{i(additive)}}{(\gamma + \gamma_2 + \gamma_3)} \right)^{\beta_0 + \beta}} + d \quad \text{(Eq. 2)}$$

with the parameters a, d, $\gamma$, $\gamma_2$, $\gamma_3$, $\beta$ and $\beta_0$ being the same as in Eq. 1.

The models (Eq. 1 and Eq. 2) are fit using PROC NLIN in SAS v9.2. The observed data values and the fitted curves for the four groups, as well as the assumed additive reference curve for the two single mutation groups combined are displayed in the FIG. 15. The $ED_{50}$'s along with their confidence intervals (on the original scale) are given in Table 6.

TABLE 6

| Groups | ED50 | 95% Confidence Interval | |
|---|---|---|---|
| Group 1: GS5.0 (anti-Her 2 mAb produced in GFI 5.0) | 0.011 | 0.0085 | 0.0131 |
| Group 2: GS6.0/F243A (anti-Her 2 mAb F243A produced in GFI 6.0) | 0.059 | 0.0457 | 0.0769 |
| Group 3: GS6.0/V264A (anti-Her 2 mAb V264A produced in GFI 6.0) | 0.072 | 0.0558 | 0.0942 |
| Group 4: GS6.0/F243A/V264A (anti-Her 2 mAb F243A/V264A doble mutein produced in GFI 6.0) | >1 * | >1 * | >1 * |
| Group 2&3 combined: Additive Reference Curve | 0.407 | 0.3031 | 0.5455 |

* Estimated value is greater than the highest antibody level in the experiment.

In order to assess the effects of GS6.0/F243A/V264A compared to the two single mutations GS6.0/F243A and GS6.0/V264A; the ED50 of the group 4 is compared with the ED50 of the additive reference curve. If the confidence intervals are non-overlapping then one can conclude that the two quantities are statistically different.

The 95% confidence interval for the $ED_{50}$ of the additive reference curve is (0.3031, 0.5455) while the estimate and confidence intervals for the $ED_{50}$ of group 4 are all higher than 1 (the estimated values are outside the observed range of antibody-levels). The lower 95% confidence limit for the $ED_{50}$ of the double mutation is >1, which is much higher than upper 95% confidence limit for the $ED_{50}$ of the reference additive curve (group 2&3 combined). Hence one can conclude the two quantities are significantly different.

The above comparison of confidence intervals of $ED_{50}$'s is equivalent to comparing $\gamma_4$ versus the sum $(\gamma_2+\gamma_3)$, i.e. testing the hypothesis that Ho: $\gamma_4=(\gamma_2+\gamma_3)$ versus the alternative that Ha: $\gamma_4>(\gamma_2+\gamma_3)$ Let $SSE_{reduced}$ and $SSE_{full}$ is the residual sum of squares from the reduced model and the full model respectively. The full model is obtained by fitting Eq. 1 to the data while the reduced model is obtained by substituting $\gamma_4$ in Eq. 1 with $(\gamma_2+\gamma_3)$.

The hypothesis:

$$H_0: \gamma_4=(\gamma_2+\gamma_3) \text{ versus } H_a: \gamma_4>(\gamma_2+\gamma_3)$$

The Test Statistic:

$$F_{obs} = \left\{ \frac{SSE_{reduced} - SSE_{full}}{DF_{reduced} - DF_{full}} \right\} / MSE_{full}$$

The p-value:

$$P(F_{obs} > F_{(DF_{reduced}-DF_{full}, DF_{full})}) < 0.0001$$

Since the p-value is <0.0001 we can reject $H_0$ and conclude that $\gamma_4 > (\gamma_2 + \gamma_3)$.

The data and model based comparisons indicate that the double mutation GS6.0/F243A/V264A has a significantly lower % lysis, than the hypothesized combined effects of the two single mutations. The effect of the double mutation is much more than an additive effect of the single mutations.

References Relating to this Example

[1] SAS® Proprietary Software 9.2 (TS2M2), SAS Institute Inc., Cary, NC, USA.
[2] 'Application of the Four-Parameter Logistic Model to Bioassay: Comparison with Slope Ratio and Parallel Line Models'; Aage Vølund, Biometrics, Vol. 34, No. 3 (September 1978), pp. 357-365

Example 18

Construction of Anti-TNFα Fc Muteins and ADCC Evaluation

The preparation of a double Fc muteins (F243A/V264A) of an anti-TNF monoclonal antibody in Pichia pastoris was carried out using the sequences and protocols listed below. The heavy and light chain sequences of the parent (wildtype) anti-TNFα antibody are set for the in SEQ Id NOs:10 and 11. The sequence of the heavy chain of the double mutein anti-TNFα antibody is set forth in SEQ ID NO:12. The light chain sequence of the wt and double mutein anti-TNFα antibodies are identical.

The signal sequence of an alpha-mating factor predomain (SEQ ID NO:8) was fused in frame to the end of the light or heavy chain by PCR fusion. The sequence was codon optimized and synthesized by Genscript™ (GenScript USA Inc., 860 Centennial Ave. Piscataway, NJ 08854, USA). Both heavy chain and light chain were cloned into antibody expression vector as similar way of constructing anti-HER2 IgG1 and its Fc muteins.

The heavy and light chains with the fused signal sequence of IgG1 and its muteins were cloned under Pichia pastoris AOX1 promoter and in front of S. cerevisiae Cyc terminator, respectively. The expression cassette of the completed heavy and light chains was put together into the final expression vector. Genomic insertion into Pichia pastoris was achieved by linearization of the vector with SpeI and targeted integration into the Trp2 site. PlasmID PGLY6964 encodes wildtype anti-TNFα IgG1 antibody. PlasmID PGLY7715 undoes the anti-TNF alpha IgG1 F243A/V264A double mutein.

Glycoengineered Pichia GFI5.0 YGLY8316 and GFI6.0 YGLY 22834 Hosts for Producing Anti-TNFα its Fc Muteins The genotype of the GFI5.0 strain YGLY16786 used for the expression of the anti-TNFα antibodies and its Fc muteins, is as follows: ura5Δ::ScSUC2 och1Δ::lacZ bmt1Δ::lacZ bmt2Δ::lacZbmt3Δ::lacZbmt4Δ::lacZ/KlMNN2-2 mnn4L1Δ::lacZ/MmSLC35A3 pno1Δ::lacZ ADE1::lacZ/FB8/NA10/MmSLC35A3 his 1::lacZ-URA5-lacZ/XB33/SpGALE/DmUGT arg1::HIS1/KD53/TC54 PRO1::ARG1/AOX1-ScMFpreTrMNS1PRO1::ARG1/AOX1-ScMFpreTrMNS1.

The genotype of the engineered Pichia pastoris GFI 6.0 strain YGLY23423 used for the expression of the anti-TNFα Fc DM mutein is as follows: ura5Δ::ScSUC2 och1Δ::lacZ bmt2Δ::lacZ/KlMNN2-2 mnn4L1Δ::lacZ/MmSLC35A3 pno1Δ mnn4A::lacZ ADE1:lacZ/NA10/MmSLC35A 3/FB8his1Δ::lacZ/ScGAL10/XB33/DmUGT arg1Δ::HIS1/ KD53/TC54bmt4Δ::lacZ bmt1Δ::lacZ bmt3A::lacZ TRP2: ARG1/MmCST/HsGNE/HsCSS/HsSPS/MmST6-33ste13Δ::lacZ/TrMDS1 dap2Δ::Nat$^R$ TRP5:Hyg$^R$MmCST/HsGNE/HsCSS/HsSPS/MmST6-33 Vps10-1Δ:: AOX1p_LmSTT3d.

The cells were transformed, screened and purified as indicated in Examples 4-7.

Antibody Dependent Cell Cytotoxicity (ADCC) Evaluation of Anti-TNFα Fc Muteins

ADCC analysis was performed using Jurkat FlpIn target cells stably-expressing a non-cleavable variant of TNFα which has the first 12 amino acids removed—Jurkat FlpIn TNFα (Δ1-12) target cells. These cells were prepared by transfecting Jurkat FlpIn human T-cell leukemia cells (Invitrogen) with a nonsecretable cell surface mutant of TNFα (Δ1-12 TNFα). Perez et al., Cell 63; 251-258 (1990). The Δ1-12 TNFα DNA was cloned into pcDNA5 vector (Invitrogen) to use for the transfection. Expression of cell surface TNFα was confirmed by flow cytometry.

On the day before the assay, primary NK effector cells (Biological Specialty, Cat #215-11-10) were pelleted at 1200 rpm for 12 minutes and gently resuspended to approximately $1-1.5 \times 10^6$ cells/ml in RPMI minus phenol red media (Invitrogen, catalog #11835-030) supplemented with 10% heat-inactivated FBS (Sigma, Cat #F4135), 10 mM HEPES (Gibco, Cat #15630), 2 mM L-glutamine (Cellgro, Cat #25-005-CI), and 1× penicillin/streptomycin (Cellgro, Cat #30-002-CI). The resuspended NK cells were incubated overnight at 37° C. under 5% $CO_2$.

On the day of the assay, Jurkat FlpIn™ TNFα (Δ1-12) target cells were centrifuged at 1200 rpm for 5 minutes, and the cell pellet was gently resuspended to a concentration of $2 \times 10^6$ cells/ml in RPMI minus phenol red media supplemented with 5% heat-inactivated FBS. The cells were labeled with 25 µl DELFIA® BATDA labeling reagent (from DELFIA® EuTDA Cytotoxicity kit, Perkin Elmer, Cat #AD0116). Cells were mixed gently and incubated at 37° C. for 20 minutes with gentle mixing every 10 minutes. Cell volume was adjusted to 30 ml with DPBS containing 1.5 mM probenicid (Invitrogen, Cat #P36400) and centrifuged at 1200 rpm for 5 minutes. Cells were washed three times with 30 ml DPBS containing 1.5 mM probenicid with centrifugation at 1200 rpm for 5 minutes between each wash. After the final wash, the labeled target cells were resuspended in RPMI minus phenol red media supplemented with 5% heat-inactivated FBS and 1.5 mM probenicid to a final concentration of $2.5 \times 10^5$ cells/ml.

Test antibodies used in the assay were: anti-TNF IgG1 wildtype antibody (designated "GFI774") produced in GFI 5.0, non-sialylated anti-TNF IgG1 antibody (GFI774) F243A/V264A produced in GFI 5.0, and syalylated anti-TNF IgG1 antibody (GFI774) F243A/V264A produced in GFI 6.0. The non-syalylated anti-TNF IgG1 antibodies—F243A/V264A—produced in GFI 5.0 comprise the following glycoforms: 84% G2, 2% G1 and 14% hybrid N-glycans. The syalylated anti-TNF IgG1 antibodies—F243A/V264A—produced in GFI 6.0 comprise the following glycoforms: 27% A1, 50.6% A2, and 5.7% A1 hybrid (overall, more than 83% of the N-glycans are syalylated.

While the Jurkat FlpIn™ TNFα (Δ1-12) target cells were being labeled, 2× concentrations of antibodies were diluted using a 3-fold serial titration (starting at 40 µg/ml) in RPMI minus phenol red media supplemented with 5% heat-inactivated FBS and 1.5 mM probenicid in a 96-well polypropylene, round-bottom plate (Costar, Cat #5699; lids—Costar Cat #3931). After the dilution plate was prepared, 100 µl of each 2× dilution was transferred to a new 96-well round-bottom polypropylene plate (100 µl of media only was transferred for the "no antibody" controls). RPMI minus phenol red media supplemented with 5% heat-inactivated FBS and 1.5 mM probenicid was also transferred to the 96-well plate for the "spontaneous release" and "max lysis" controls (150 µl per well) and the "background" control (200 µl per well). Each antibody dilution was tested in duplicate, while each control was tested in quadruplicate.

To all wells except "background" controls, 50 µl of Europium-labeled Jurkat FlpIn™ TNFα (Δ1-12) cells (=12,500 cells) were added and mixed gently. Primary NK cells were pelleted at 1200 rpm for 12 minutes and gently resuspended to $2.5\times10^6$ cells/ml in RPMI minus phenol red media supplemented with 5% heat-inactivated FBS and 1.5 mM probenicid. To all sample wells (i.e., excluding "spontaneous release", "max lysis", and "background" controls), 50 µl of NK cells (=125,000 cells) was added, for an effector:target ratio of 10:1. Samples were mixed gently, and the assay plate was incubated at 37° C. for two hours. After 1 hour and 15 minutes, 10 µl of 20% TRITON™-X100 (Pierce Surfact-Amps X-100, Cat #28314) or 10 µl of media was added to "max lysis" or "spontaneous release" control wells, respectively. The plate was incubated at 37° C. for an additional 45 minutes (total incubation time was 2 hours). While plates were incubating, DELFIA® Europium Solution (from DELFIA® EuTDA Cytotoxicity kit) was equilibrated at room temperature. After the two hour incubation, the assay plate was centrifuged at 1500 rpm for 5 minutes. Twenty µl of the supernatants was transferred to a white, flat-bottom clear plate (from DELFIA® EuTDA Cytotoxicity kit or Costar, Cat #3632) taking care that no bubbles were introduced. To each well, 200 µl of DELFIA® Europium Solution was added, and the plate was covered with an aluminum foil seal. The assay plate was incubated at room temperature for 15 minutes with gentle shaking. Fluorescence was measured using a Perkin Elmer Envision™ instrument set up for reading Europium.

Percent lysis was calculated as follows:
1) the average of the background control was subtracted from all raw values,
2) the % of ADCC activity was calculated as: ((ADCC experimental value−Spontaneous release)/(Max Lysis−Spontaneous release))*100
and
3) the final % lysis values were reported as % ADCC activity from step 2 minus "No Antibody" control.

The results of these assays are presented in FIG. 16. As shown in FIG. 16, the non-sialylated and sialylated anti-TNFα IgG1—F243A/V264A double mutein had more than 1000 fold reduction in ADCC as compared to the parent (wildtype) polypeptide produced in GS5.0.

Example 19

Complement Dependent Cytotoxicity (CDC) Evaluation of Anti-TNFα double Fc muteins CDC analysis was performed using HEK293 FlpIn™ cells stably-expressing a non-cleavable variant of TNF α which has the first 12 amino acids removed. HEK293 FlpIn™ TNFα (Δ1-12) cells were grown in tissue culture flasks in Dulbecco's Minimal Essential Media (DMEM) minus phenol red (Gibco, Cat #21063) supplemented with 10% heat-inactivated FBS (Sigma, Cat #F4135), 100 ug/ml Hygromycin B (Cellgro, Cat #30-240-CR), and L-glutamine (Cellgro, Cat #25-005-CI) to 70% confluence. Cells were treated with 2 ml trypsin (Cellgro, Cat #MT25-053-CI), harvested with 8 ml DMEM minus phenol red media, 10% heat-inactivated FBS, and centrifuged at 1200 rpm for 10 minutes. The supernatant was removed and cell pellet was resuspended in DMEM minus phenol red media, heat-inactivated 10% FBS to a concentration of $4\times10^5$ cells/ml. The cells were plated in 100 µl (40,000 cells) per well in a 96-well black with clear bottom plate (Costar, Cat #3603) and incubated overnight at 37° C. under 5% $CO_2$.

Test antibodies used in the assay were: anti-TNF IgG1 antibody (designated "GFI774") produced in GFI 5.0, anti-TNF IgG1 antibody (GFI774) F243A/V264A produced in GFI 5.0, and anti-TNF IgG1 antibody (GFI774) F243A/V264A produced in GFI 6.0. (These antibodies are described in Example 18.) On the day of the assay, the media was aspirated with a multichannel pipettor from the wells of the 96-well plate and replaced with 50 µl of DMEM minus phenol red media, 1× penicillin/streptomycin. A 2-fold serial titration of test antibody (starting at 30 µg/ml) was prepared in DMEM minus phenol red media containing 1× penicillin/streptomycin, 10 µg/ml anti-human CD55 mouse IgG1 monoclonal antibody (IBGRL Research Products, Clone BRIC216, Cat #9404P) and 10 µg/ml anti-human CD59 mouse IgG2b monoclonal antibody (IBGRL Research Products, Clone BRIC 229, Cat #9409P). To the appropriate assay plate wells, 50 µl of the diluted antibody was added. Assay negative controls were assay media alone and human IgG (Jackson ImmunoResearch, Cat #009-000-003) diluted in the assay DMEM minus phenol red media (containing CD55 and CD59 antibodies). The assay lysis control was 0.25% TRITON-X100 (10% stock, Fluka, Cat #93443) diluted in the assay DMEM minus phenol red media (containing CD55 and CD59 antibodies). Each test antibody concentration was tested in duplicate while the assay controls were tested in triplicate. The assay plate containing test samples was mixed by tapping lightly, and the plate was incubated for approximately 10 minutes at 37° C. while the human complement sera was being prepared. Three ml of human complement (QUIDEL, Cat #A113) was diluted 1:2 with 3 ml of DMEM minus phenol red media containing 1× penicillin/streptomycin, and 50 µl of the diluted complement was added to the assay plate wells. The assay plate was mixed by tapping lightly, and the plate was incubated for 4 hours at 37° C. under 5% $CO_2$. A solution of 40% alamar blue (Biosource, Cat #DAL1100) was prepared by diluting 100% stock with DMEM minus phenol red media containing 1× penicillin/streptomycin, and 50 µl of the diluted alamar blue solution was added to the assay plate wells (=10% final). The assay plate was mixed by tapping lightly, and the plate was incubated overnight (15-20 h) at 37° C. under 5% $CO_2$. The next day, the assay plate was incubated for 10 minutes on a shaker at room temperature and fluorescence was read at excitation 544 nm, emission 590 nm. Percent CDC was calculated as: (1−(Sample raw fluorescence unit (RFU)−TRITON™-X100 RFU)/(Media RFU−TRITON™-X100 RFU))*100.

Figure 17:
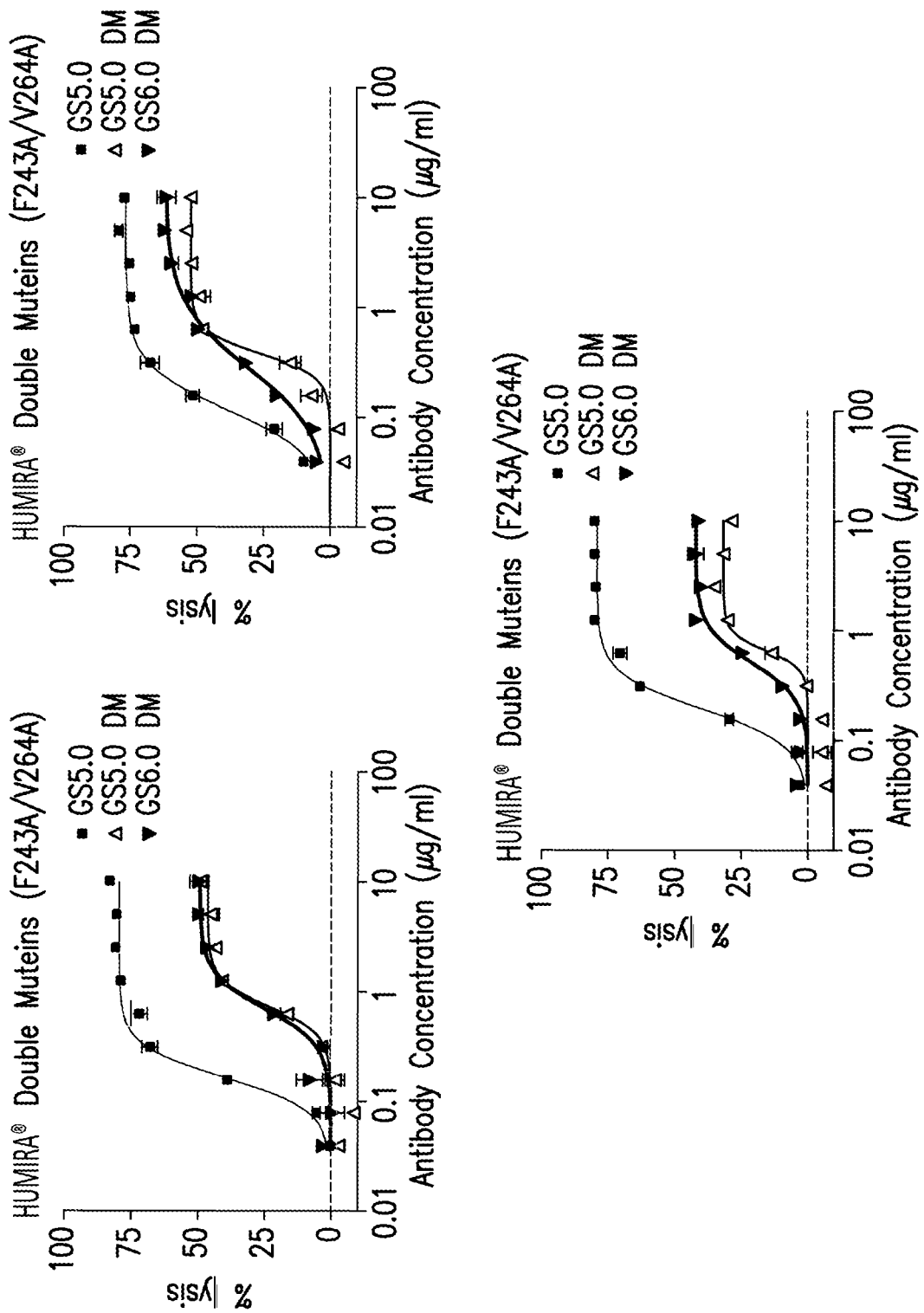
FIG. 17 is a graphic representation of the CDC response for the various antibodies produced by the materials and methods described in Example 19. HUMIRA® is the tradename for adalimumab.

The results of these assays are presented in FIG. 17. As shown in FIG. 17, the non-sialylated and sialylated anti-TNFα IgG1—F243A/V264A double mutein had about a 10 fold reduction in CDC activity as compared to the parent (wildtype) antibody.

Example 20

Effect of the Anti-TNFα Antibody and its Fc Muteins in a Collagen-Antibody Induced Arthritis (MA) Model MODEL INDUCTION: AIA (Antibody induced arthritis) is induced with a commercial Arthrogen-CIA® arthritogenic monoclonal antibody (purchased from Chondrex) consisting of a cocktail of 5 monoclonal antibodies, clone A2-10 (IgG2a), F10-21 (IgG2a), D8-6 (IgG2a), D1-2G(IgG2b), and D2-112 (IgG2b), that recognize the conserved epitopes on various species of type II collagen.

ANIMALS: 10 week old B10.RIII male mice which are susceptible to arthritis induction without additional of co-stimulatory factors were used. These animals were purchased from Jackson Laboratory.

CLINICAL SCORING: Paw swelling was measured daily post-induction of arthritis. The severity of the disease was graded on a 0-3 scale per paw as follows: 0, normal; 1, swelling of one digit; 2, swelling of two or more digits; 3, swelling of the entire paw. The maximal clinical score per mouse is 12.

STUDY DESIGN: Arthritis was induced by passive transfer of 3 mg of anti-CII mAb pathogen cocktail IV on day 0. Groups of Mice were Treated Subcutaneously with Following Reagents:

| Group/Reagent | Lot | Dose |
|---|---|---|
| A. Naïve | *** | *** |
| B. Isotype IgG1 | 78ABY | 33 mpk |
| C. Asialyated Anti-TNF | 36ADV | 33 mpk |
| D. α2,6 Sialyated Anti-TNF | 37ADV | 33 mpk |
| E. mTNFR-Ig | 82ABW | 33 mpk |
| F. GAMMAGARD | 84ADU | 33 mpk |
| G. GAMMAGARD | 84ADU | 1000 mpk |
| H. HUMIRA | 85ADU | 33 mpk |

Group n = 5 for all groups except Group A and H which have n = 3.

An isotype IgG1 antibody was used as a control. The antibody bound to mouse anti-hexon and had the designation "27F11".

The sample identified as "Asialyated Anti-TNF" corresponds to the anti-TNF antibody as described in Example 18 produced in GFI 5.0 comprising the F243A/V264A mutations. The sample identified as "α2,6 Sialyated Anti-TNF" corresponds to the anti-TNF antibody described in Example 18 produced in GFI 6.0 comprising the F243A/V264A mutations. The non-sylalated anti-TNF IgG1 antibodies—F243A/V264A—produced in GFI 5.0 comprise the following glycoforms: 84% G2, 2% G1 and 14% hybrid N-glycans. The syalylated anti-TNF IgG1 antibodies—F243A/V264A—produced in GFI 6.0 comprise the following glycoforms: 27% A1, 50.6% A2, and 5.7% A1 hybrid (overall, more than 83% of the N-glycans are syalylated).

MtNFR-Ig is an immunoadhesin (anti-TNF receptor Ig-fusion protein) comprising the extracellular domain OF MtNFR2 connected to mIgG1 Fc starting at the hinge and spanning the CH2 and the CH3 regions, and comprising the amino acid sequence of SEQ ID NO:16 produced in CHO cells.

GAMMAGARD® liquid was purchased from Baxter Corp.

HUMIRA® was purchased from Abbott Labs. HUMIRA® comprise asyalylated N-glycans with very little terminal galactose.

All groups of mice were dosed on day minus 1 and day 7 with the exception OF MtNFR-Ig, which received a total of three doses at days minus 1, +3, and +7. The Clinical Score was monitored for 14 days.

Figure 18A:
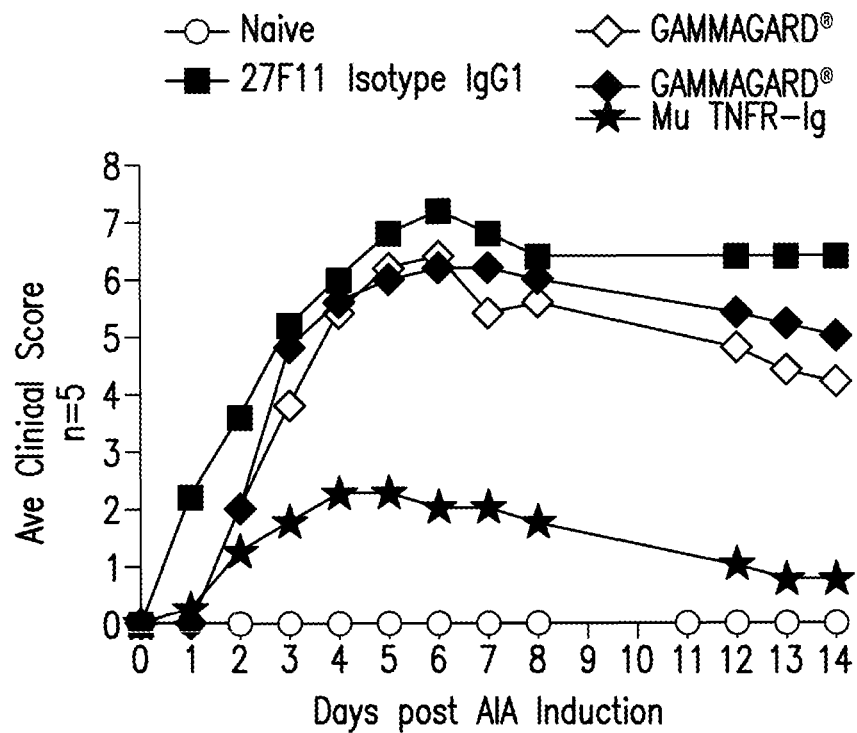
FIGS. 18A-18B are graphic representations of the effect of the Fc muteins of the invention in an AIA model described in Example 20. HUMIRA® is the tradename for adalimumab.
Figure 18B:
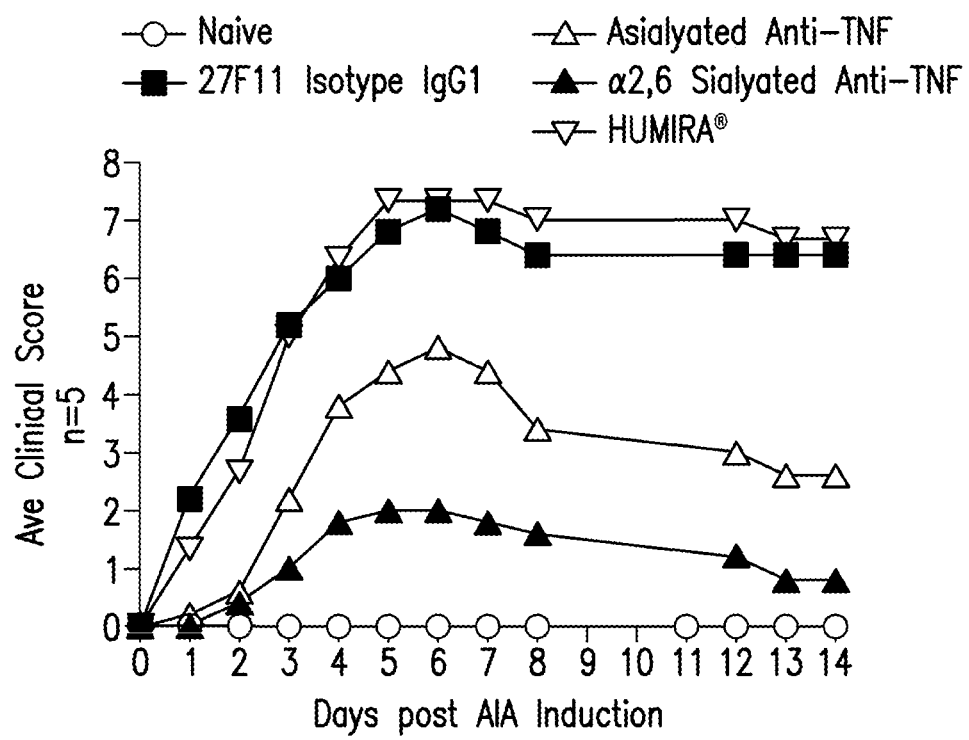

The results of these experiments are shown in FIGS. 18A and 18B. In this study, GAMMAGARD® did not demonstrate clinical efficacy. Mu-TNF-Ig showed good protection from disease in 4 out of 5 mice. HUMIRA® had very similar disease kinetics as the control IgG1. Asialyated Anti-TNF showed some dampening of disease. The α 2,6 sialylated Anti-TNF showed good disease protection in 5 out of 5 mice, and scores were comparable to anti-TNF therapy.

GENE EXPRESSION ANALYSIS: Expression of inflammatory and bone remodeling genes were determined by RT/PCR analysis of hind paws from isotype, a2,6 sialylated mAb OR MtNFR-Ig treated mice (n=4 per group). To perform the quantitative PCR, total RNA was isolated from hind paws using RNA STAT-60 (Tel-Test, Friendswood, TX, USA). Total RNA (5 µg) was subjected to treatment with DNase (Roche). DNase-treated total RNA was reverse-transcribed using Superscript™ II (Gibco/BRL). Primers were designed using Primer Express (PE Biosystems), or obtained commercially from Applied Biosystems.

Real-time quantitative PCR on 10 ng OF CDNA from each sample was performed using one of two methods. In the first method, two gene-specific unlabelled primers were utilized at 400 nM in a Perkin Elmer SYBR® green real-time quantitative PCR assay utilizing an ABI™ 5700 Instrument. In the second method, two unlabelled primers at 900 nM each were used with 250 nM of FAM-labelled probe (Applied Biosystems) in a TAQMAN™ real-time quantitative PCR reaction on an ABI 7700 sequence detection system. The absence of genomic DNA contamination was confirmed using primers that recognize genomic regions of the CD4 promoter—samples with detectable DNA contamination by real-time PCR were excluded from the study. Ubiquitin levels were measured in a separate reaction and used to normalize the data by the Δ–Δ Ct method, using the mean cycle threshold (Ct) value for ubiquitin and the genes of interest for each sample; the equation $1.8 e (Ct\ ubiquitin-Ct\ gene\ of\ interest) \times 10^4$ was used to obtain the normalized values. The results are shown in Table 7. Data shown is fold-increase of inflammatory/bone remodeling gene expression over that of gene expression in hind paws of naïve control mice.

TABLE 7

| | Fold induction over naïve mice | | |
|---|---|---|---|
| Gene | Isotype 33 mpk | α2,6 SA Humira 33 mpk | mTNFR-Ig 33 mpk |
| IL-1b | 14.43 | 0.90 | 0.43 |
| IL-6 | 18.45 | 0.75 | 0.77 |
| Tnfsf2-Tnfa | 2.63 | 0.98 | 0.70 |
| Tnfsf11-Rankl | 10.94 | 1.27 | 0.67 |
| Tnfrsf11a-Rank | 2.21 | 0.86 | 0.74 |
| MDL-1 long | 5.25 | 1.82 | 0.88 |
| F4/80 | 3.20 | 1.75 | 0.56 |
| Cd11b | 3.57 | 1.35 | 1.07 |
| Cd14 | 2.48 | 1.53 | 0.52 |
| Dap12 | 4.36 | 1.33 | 0.90 |
| TIMP-1 | 15.85 | 1.44 | 1.38 |
| PU.1-Sfpi1 | 3.88 | 1.09 | 0.79 |
| Trap-Acp5 | 10.19 | 1.85 | 1.17 |
| Ccl2-Mcp1 | 8.01 | 1.24 | 0.87 |
| Ccl3-Mip1a | 4.06 | 1.09 | 0.58 |
| Cxcl1-Groa | 16.39 | 1.65 | 0.69 |
| Cxcl2-Grob | 5.33 | 0.50 | 0.32 |
| Atp6v0d2 | 17.45 | 2.05 | 1.74 |
| Mmp9 | 13.53 | 1.88 | 1.32 |
| Fcgr1-Cd64 | 4.51 | 1.04 | 0.68 |
| Fcgr2b-Cd32a | 2.75 | 1.11 | 0.71 |
| Fcgr3 | 0.57 | 0.74 | 0.66 |
| Fcgr4 | 6.54 | 1.38 | 1.04 |
| Ctsk | 6.85 | 1.65 | 0.91 |
| Calcr | 1.80 | 0.49 | 0.94 |
| Cd68-Scard1 | 3.19 | 1.29 | 0.94 |
| Itgb2-Cd18 | 3.90 | 1.33 | 0.88 |

Example 21

Effect of the Anti-TNFα Antibody or its Fc Muteins in a Collagen-Antibody Induced Arthritis (MA) Model

The experiment described in Example 20 was repeated as described therein, with the exception that GAMMAGARD® was administered intravenously (while all other reagents were administered subcutaneously).

STUDY DESIGN: Arthritis was induced as described in Example 20.

All groups of mice were dosed on day minus 1 with the exception OF MtNFR-Ig, which received a total of two doses at days minus 1 and +3. The Clinical Score was monitored for 7 days.

Groups of Mice were Treated with Following Reagents:

| Group/Reagent | Lot | Dose |
|---|---|---|
| Naïve | *** | *** |
| Isotype IgG1 | 78ABY | 33 mpk |
| Asialyated Anti-TNF | 36ADV | 33 mpk |
| α2,6 Sialyated Anti-TNF | 37ADV | 33 mpk or 6.6 mpk |
| α2,3 Sialyated Anti-TNF | 19ADX | 33 mpk |
| mTNFR-Ig | 82ABW | 33 mpk |
| GAMMAGARD | 84ADU | 1000 mpk |
| HUMIRA | 85ADU | 33 mpk |
| 18 ADX PNG Humira | 18ADX | 33 mpk |
| 20 ADX No Glyco | 20ADX | 33 mpk |

Group n = 5 for all groups

The reagents: "Isotype IgG1", "Asialyated Anti-TNF", "α2,6 Sialyated Anti-TNf, MtNFR-Ig, GAMMAGARD® and HUMIRA® were described in Example 20.

The reagent identified as "α2,3 Sialyated Anti-TNF" corresponds to the anti-TNF antibody described in Example 18 produced in GFI 6.0 comprising the F243A/V264A, which was in vitro treated with neuraminidase to eliminate the α2,6 linked sialic acid, and further in vitro treated with α2,3 sialyltransferase. Briefly, the purified antibody (4-5 mg/ml) was in the formulation buffer comprising 6.16 mg sodium chloride, 0.96 mg monobasic sodium phosphate dehydrate, 1.53 mg dibasic sodium phosphate dihydrate, 0.30 mg sodium citrate, 1.30 mg citric acid monohydrate, 12 mg mannitol, 1.0 mg polysorbate 80 per 1 ml adjusted TO pH to 5.2. Neuraminidase (10 mU/ml) was added to antibody mixture and incubated at 37° C. for at least 5 hrs or until desilylation reached completion. The desialylated material was applied onto CaptoMMC™ (GE Healthcare) column purification to remove neuraminidase and reformulated in Sialyltransferase buffer (50 mM HEPES pH 7.2 150 mM NaCl, 2.5 mM $CaCl_2$, 2.5 mM $MgCl_2$, 2.5 mM $MnCl_2$) at 4 mg/ml. Mouse α2,3 sialyltransferase recombinant enzyme expressed in *Pichia* and purified via his-tag was used for α 2,3 sialylic acid extension. The enzyme mixture was formulated in PBS in the presence of Protease Inhibitor Cocktail (Roche™, cat #11873580001) at 1.2 mg/ml. Prior to the sialylation reaction, pepstatin (50 ug/ml), chymostatin (2 mg/ml) and 10 mM CMP-Sialic acid were added to the enzyme mixture followed by sterilization through 0.2 μm filter. One ml of enzyme mixture was added to 10 ml desialylated material. The reaction was carried out at 37° C. for 8 hrs. The sialylation yield was confirmed by mass determination by ESI-Q-TOF. The final material was purified using MABSELECT™ (GE Healthcare) and formulated in the buffer described above and sterile-filtered (0.2 μm membrane).

The reagent identified as "18 ADX PNG HUMIRA®" corresponds to the anti-TNF antibody described in Example 18 produced in GFI 6.0 comprising the F243A/V264A which was in vitro treated with PNG'ase F to remove all N-glycans. The PNGase F enzyme was obtained Prozyme, Inc., and used with a stoichiometry of 2 μl of commercial enzyme to 4 mg of IgG1 AT pH 7.4. The digested material was purified using MABSELECT™ (GE Healthcare). The final material was formulated and sterile-filtered (0.2 pin membrane).

The reagent identified as "20 ADX No Glyco" corresponds to the wildtype anti-TNF antibody described in Example 18, comprising a single mutation at position 297 which results in no glycosylation, produced in a GFI5.0 YGLY8316. The strain producing this antibody was clarified by centrifugation for 15 min at 13,000 g in a Sorvall™ EVOLUTION™ RC (kendo, Asheville, NC). The capture step was performed using MABSELECT™ (GE Healthcare) followed by a polishing step using Capto MMC™ (GE Healthcare). The final material was formulated and sterile-filtered (0.2 pin membrane).

Figure 19A:
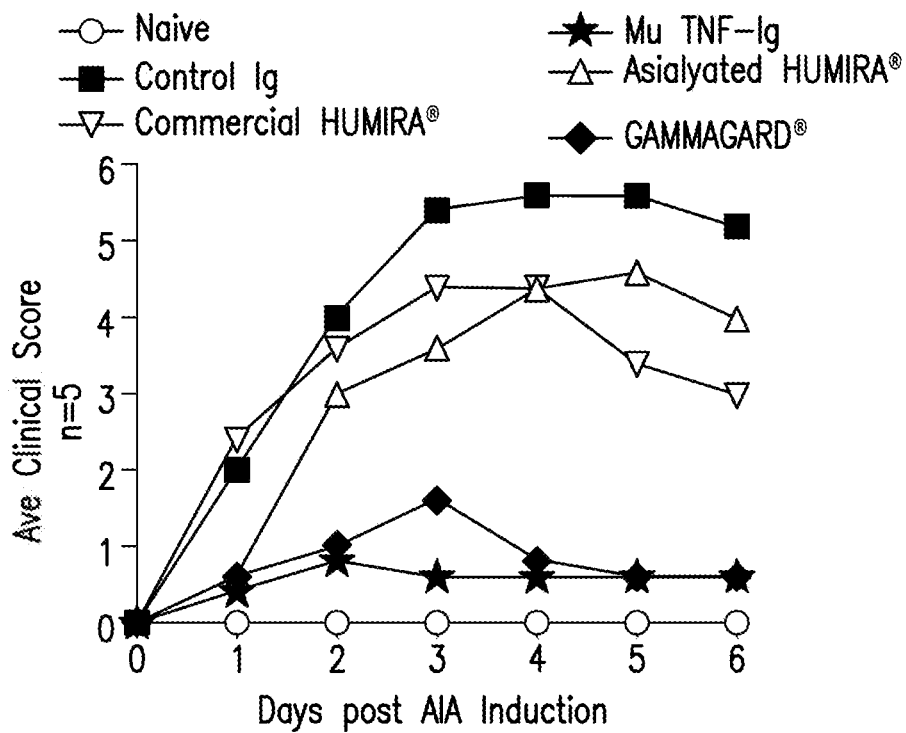
FIGS. 19A-19B are graphic representations of the effect of the Fc muteins of the invention in an AIA model described in Example 21. HUMIRA® is the tradename for adalimumab and HERCEPTIN® is the tradename for trastuzumab.
Figure 19B:
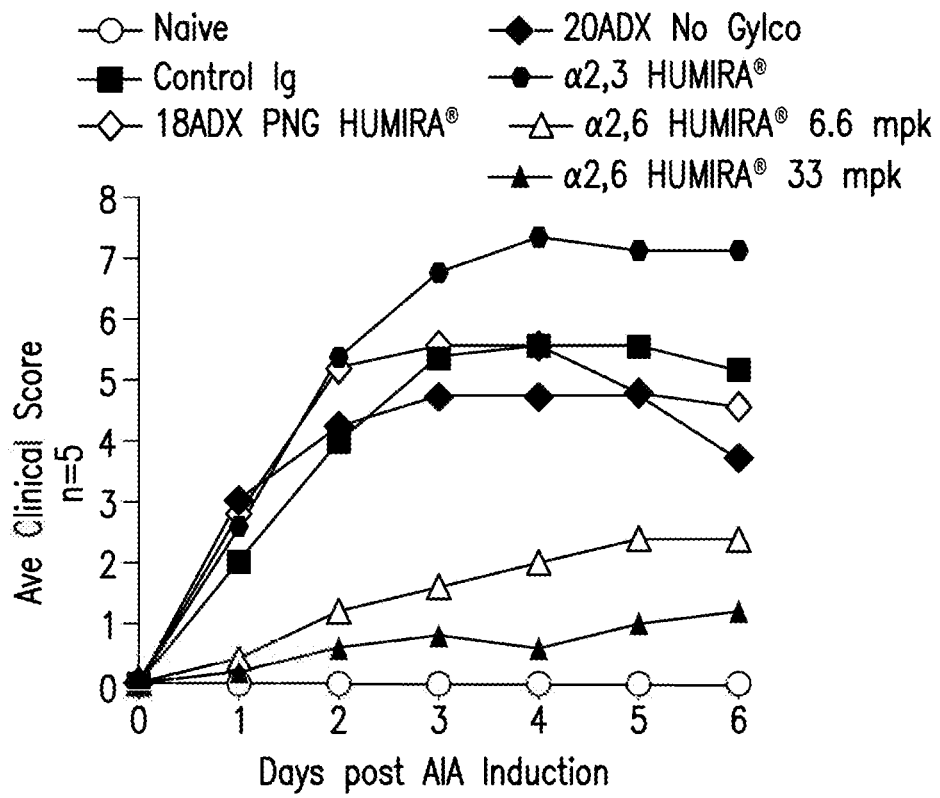

The results of these experiments are shown in FIGS. 19A and 19B.

GENE EXPRESSION ANALYSIS: Expression of inflammatory and bone remodeling genes were determined by RT/PCR analysis. To perform the quantitative PCR, total RNA was isolated from hind paws using RNA STAT-60 (Tel-Test, Friendswood, TX, USA). Total RNA (5 μg) was subjected to treatment with DNase (Roche). DNase-treated total RNA was reverse-transcribed using Superscript™ II (Gibco/BRL). Primers were designed using Primer Express™ (PE Biosystems), or obtained commercially from Applied Biosystems.

Real-time quantitative PCR on 10 ng of cDNA from each sample was performed using one of two methods. In the first method, two gene-specific unlabelled primers were utilized at 400 nM in a Perkin Elmer SYBR™ green real-time quantitative PCR assay utilizing an ABI 5700 Instrument. In the second method, two unlabelled primers at 900 nM each were used with 250 nM of FAM-labelled probe (Applied Biosystems) in a TAQMAN™ real-time quantitative PCR reaction on an ABI 7700 sequence detection system. The absence of genomic DNA contamination was confirmed using primers that recognize genomic regions of the CD4 promoter–samples with detectable DNA contamination by real-time PCR were excluded from the study. Ubiquitin levels were measured in a separate reaction and used to normalize the data by the Δ–Δ Ct method, using the mean cycle threshold (Ct) value for ubiquitin and the genes of interest for each sample; the equation 1.8 e (Ct ubiquitin–Ct gene of interest)×104 was used to obtain the normalized values. The results are shown in Table 8. Data shown is fold-increase of inflammatory/bone remodeling gene expression over that of gene expression in hind paws of naïve control mice.

TABLE 8

Fold induction over naïve mice

| Gene | Isotype Control 78ABY | Asialyated Humira 36ADV | α 2,3 Humira 19ADX | Gamma Guard 84ADU | TNFR-Ig 82ABW | α 2,6-high Humira 37ADV |
|---|---|---|---|---|---|---|
| IL-1b | 47.09 | 25.75 | 58.94 | 1.58 | 1.76 | 4.55 |
| IL-6 | 26.18 | 3.64 | 10.71 | 0.37 | 0.80 | 0.59 |
| RankL | 186.32 | 138.96 | 347.65 | 6.25 | 20.36 | 21.26 |
| MDL-1 | 4.65 | 3.79 | 5.71 | 1.23 | 0.97 | 1.93 |
| Cd11b | 9.43 | 13.20 | 23.11 | 1.77 | 3.17 | 5.25 |

TABLE 8-continued

Fold induction over naïve mice

| Gene | Isotype Control 78ABY | Asialyated Humira 36ADV | α 2,3 Humira 19ADX | Gamma Guard 84ADU | TNFR-Ig 82ABW | α 2,6-high Humira 37ADV |
|---|---|---|---|---|---|---|
| Dap12 | 4.45 | 3.54 | 6.01 | 1.81 | 1.59 | 2.26 |
| TIMP-1 | 15.98 | 6.80 | 18.43 | 1.40 | 1.21 | 1.38 |
| PU.1 | 6.91 | 9.18 | 15.50 | 1.00 | 1.48 | 3.17 |
| Trap-Acp5 | 13.88 | 15.44 | 35.34 | 1.19 | 2.14 | 5.72 |
| MCP1 | 14.96 | 5.66 | 11.62 | 1.46 | 1.44 | 1.59 |
| Cxcl1-Groa | 23.04 | 4.92 | 18.10 | 0.39 | 1.34 | 1.41 |
| Cxcl2-Grob | 30.83 | 6.30 | 16.06 | 2.93 | 1.15 | 0.99 |
| Atp6v0d2 | 16.62 | 9.81 | 21.87 | 1.60 | 1.81 | 2.68 |
| Mmp9 | 15.00 | 12.33 | 26.43 | 1.69 | 2.26 | 3.24 |
| Fcgr1-Cd64 | 5.84 | 4.48 | 8.68 | 1.87 | 1.59 | 2.36 |
| Fcgr2b-Cd32a | 3.63 | 2.81 | 4.34 | 1.48 | 1.59 | 1.60 |
| Fcgr3 | 4.07 | 6.64 | 7.73 | 1.33 | 1.81 | 4.86 |
| Fcgr4 | 8.91 | 7.79 | 14.10 | 2.93 | 2.12 | 4.15 |
| Ctsk | 13.13 | 15.04 | 30.55 | 1.25 | 2.20 | 4.17 |
| Itgb2 | 6.46 | 7.66 | 17.07 | 1.16 | 1.68 | 3.24 |
| MIP1a | 5.12 | 3.15 | 5.19 | 1.39 | 1.08 | 1.47 |

Example 22

FcγR Binding Assays of Anti-TNF Antibodies and Muteins

Figures 1, 20:
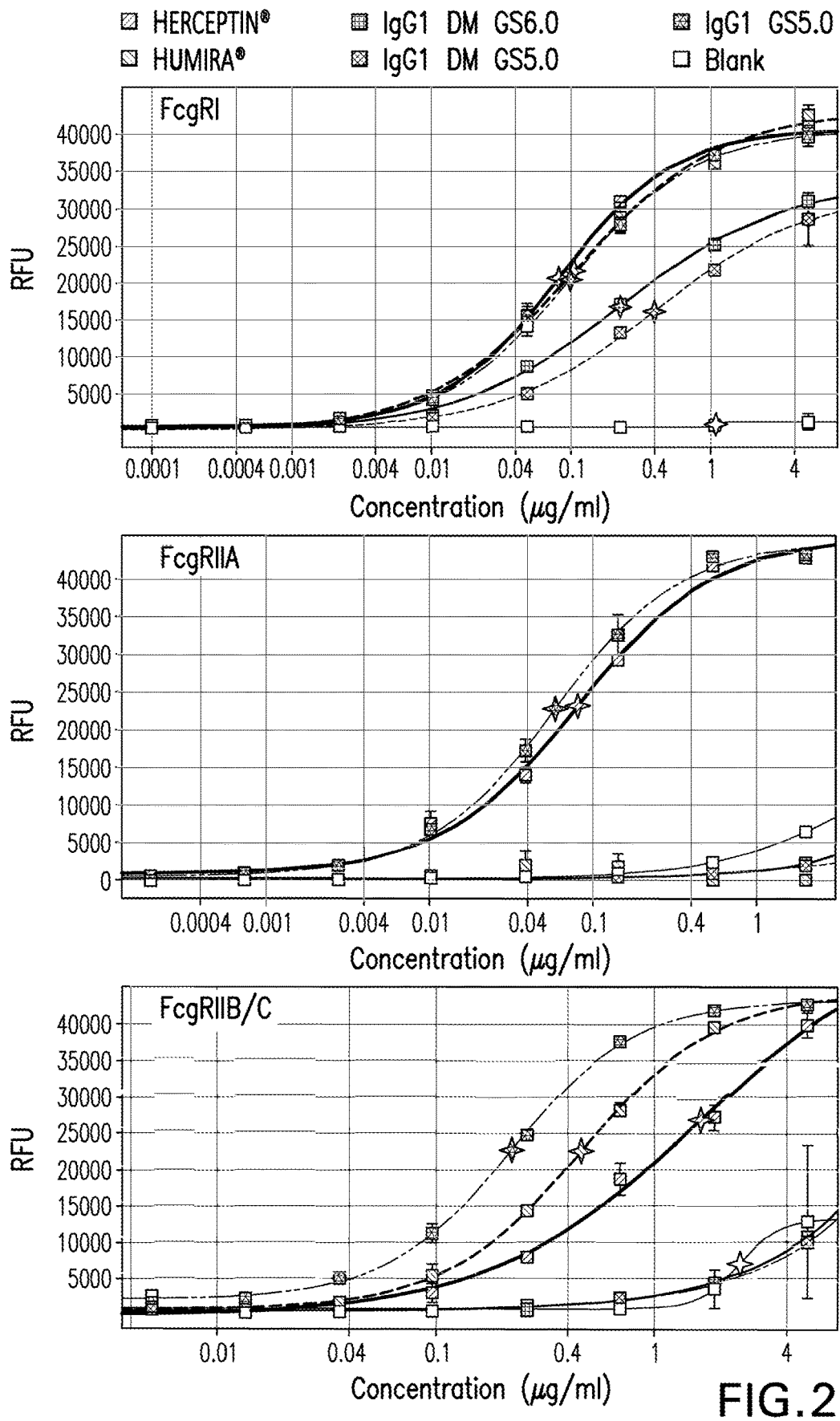
Figures 2, 20:
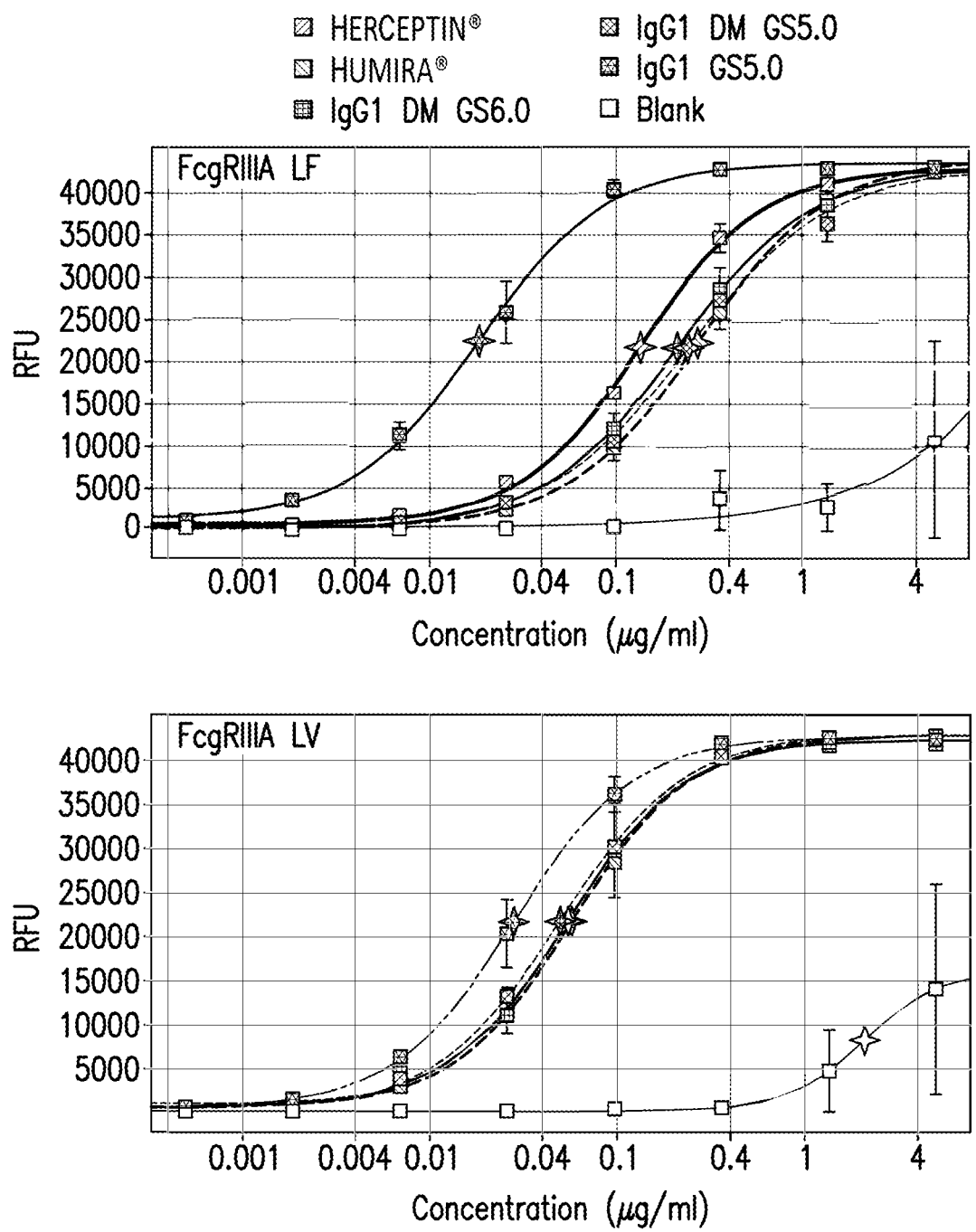

Fcγ receptor binding assays were carried out at as described in Example 1, using the anti-TNF antibodies described in Example 18. The results are shown in FIG. 20 and Tables 9-10.

TABLE 9

Reduction in Binding to Fcγ receptor compared to wildtype (parent) antibody produced in GS 5.0

| Sample | FcγRI | FcγRIIa | FcγRIIb/c | FcγIIIa LF | FcγIIIa LV |
|---|---|---|---|---|---|
| Anti-TNF DM (produced in GS5.0) | ↓ 4-10 | ↓ 60-100 | non-binding | ↓ 11-12 | ↓1.5-1.7 |
| Anti-TNF DM (produced in G56.0) | ↓ 2-3 | ↓ 100 | non-binding | ↓ 10-12 | ↓1.5-2.0 |

↓ indicates decreased affinity fold
↑ indicates increased affinity fold

TABLE 10

Reduction in Binding to Fcγ receptor compared to commercial HUMIRA

| Sample | FcγRI | FcγRIIa | FcγRIIb/c | FcγIIIa LF | FcγIIIa LV |
|---|---|---|---|---|---|
| Anti-TNF DM (produced in GS5.0) | ↓ 4-11 | non-binding | ↓ 20 | no difference | no difference |
| Anti-TNF DM (produced in GS6.0) | ↓ 2-4 | non-binding | ↓ 20 | no difference | no difference |
| Anti-TNF wildtype (produced in GS5.0) | no difference | ↑ 30 | ↑ 2 | ↑ 13-15 | ↑1.8-2.0 |

↓ indicates decreased affinity fold
↑ indicates increased affinity fold

Example 23

Construction of Additional Anti-Her2 Fc Double Muteins (at Positions 243/264) and their N-Glycan Composition Additional Fc double muteins of the Her2 IgG1 antibody described in Example 2 were constructed using a Stratagene QuikChange® Site-Directed Mutagenesis Kit Catalog #200518 (30 reactions) following the protocol they provided to process saturation mutagenesis with degenerate primers. The signal sequence of an alpha-mating factor predomain was fused in frame to the 5' end of the light chain and heavy chain. The resulting heavy and light chains with the fused signal sequence of IgG1 and its muteins were cloned under *Pichia pastoris* AOX1 promoter and in front of *S. cerevisiae* Cyc terminator, respectively. The expression cassette of the completed heavy and light chains was put together into the final expression vector.

The vectors were expressed in glycoengineered *Pichia* GFI6.0 hosts cells YGLY3582 and YGLY22812.

TABLE 11

| Strain | Description |
|---|---|
| YGLY4563 | GFI6.0 host YGLY3582 strain making anti-Her2 F243A/V264A double mutein |
| YGLY23294 | GFI6.0 host YGLY22812 strain making anti-Her2 F243Y/V264G double mutein |
| YGLY23280 | GFI6.0 host YGLY22812 strain making anti-Her2 F243T/V264G double mutein |
| YGLY23301 | GFI6.0 host YGLY22812 strain making anti-Her2 F243L/V264A double mutein |
| YGLY25259 | GFI6.0 host YGLY22812 strain making anti-Her2 F243L/V264N double mutein |
| YGLY23305 | GFI6.0 host YGLY22812 strain making anti-Her2 F243V/V264G double mutein |

The genotype of the GFI6.0 YGLY3582 strain is described at Example 4 (same as YGLY4563).

The genotype of the engineered *Pichia pastoris* GFI 6.0 YGLY22812 strain used for the expression of the anti-TNFα Fc DM mutein, is as follows: ura5Δ: ScSUC2 och1Δ::lacZ bmt2Δ::lacZ/KlMNN2-2 mnn4L1Δ::lacZ/MmSLC35A3 pno1Δ mnn4Δ::lacZ ADE1 lacZ/NA10/MmSLC35A3/FB8his1Δ::lacZ/ScGAL10/XB33/DmUGT arg1Δ::HIS1/KD53/TC54bmt4Δ: lacZ bmt1Δ::lacZ bmt3Δ::lacZ TRP2: ARG1/MmCST/HsGNE/HsCSS/HsSPS/MmST6-33ste13Δ::lacZ/TrMDS1 dap2Δ::NatR TRP5: HygRMMCST/HsGNE/HsCSS/HsSPS/MmST6-33 Vps10-1Δ::AOX1p_LmSTT3d. YGLY23294, YGLY23280, YGLY23301, YGLY25259 and YGLY23305 have the same genotype except they express different mutein listed in Table 11.

The strains were cultivated in 500 ml shake flasks with 300 ml of 2% BMGY media and shaked at 24° C. for 3 days.

Protocol for induction of shake flasks: Collect the total volume of each culture (300 ml) into falcon tubes and spin at 2500 rpm for 5 minutes. Pour away supernatant and resuspend cell pellets in a final volume of 150 ml 2% BMMY and 360 ul PMTi4 (stock concentration 0.65 mg/ml). Transfer to a fresh 500 ml shake flask and shake at 24° C. for 2 days. Spin down the induced cultures and collect the supernatant into fresh falcon tubes.

The secreted antibodies were purified by protein A column using GE Healthcare, STREAMLINE™ rProtein A (catalog no. 17-1281-01) and BioRad poly-prep chromatography columns (10 ml) (catalog no. 731-1550). The following buffers were used:

Wash buffer #1: 20 mM TRIS pH 7.0, 1M NaCl
Wash buffer #2: 20 mM TRIS pH 7.0
Neutralization buffer: 1M TRIS pH 8.0-pH 9.0
Elution buffer: 100 mM or 50 mM Sodium Citrate pH 3.0
Cleaning solution: 6M Urea in water.
The purification protocol is as follows:
Add 500 ul of STREAMLINE™ rProtein A beads to each BioRad column. The beads should be in 20% ethanol. The composition of the bead slurry should be 50% beads, 50% liquid.
Once the protein A beads are in the column they should be washed with 5 mls of Wash buffer #2 (discard the flow through)
Add 10 mls of supernatant to the BioRad column. During this step the antibodies will bind to the protein A beads. (discard the flow through)
Wash away undesired excess proteins by adding 5 mls of Wash buffer #1 to the column. (discard the flow through)
Wash the column again by adding 5 mls of Wash buffer #2 (discard the flow through)
Add 1 ml of Neutralization buffer to the 15 ml protein collection tube.
Place the BioRad® column into the 15 ml collection tube.
Add 3 mls of Elution buffer to the BioRad® column. This will remove the desired antibodies from the protein A beads.
Collect the eluted protein in the 15 ml protein collection tube.
Determine the concentration of the eluted protein by Bradford assay (use 10 ul of protein for Bradford assay).

To quantify the relative amount of each glycoform, the N-glycosidase F released glycans were labeled with 2-aminobenzidine (2-AB) and analyzed by HPLC as described in Choi et al., Proc. Natl. Acad. Sci. USA 100: 5022-5027 (2003) and Hamilton et al., Science 313: 1441-1443 (2006). Table 12 shows glycan profile of the produced antibodies (NQP=no quantification possible).

TABLE 12

| | M5 | G2 | M7 | M8 | A1 | A1H | A2 | HM |
|---|---|---|---|---|---|---|---|---|
| YGLY4563 | 2.4 | 3.2 | 2.8 | 2.5 | 7.9 | 9.6 | 67.3 | 4.3 |
| YGLY23294 | 16.9 | NQP | — | — | 23.4 | — | 59.7 | — |
| YGLY23280 | 20.6 | NQP | — | — | 16.3 | — | 63.1 | — |
| YGLY23301 | 15.5 | — | — | — | 21.9 | — | 59.4 | — |
| YGLY25259 | 27.7 | NQP | — | — | 23.9 | — | 48.3 | — |
| YGLY23305 | 29.6 | NQP | — | — | 18.1 | — | 52.4 | — |

Figure 21A:
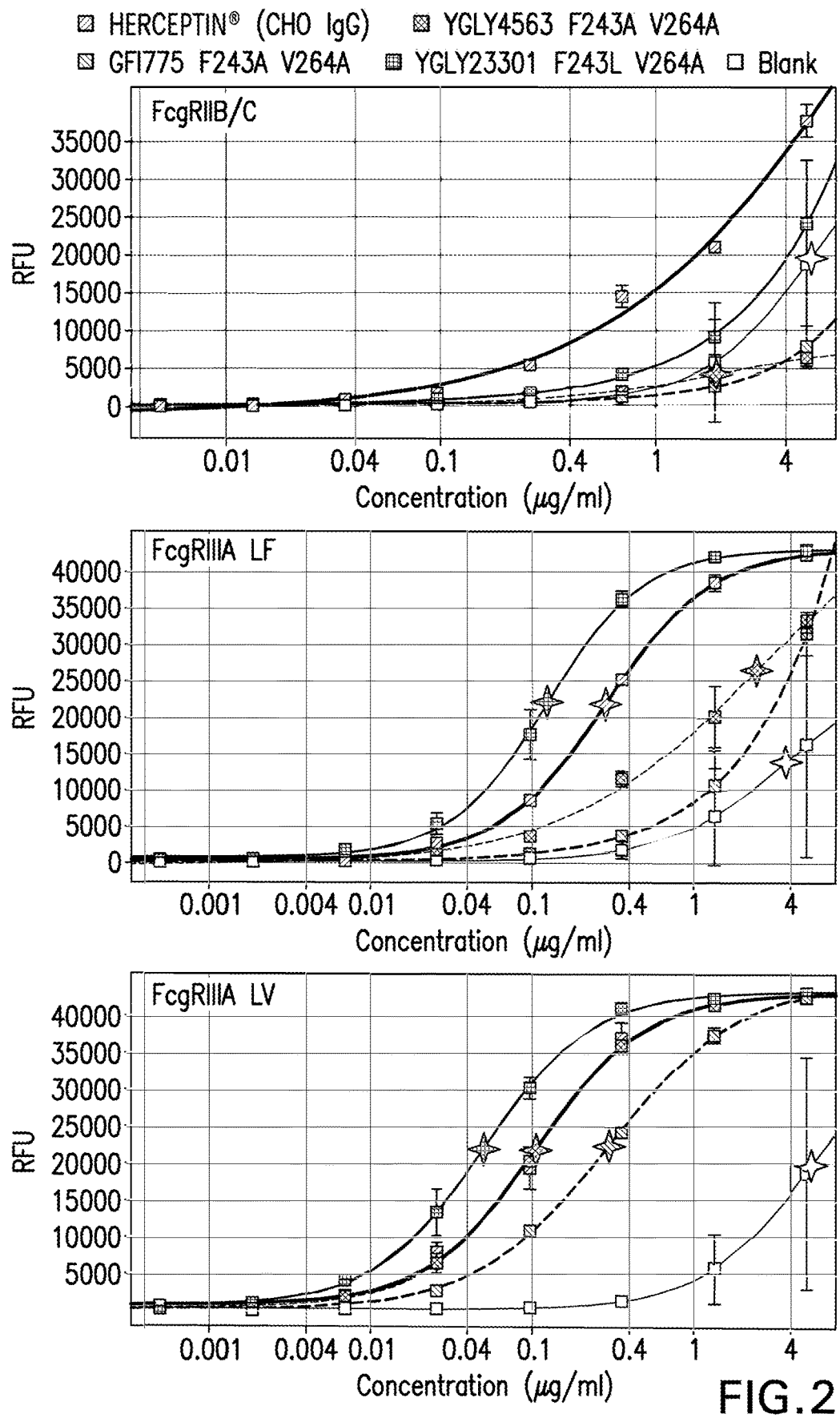

The binding of the above mutants to various Fcγ receptors was determined using the method described in Example 11. The results are shown in FIG. 21 and Tables 13 and 14.

TABLE 13

Binding Affinity as compared to the F243A/V264A double mutein

| Sample | FcγRIIb/c | FcγIIIa LF | FcγIIIa LV |
|---|---|---|---|
| YGLY23301 | ↑ 2 | ↑ 20 | ↑ 2.2 |
| YGLY23305 | ↑ 12 | ↑ 15 | ↑ 3 |
| YGLY23280 | no change | ↓ 4 | ↑ 3 |
| YGLY23294 | ↑ 50 | ↑ >100 | ↑ 9 |
| YGLY25259 | no change | ↑ >30 | ↑ 4 |

TABLE 14

Binding Affinity as compared to commercially available Herceptin

| Sample | FcγRIIb/c | FcγIIIa LF | FcγIIIa LV |
|---|---|---|---|
| YGLY4563 | Non-binding | ↓ 8.4 | no change |
| YGLY23301 | ↓ 3 | ↑ 2.4 | ↑ 2.2 |
| YGLY23305 | ↑ 2 | no change | no change |
| YGLY23280 | ↓ 3 | ↓ 25 | ↓ 6 |
| YGLY23294 | ↑ >15 | ↑ 10 | ↑ 3.5 |
| YGLY25259 | ↓ 2.5 | ↑ 2.5 | no change |

Example 23

Anti-PCKS9 Parent Antibody and Fc Muteins

An anti-PCSK9 antibody having the heavy chain amino acid sequence of SEQ ID NO:13 and the light chain amino acid sequence of SEQ ID NO:14 was also constructed, and mutations F243A and V264A of the heavy chain were introduced as described in Example 2. The heavy chain amino acid sequence of the anti-PCSK9 double mutein is shown in SEQ ID NO:15. The wild-type and double mutein forms of the antibody were expressed in Glycoengineered *Pichia* GFI5.0 and GFI6.0, and purified according to the procedures described in Examples 3-7, and their ability to bind the various Fcγ receptors was determined using the procedures described in Example 11. The anti-PCSK9 double mutein antibody (produced in GFI6.0, comprising the heavy chain amino acid sequence of SEQ ID NO:15 and the light chain amino acid sequence of SEQ ID NO:14), when compared to the parent antibody (produced in GFI5.0) had approximately a 4 fold reduction in binding to FcγR1, a 8-60 fold reduction in binding to FcγRIIIa LF, a 2-6 fold reduction in binding to FcγRIIIa LV, and no detectable binding to FcγRIIa or FcγRIIb/c.

Example 24

Effect of the Anti-Her2 Antibody and its Fc Muteins in a Collagen-Antibody Induced Arthritis (IAA) Model MODEL INDUCTION: AIA (Antibody induced arthritis) is induced with a commercial Arthrogen-CIA® arthritogenic monoclonal antibody (purchased from Chondrex) consisting of a cocktail of 5 monoclonal antibodies, clone A2-10 (IgG2a), F10-21 (IgG2a), D8-6 (IgG2a), D1-2G(IgG2b), and D2-112 (IgG2b), that recognize the conserved epitopes on various species of type II collagen.

ANIMALS: 10 week old B10.RIII male mice which are susceptible to arthritis induction without additional of co-stimulatory factors were used. These animals were purchased from Jackson Laboratory.

CLINICAL SCORING: Paw swelling was measured daily post-induction of arthritis. The severity of the disease was graded on a 0-3 scale per paw as follows: 0, normal; 1, swelling of one digit; 2, swelling of two or more digits; 3, swelling of the entire paw. The maximal clinical score per mouse is 12.

STUDY DESIGN: Arthritis was induced by passive transfer of 3 mg of anti-CII mAb pathogen cocktail IV on day 0.

All groups of mice were dosed on day minus 1. The Clinical Score was monitored for 7 days.

Groups of Mice were Treated Subcutaneously with Following Reagents:

| Group/Reagent | Lot | Dose |
|---|---|---|
| A. Naïve | *** | *** |
| B. Isotype IgG1 | 78ABY | 33 mpk |
| C. Asialyated Anti-Her2 | 38ADV | 33 mpk |
| D. α2,6 Sialyated Anti- Her2 | 37ADV | 33 mpk |
| E. muTNFR-Ig | 82ABW | 33 mpk |

All Groups n = 5 except group E which has an n = 4

An isotype IgG1 antibody was used as a control. The antibody bound to mouse anti-hexon and had the designation "27F11".

The sample identified as "Asialyated Anti-Her2" corresponds to the anti-Her2 antibody comprising the F243A/V264A mutations produced in GFI 5.0 strain YGLY19709. The YGLY19709 strain was derived from the anti-Her2 antibody producing strain YGLY13979, which was transformed with plasmid pGLY6301 for expressing LsSTT3d. Strain YGLY13979 and plasmid pGLY6301 are described in patent application: WO 2010/099186.

The sample identified as "α2,6 Sialyated Anti-Her2" corresponds to the anti-Her2 antibody comprising the F243A/V264A mutations produced in GFI 6.0 strain YGLY4563 (see Example 4).

mTNFR-Ig is an immunoadhesin (anti-TNF receptor Ig-fusion protein) comprising the extracellular domain of mTNFR2 connected to mIgG1 Fc starting at the hinge and spanning the CH2 and the CH3 regions, and comprising the amino acid sequence of SEQ ID NO:16 produced in CHO cells.

Figure 22:
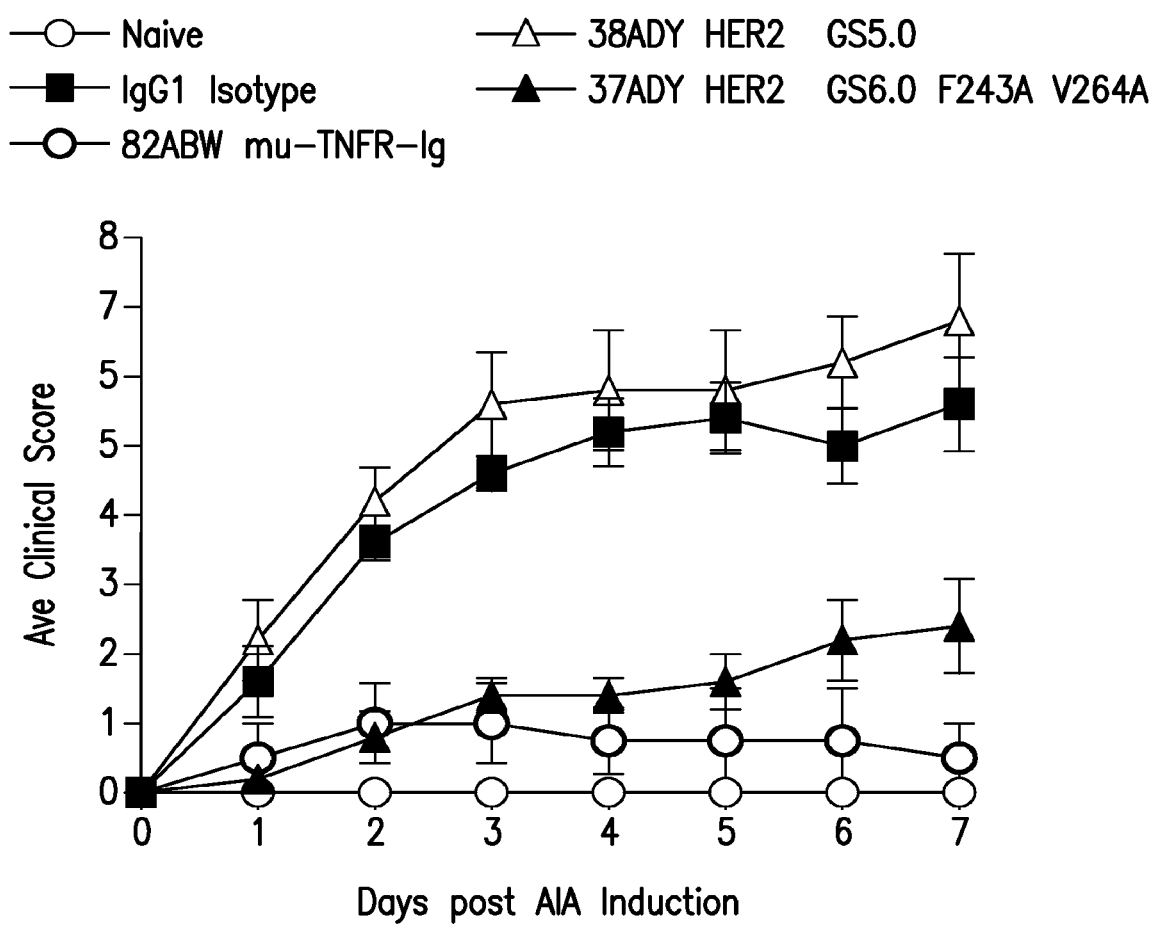
FIG. 22 is a graphic representation of the effect of the Fc muteins of the invention in an AIA model described in Example 24.

The results of these experiments are shown in FIG. 22.

SEQUENCE LISTING

| SEQ ID NO: | Description | Sequence |
|---|---|---|
| 1 | Heavy chain amino acid sequence of wt anti-HER antibody | EVQLVESGGGLVQPGGSLRLSCAASGFNIKDTYIHWVRQAPGKGLEWVARIYPTNGYTRYADSVK GRFTISADTSKNTAYLQMNSLRAEDTAVYYCSRWGGDGFYAMDYWGQGTLVTVSSASTKGPSVFP LAPSSKSTSGGTAALGCLVKDYFPEPVTVSWNSGALTSGVHTFPAVLQSSGLYSLSSVVTVPSSS LGTQTYICNVNHKPSNTKVDKKVEPKSCDKTHTCPPCPAPELLGGPSVFLFPPKPKDTLMISRTP EVTCVVVDVSHEDPEVKFNWYVDGVEVHNAKTKPREEQYNSTYRVVSVLTVLHQDWLNGKEYKCK VSNKALPAPIEKTISKAKGQPREPQVYTLPPSRDELTKNQVSLTCLVKGFYPSDIAVEWESNGQP ENNYKTTPPVLDSDGSFFLYSKLTVDKSRWQQGNVFSCSVMHEALHNHYTQKSLSLSPGK |
| 2 | Light chain amino acid sequence of anti-HER antibody | DIQMTQSPSSLSASVGDRVTITCRASQDVNTAVAWYQQKPGKAPKLLIYSASFLYSGVPSRFSGS RSGTDFTLTISSLQPEDFATYYCQQHYTTPPTFGQGTKVEIKRTVAAPSVFIFPPSDEQLKSGTA SVVCLLNNFYPREAKVQWKVDNALQSGNSQESVTEQDSKDSTYSLSSTLTLSKADYEKHKVYACE VTHQGLSSPVTKSFNRGEC |
| 3 | Primer | GGTCCTTCCGTTTTTTTGGCCCCACCAAAGCCAAAGGACACTTTG |
| 4 | Primer | GTGTCCTTTGGCTTTGGTGGGGCCAAAAAAACGGAAGGACCACC |
| 5 | Primer | gttacatgtgttgttgctgacgtttctcacgag |
| 6 | Primer | GGTCCTCGTGAGAAACGTCAGCAACAACACATG |
| 7 | Alpha-mating factor DNA sequence | GAATTCGAAACGATGAGATTTCCTTCAATTTTTACTGCTGTTTTATTCGCAGCATCCTCCGCATT AGCT |
| 8 | Alpha-mating factor amino acid sequence | MRFPSIFTAVLFAASSALA |
| 9 | Heavy chain amino acid sequence of double mutein anti-HER antibody | EVQLVESGGGLVQPGGSLRLSCAASGFNIKDTYIHWVRQAPGKGLEWVARIYPTNGYTRYADSVK GRFTISADTSKNTAYLQMNSLRAEDTAVYYCSRWGGDGFYAMDYWGQGTLVTVSSASTKGPSVFP LAPSSKSTSGGTAALGCLVKDYFPEPVTVSWNSGALTSGVHTFPAVLQSSGLYSLSSVVTVPSSS LGTQTYICNVNHKPSNTKVDKKVEPKSCDKTHTCPPCPAPELLGGPSVFLAPPKPKDTLMISRTP EVTCVVADVSHEDPEVKFNWYVDGVEVHNAKTKPREEQYNSTYRVVSVLTVLHQDWLN GKEYKCKVSNKALPAPIEKTISKAKGQPREPQVYTLPPSRDELTKNQVSLTCLVKGFYPSDIAVE WESNGQPENNYKTTPPVLDSDGSFFLYSKLTVDKSRWQQGNVFSCSVMHEALHNHYTQKSLSLSP GK |

| 10 | heavy chain amino acid sequence of wildtype anti-TNF alpha antibody | E | V | Q | L | V | E | S | G | G | G | L | V | Q | P | G | R | S | L | R | L | S | C |
|---|---|---|---|---|---|---|---|---|---|---|---|---|---|---|---|---|---|---|---|---|---|---|---|
| | | A | A | S | G | F | T | F | D | D | Y | A | M | H | W | V | R | Q | A | P | G | K | G |
| | | L | E | W | V | S | A | I | T | W | N | S | G | H | I | D | Y | A | D | S | V | E | G |
| | | R | F | T | I | S | R | D | N | A | K | N | S | L | Y | L | Q | M | N | S | L | R | A |
| | | E | D | T | A | V | Y | Y | C | A | K | V | S | Y | L | S | T | A | S | S | L | D | Y |
| | | W | G | Q | G | T | L | V | T | V | S | S | A | S | T | K | G | P | S | V | F | P | L |
| | | A | P | S | S | K | S | T | S | G | G | T | A | A | L | G | C | L | V | K | D | Y | F |
| | | P | E | P | V | T | V | S | W | N | S | G | A | L | T | S | G | V | H | T | F | P | A |
| | | V | L | Q | S | S | G | L | Y | S | L | S | S | V | V | T | V | P | S | S | S | L | G |
| | | T | Q | T | Y | I | C | N | V | N | H | K | P | S | N | T | K | V | D | K | K | V | E |
| | | P | K | S | C | D | K | T | H | T | C | P | P | C | P | A | P | E | L | L | G | G | P |
| | | S | V | F | L | F | P | P | K | P | K | D | T | L | M | I | S | R | T | P | E | V | T |
| | | C | V | V | V | D | V | S | H | E | D | P | E | V | K | F | N | W | Y | V | D | G | V |
| | | E | V | H | N | A | K | T | K | P | R | E | E | Q | Y | N | S | T | Y | R | V | V | S |
| | | V | L | T | V | L | H | Q | D | W | L | N | G | K | E | Y | K | C | K | V | S | N | K |

SEQUENCE LISTING

| SEQ ID NO | Description | Sequence |
|---|---|---|
| | | A L P A P I E K T I S K A K G Q P R E P Q V |
| | | Y T L P P S R D E L T K N Q V S L T C L V K |
| | | G F Y P S D I A V E W E S N G Q P E N N Y K |
| | | T T P P V L D S D G S F F L Y S K L T V D K |
| | | S R W Q Q G N V F S C S V M H E A L H N H Y |
| | | T Q K S L S L S P G |
| 11 | Light chain amino acid sequence of anti-TNF alpha antibody | D I Q M T Q S P S S L S A S V G D R V T I T |
| | | C R A S Q G I R N Y L A W Y Q Q K P G K A P |
| | | K L L I Y A A S T L Q S G V P S R F S G S G |
| | | S G T D F T L T I S S L Q P E D V A T Y Y C |
| | | Q R Y N R A P Y T F G Q G T K V E I K R T V |
| | | A A P S V F I F P P S D E Q L K S G T A S V |
| | | V C L L N N F Y P R E A K V Q W K V D N A L |
| | | Q S G N S Q E S V T E Q D S K D S T Y S L S |
| | | S T L T L S K A D Y E K H K V Y A C E V T H |
| | | Q G L S S P V T K S F N R G E C |
| 12 | Heavy chain amino acid sequence of double mutein anti-TNF alpha antibody | E V Q L V E S G G G L V Q P G R S L R L S C |
| | | A A S G F T F D D Y A M H W V R Q A P G K G |
| | | L E W V S A I T W N S G H I D Y A D S V E G |
| | | R F T I S R D N A K N S L Y L Q M N S L R A |
| | | E D T A V Y Y C A K V S Y L S T A S S L D Y |
| | | W G Q G T L V T V S S A S T K G P S V F P L |
| | | A P S S K S T S G G T A A L G C L V K D Y F |
| | | P E P V T V S W N S G A L T S G V H T F P A |
| | | V L Q S S G L Y S L S S V V T V P S S S L G |
| | | T Q T Y I C N V N H K P S N T K V D K K V E |
| | | P K S C D K T H T C P P C P A P E L L G G P |
| | | S V F L A P P K P K D T L M I S R T P E V T |
| | | C V V A D V S H E D P E V K F N W Y V D G V |
| | | E V H N A K T K P R E E Q Y N S T Y R V V S |
| | | V L T V L H Q D W L N G K E Y K C K V S N K |
| | | A L P A P I E K T I S K A K G Q P R E P Q V |
| | | Y T L P P S R D E L T K N Q V S L T C L V K |
| | | G F Y P S D I A V E W E S N G Q P E N N Y K |
| | | T T P P V L D S D G S F F L Y S K L T V D K |
| | | S R W Q Q G N V F S C S V M H E A L H N H Y |
| | | T Q K S L S L S P G |
| 13 | Heavy chain amino acid sequence of wt anti-PCSK9 antibody | QVQLVQSGAEVKKPGASVKVSCKVSGYTFTDYYMNWVRQAPGQGLEWIGDINPNNGGAIYNQKFK |
| | | GRATLTVDKSTSTAYMELRSLRSDDTAVYYCTSGIITEIAEDFWGQGTLVTV S S A S |
| | | T K G P S V F P L A P S S K S T S G G T A A |
| | | L G C L V K D Y F P E P V T V S W N S G A L |
| | | T S G V H T F P A V L Q S S G L Y S L S S V |
| | | V T V P S S S L G T Q T Y I C N V N H K P S |
| | | N T K V D K K V E P K S C D K T H T C P P C |
| | | P A P E L L G G P S V F L F P P K P K D T L |
| | | M I S R T P E V T C V V V D V S H E D P E V |
| | | K F N W Y V D G V E V H N A K T K P R E E Q |
| | | Y N S T Y R V V S V L T V L H Q D W L N G K |
| | | E Y K C K V S N K A L P A P I E K T I S K A |
| | | K G Q P R E P Q V Y T L P P S R D E L T K N |
| | | Q V S L T C L V K G F Y P S D I A V E W E S |
| | | N G Q P E N N Y K T T P P V L D S D G S F F |
| | | L Y S K L T V D K S R W Q Q G N V F S C S V |
| | | M H E A L H N H Y T Q K S L S L S P G |
| 14 | Light chain amino acid sequence of wt anti-PCSK9 antibody | DIQMTQSPSSLSASVGDRVTITCKASQNVGTNVVWYQQKPGKAPKALIHSASYRYSGVPSRFSGS GSGTDFTLTISSLQPEDFATYYCQQYKTYPYTFGQGTKVEIKRTVAAPSVFIFPPSDEQLKSGTA SVVCLLNNFYPREAKVQWKVDNALQSGNSQESVTEQDSKDSTYSLSSTLTLSKADYEKHKVYACE VTHQGLSSPVTKSFNRGEC |
| 15 | Heavy chain amino acid sequence of double mutein anti-PCSK9 antibody | QVQLVQSGAEVKKPGASVKVSCKVSGYTFTDYYMNWVRQAPGQGLEWIGDINPNNGGAIYNQKFK |
| | | GRATLTVDKSTSTAYMELRSLRSDDTAVYYCTSGIITEIAEDFWGQGTLVTV S S A S |
| | | T K G P S V F P L A P S S K S T S G G T A A |
| | | L G C L V K D Y F P E P V T V S W N S G A L |
| | | T S G V H T F P A V L Q S S G L Y S L S S V |
| | | V T V P S S S L G T Q T Y I C N V N H K P S |
| | | N T K V D K K V E P K S C D K T H T C P P C |
| | | P A P E L L G G P S V F L A P P K P K D T L |
| | | M I S R T P E V T C V V A D V S H E D P E V |

SEQUENCE LISTING

| SEQ ID NO: Description | Sequence |
|---|---|
| | K F N W Y V D G V E V H N A K T K P R E E Q |
| | Y N S T Y R V V S V L T V L H Q D W L N G K |
| | E Y K C K V S N K A L P A P I E K T I S K A |
| | K G Q P R E P Q V Y T L P P S R D E L T K N |
| | Q V S L T C L V K G F Y P S D I A V E W E S |
| | N G Q P E N N Y K T T P P V L D S D G S F F |
| | L Y S K L T V D K S R W Q Q G N V F S C S V |
| | M H E A L H N H Y T Q K S L S L S P G |
| 16 anti-TNF Ig-fusion protein | Vvltpykpepgyecqisqeyydrkaqmccakcppgqyvkhfcnktsdtvcadceasmytqvwnqf<br>rtclscssscttdqveiractkqqnrvcaceagrycalkthsgscrqcmrlskcgpgfgvassra<br>pngnvlckacapgtfsdttsstdvcrphricsilaipgnastdavcapespt1saiprt1yvsqp<br>eptrsqpldqepgpsqtpsi1ts1gstpiieqstkgggsvprdcgckpcictvpevssvfifppk<br>pkdv1titl1tpkvtcvvvdiskddpevqfswfvddvevhtaqtkpreeqfnstfrsyse1pimhq<br>dw1ngkefkcrvnsaafpapiektisktkgrpkapqvytippkeqmakdkvs1tcmitdffped<br>itvewqwngqpaenykntqpimdtdgsyfvysklnvqksnweagntftcsvlheglhnhhteks1<br>shspgk |
| 17 Extracellular domain of FcγRIIb/c and histidine tag | M R F P S I F T A V L F A A S S A L A A P V<br>N T T T E D E T A Q I P A E A V I G Y S D L<br>E G D F D V A V L P F S N S T N N G L L F I<br>N T T I A S I A A K E E G V S L E K R A P P<br>K A V L K L E P Q W I N V L Q E D S V T L T<br>C R G T H S P E S D S I Q W F H N G N L I P<br>T H T Q P S Y R F K A N N N D S G E Y T C Q<br>T G Q T S L S D P V H L T V L S E W L V L Q<br>T P H L E F Q E G E T I V L R C H S W K D K<br>P L V K V T F F Q N G K S K K F S R S D P N<br>F S I P Q A N H S H S G D Y H C T G N I G Y<br>T L Y S S K P V T I T V Q A P G G G H H H H<br>H H H H H |
| 18 Fc region | T C P P C P A P E L L G G P S V F L<br>F P P K P K D T M I S S R T P E V T<br>C V V V D V S H E D P E V K F N W Y<br>V D G V E V H N A K T K P R E E Q Y<br>N S T Y R V V S V L T V L H Q D W L<br>N G K E Y K C K V S N K A L P A P I<br>E K T I S K A K G Q P R E P Q V Y T<br>L P P S R D E L T K N Q V S L T C L<br>V K G F Y P S D I A V E W E S N G Q<br>P E N N Y K T T P P V L D S D G S F<br>F L Y S K L T V D K S R W Q Q G N V<br>F S C S V M H E A L H N H Y T Q K S<br>L S L S P G |
| 19 Fc region | E P K S C D K T H T C P P C P A P E<br>L L G G P S V F L F P P K P K D T L<br>M I S R T P E V T C V V V D V S H E<br>D P E V K F N W Y V D G V E V H N A<br>K T K P R E E Q Y N S T Y R V V S V<br>L T V L H Q D W L N G K E Y K C K V<br>S N K A L P A P I E K T I S K A K G<br>Q P R E P Q V Y T L P P S R D E L T<br>K N Q V S L T C L V K G F Y P S D I<br>A V E W E S N G Q P E N N Y K T T P<br>P V L D S D G S F F L Y S K L T V D<br>K S R W Q Q G N V F S C S V M H E A<br>L H N H Y T Q K S L S L S P G |

While the present invention is described herein with reference to illustrated embodiments, it should be understood that the invention is not limited hereto. Those having ordinary skill in the art and access to the teachings herein will recognize additional modifications and embodiments within the scope thereof.

What is claimed:

1. A method for increasing the bioavailability of an Fc-containing polypeptide when administered subcutaneously, comprising:
   introducing mutations at amino acid positions 243 and 264 of the Fc region of an Fc-containing polypeptide comprising the amino acid sequence set forth in SEQ ID NO: 18, wherein the mutation at position 243 is selected from the group consisting of: F243A, F243 G, F243 S, F243 T, F243V, F243L, F243I, F243D, F243Y, F243E, F243R, F243W, and F243K and the mutation at position 264 is selected from the group consisting of: V264A, V264G, V264S, V264T, V264D, V264E, V264K, V264W, V264H, V264P, V264N, V264Q and V264L,
   wherein the numbering is according to the EU index as in Kabat; and
   wherein the bioavailability of the Fc-containing polypeptide comprising the mutations is increased when the Fc-containing polypeptide is administered subcutaneously compared to subcutaneous administration of an Fc-containing polypeptide without said mutations.

2. The method of claim 1, wherein the mutations are F243A and V264A.

3. The method of claim 1, wherein the Fc-containing polypeptide is produced in a genetically modified host cell that has been genetically engineered to produce an Fc-containing polypeptide having sialylated N-glycans.

4. The method of claim 1, wherein the Fc-containing polypeptide is an antibody.

5. The method of claim 1, wherein the Fc-containing polypeptide comprises sialylated N-glycans.

6. The method of claim 3, wherein the sialic acid residues in the sialylated N-glycans are attached via α-2,6 linkages.

7. The method of claim 1, wherein the Fc-containing polypeptide has one or more of the following properties when compared to a parent Fc-containing polypeptide: reduced effector function, increased anti-inflammatory properties, increased sialylation, and reduced binding to FcγRI, FcγRIIa, FcγRIIb and FcγRIIIa.

8. A method for producing an Fc-containing polypeptide having increased bioavailability when administered subcutaneously, comprising:
   (a) providing a host cell comprising a nucleic acid molecule encoding an Fc-containing polypeptide comprising the amino acid sequence set forth in SEQ ID NO: 18 and having alanine at positions 243 and 264 of the Fc, wherein the host cell has been genetically engineered to produce glycoproteins having sialylated N-glycans in which the sialic acid residues in the sialylated N-glycans are attached via α-2,6 linkages, and wherein the Fc numbering is according to the EU index as in Kabat;
   (b) culturing the transformed host cell under conditions that induce expression of the nucleic acid molecule encoding the Fc-containing polypeptide to produce an Fc-containing polypeptide comprising sialylated N-glycans in which the sialic acid residues in the sialylated N-glycans are attached via α-2,6 linkages; and (c) isolating the Fc-containing polypeptide comprising the sialylated N-glycans in which the sialic acid residues in the sialylated N-glycans are attached via α-2,6 linkages from the transformed host cell to produce the Fc-containing polypeptide having increased bioavailability when administered subcutaneously compared to subcutaneous administration of an Fc-containing polypeptide without said mutations.

9. The method of claim 8, wherein the host cell is a yeast host cell.

10. The method of claim 9, where the yeast host cell is *Pichia pastoris*.

11. The method of claim 8, wherein the Fc-containing polypeptide is an antibody.

12. The method of claim 8, wherein the Fc-containing polypeptide comprises sialylated N-glycans.

13. The method of claim 12, wherein the sialic acid residues in the sialylated N-glycans are attached via α-2,6 linkages.

* * * * *

SEQUENCE LISTING

<160> NUMBER OF SEQ ID NOS: 19

<210> SEQ ID NO 1

```
<211> LENGTH: 450
<212> TYPE: PRT
<213> ORGANISM: Artificial Sequence
<220> FEATURE:
<223> OTHER INFORMATION: antibody heavy chain

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380
```

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 2
<211> LENGTH: 214
<212> TYPE: PRT
<213> ORGANISM: Artificial Sequence
<220> FEATURE:
<223> OTHER INFORMATION: antibody light chain

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 45
<212> TYPE: DNA
<213> ORGANISM: Artificial Sequence
<220> FEATURE:
<223> OTHER INFORMATION: primer

<400> SEQUENCE: 3
ggtccttccg ttttttggc cccaccaaag ccaaaggaca ctttg        45

<210> SEQ ID NO 4
<211> LENGTH: 44
<212> TYPE: DNA
<213> ORGANISM: Artificial Sequence
<220> FEATURE:
<223> OTHER INFORMATION: primer

<400> SEQUENCE: 4
gtgtcctttg ctttggtgg ggccaaaaaa acggaaggac cacc        44

<210> SEQ ID NO 5
<211> LENGTH: 33
<212> TYPE: DNA
<213> ORGANISM: Artificial Sequence
<220> FEATURE:
<223> OTHER INFORMATION: primer

<400> SEQUENCE: 5
gttacatgtg ttgttgctga cgtttctcac gag        33

<210> SEQ ID NO 6
<211> LENGTH: 33
<212> TYPE: DNA
<213> ORGANISM: Artificial Sequence
<220> FEATURE:
<223> OTHER INFORMATION: primer

<400> SEQUENCE: 6
ggtcctcgtg agaaacgtca gcaacaacac atg        33

<210> SEQ ID NO 7
<211> LENGTH: 69
<212> TYPE: DNA
<213> ORGANISM: Artificial Sequence
<220> FEATURE:
<223> OTHER INFORMATION: signal sequence

<400> SEQUENCE: 7
gaattcgaaa cgatgagatt tccttcaatt tttactgctg ttttattcgc agcatcctcc        60
gcattagct        69

<210> SEQ ID NO 8
<211> LENGTH: 19
<212> TYPE: PRT
<213> ORGANISM: Artificial Sequence
<220> FEATURE:
<223> OTHER INFORMATION: signal sequence

<400> SEQUENCE: 8

Met Arg Phe Pro Ser Ile Phe Thr Ala Val Leu Phe Ala Ala Ser Ser
1               5                   10                  15

Ala Leu Ala

<210> SEQ ID NO 9
<211> LENGTH: 450
<212> TYPE: PRT
<213> ORGANISM: Artificial Sequence
<220> FEATURE:
<223> OTHER INFORMATION: antibody heavy chain

<400> SEQUENCE: 9

Glu Val Gln Leu Val Glu Ser Gly Gly Gly Leu Val Gln Pro Gly Gly
1               5                   10                  15

-continued

```
Ser Leu Arg Leu Ser Cys Ala Ala Ser Gly Phe Asn Ile Lys Asp Thr
         20                  25                  30

Tyr Ile His Trp Val Arg Gln Ala Pro Gly Lys Gly Leu Glu Trp Val
         35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
             100                 105                 110

Gly Thr Leu Val Thr Val Ser Ser Ala Ser Thr Lys Gly Pro Ser Val
         115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175

Leu Gln Ser Ser Gly Leu Tyr Ser Leu Ser Ser Val Val Thr Val Pro
             180                 185                 190

Ser Ser Ser Leu Gly Thr Gln Thr Tyr Ile Cys Asn Val Asn His Lys
         195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Ala Pro Pro Lys Pro Lys Asp Thr Leu Met Ile
                 245                 250                 255

Ser Arg Thr Pro Glu Val Thr Cys Val Val Ala Asp Val Ser His Glu
             260                 265                 270

Asp Pro Glu Val Lys Phe Asn Trp Tyr Val Asp Gly Val Glu Val His
         275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                 325                 330                 335

Lys Thr Ile Ser Lys Ala Lys Gly Gln Pro Arg Glu Pro Gln Val Tyr
             340                 345                 350

Thr Leu Pro Pro Ser Arg Asp Glu Leu Thr Lys Asn Gln Val Ser Leu
         355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                 405                 410                 415

Lys Ser Arg Trp Gln Gln Gly Asn Val Phe Ser Cys Ser Val Met His
             420                 425                 430

Glu Ala Leu His Asn His Tyr Thr Gln Lys Ser Leu Ser Leu Ser Pro
```

```
                435                 440                 445
Gly Lys
    450

<210> SEQ ID NO 10
<211> LENGTH: 450
<212> TYPE: PRT
<213> ORGANISM: Artificial Sequence
<220> FEATURE:
<223> OTHER INFORMATION: antibody heavy chain

<400> SEQUENCE: 10

Glu Val Gln Leu Val Glu Ser Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
```

```
                340                 345                 350
Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 11
<211> LENGTH: 214
<212> TYPE: PRT
<213> ORGANISM: Artificial Sequence
<220> FEATURE:
<223> OTHER INFORMATION: antibody light chain

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 450
<212> TYPE: PRT
```

<213> ORGANISM: Artificial Sequence
<220> FEATURE:
<223> OTHER INFORMATION: antibody heavy chain

<400> SEQUENCE: 12

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Lys Val Ser Tyr Leu Ser Thr Ala Ser Ser Leu Asp Tyr Trp Gly
        100                 105                 110

Gln Gly Thr Leu Val Thr Val Ser Ser Ala Ser Thr Lys Gly Pro Ser
    115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Ala Pro Pro Lys Pro Lys Asp Thr Leu Met
            245                 250                 255

Ile Ser Arg Thr Pro Glu Val Thr Cys Val Val Ala Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Asp Glu Leu Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro

```
                385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly
    450

<210> SEQ ID NO 13
<211> LENGTH: 448
<212> TYPE: PRT
<213> ORGANISM: Artificial Sequence
<220> FEATURE:
<223> OTHER INFORMATION: antibody heavy chain

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Asp Tyr
                20                  25                  30

Tyr Met Asn Trp Val Arg Gln Ala Pro Gly Gln Gly Leu Glu Trp Ile
            35                  40                  45

Gly Asp Ile Asn Pro Asn Asn Gly Gly Ala Ile Tyr Asn Gln Lys Phe
    50                  55                  60

Lys Gly Arg Ala Thr Leu Thr Val Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Thr Ser Gly Ile Ile Thr Glu Ile Ala Glu Asp Phe Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
```

```
                290                 295                 300
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

<210> SEQ ID NO 14
<211> LENGTH: 214
<212> TYPE: PRT
<213> ORGANISM: Artificial Sequence
<220> FEATURE:
<223> OTHER INFORMATION: antibody light chain

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
                20                  25                  30

Val Val Trp Tyr Gln Gln Lys Pro Gly Lys Ala Pro Lys Ala Leu Ile
                35                  40                  45

His Ser Ala Ser Tyr Arg Tyr Ser Gly Val Pro Ser Arg Phe Ser Gly
                50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Lys Thr Tyr Pro Tyr
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
```

-continued

<210> SEQ ID NO 15
<211> LENGTH: 448
<212> TYPE: PRT
<213> ORGANISM: Artificial Sequence
<220> FEATURE:
<223> OTHER INFORMATION: antibody heavy chain

<400> SEQUENCE: 15

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Asp Tyr
            20                  25                  30

Tyr Met Asn Trp Val Arg Gln Ala Pro Gly Gln Gly Leu Glu Trp Ile
        35                  40                  45

Gly Asp Ile Asn Pro Asn Asn Gly Gly Ala Ile Tyr Asn Gln Lys Phe
    50                  55                  60

Lys Gly Arg Ala Thr Leu Thr Val Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Thr Ser Gly Ile Ile Thr Glu Ile Ala Glu Asp Phe Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Ala Pro Pro Lys Pro Lys Asp Thr Leu Met Ile Ser
                245                 250                 255

Arg Thr Pro Glu Val Thr Cys Val Val Ala Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
```

```
                355                 360                 365
Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 16
<211> LENGTH: 461
<212> TYPE: PRT
<213> ORGANISM: Artificial Sequence
<220> FEATURE:
<223> OTHER INFORMATION: Fc fusion protein

<400> SEQUENCE: 16

Val Val Leu Thr Pro Tyr Lys Pro Glu Pro Gly Tyr Glu Cys Gln Ile
1               5                   10                  15

Ser Gln Glu Tyr Tyr Asp Arg Lys Ala Gln Met Cys Cys Ala Lys Cys
            20                  25                  30

Pro Pro Gly Gln Tyr Val Lys His Phe Cys Asn Lys Thr Ser Asp Thr
        35                  40                  45

Val Cys Ala Asp Cys Glu Ala Ser Met Tyr Thr Gln Val Trp Asn Gln
    50                  55                  60

Phe Arg Thr Cys Leu Ser Cys Ser Ser Cys Thr Thr Asp Gln Val
65                  70                  75                  80

Glu Ile Arg Ala Cys Thr Lys Gln Gln Asn Arg Val Cys Ala Cys Glu
                85                  90                  95

Ala Gly Arg Tyr Cys Ala Leu Lys Thr His Ser Gly Ser Cys Arg Gln
            100                 105                 110

Cys Met Arg Leu Ser Lys Cys Gly Pro Gly Phe Gly Val Ala Ser Ser
        115                 120                 125

Arg Ala Pro Asn Gly Asn Val Leu Cys Lys Ala Cys Ala Pro Gly Thr
    130                 135                 140

Phe Ser Asp Thr Thr Ser Ser Thr Asp Val Cys Arg Pro His Arg Ile
145                 150                 155                 160

Cys Ser Ile Leu Ala Ile Pro Gly Asn Ala Ser Thr Asp Ala Val Cys
                165                 170                 175

Ala Pro Glu Ser Pro Thr Leu Ser Ala Ile Pro Arg Thr Leu Tyr Val
            180                 185                 190

Ser Gln Pro Glu Pro Thr Arg Ser Gln Pro Leu Asp Gln Glu Pro Gly
        195                 200                 205

Pro Ser Gln Thr Pro Ser Ile Leu Thr Ser Leu Gly Ser Thr Pro Ile
    210                 215                 220

Ile Glu Gln Ser Thr Lys Gly Gly Ser Val Pro Arg Asp Cys Gly
225                 230                 235                 240

Cys Lys Pro Cys Ile Cys Thr Val Pro Glu Val Ser Ser Val Phe Ile
                245                 250                 255

Phe Pro Pro Lys Pro Lys Asp Val Leu Thr Ile Thr Leu Thr Pro Lys
            260                 265                 270

Val Thr Cys Val Val Val Asp Ile Ser Lys Asp Asp Pro Glu Val Gln
```

```
                275                 280                 285
Phe Ser Trp Phe Val Asp Asp Val Glu Val His Thr Ala Gln Thr Lys
    290                 295                 300

Pro Arg Glu Glu Gln Phe Asn Ser Thr Phe Arg Ser Val Ser Glu Leu
305                 310                 315                 320

Pro Ile Met His Gln Asp Trp Leu Asn Gly Lys Glu Phe Lys Cys Arg
                325                 330                 335

Val Asn Ser Ala Ala Phe Pro Ala Pro Ile Glu Lys Thr Ile Ser Lys
            340                 345                 350

Thr Lys Gly Arg Pro Lys Ala Pro Gln Val Tyr Thr Ile Pro Pro Pro
        355                 360                 365

Lys Glu Gln Met Ala Lys Asp Lys Val Ser Leu Thr Cys Met Ile Thr
370                 375                 380

Asp Phe Phe Pro Glu Asp Ile Thr Val Glu Trp Gln Trp Asn Gly Gln
385                 390                 395                 400

Pro Ala Glu Asn Tyr Lys Asn Thr Gln Pro Ile Met Asp Thr Asp Gly
                405                 410                 415

Ser Tyr Phe Val Tyr Ser Lys Leu Asn Val Gln Lys Ser Asn Trp Glu
            420                 425                 430

Ala Gly Asn Thr Phe Thr Cys Ser Val Leu His Glu Gly Leu His Asn
        435                 440                 445

His His Thr Glu Lys Ser Leu Ser His Ser Pro Gly Lys
450                 455                 460

<210> SEQ ID NO 17
<211> LENGTH: 269
<212> TYPE: PRT
<213> ORGANISM: Artificial Sequence
<220> FEATURE:
<223> OTHER INFORMATION: Histidine tagged protein

<400> SEQUENCE: 17

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Ala Pro Pro Lys Ala Val Leu Lys Leu Glu Pro
                85                  90                  95

Gln Trp Ile Asn Val Leu Gln Glu Asp Ser Val Thr Leu Thr Cys Arg
            100                 105                 110

Gly Thr His Ser Pro Glu Ser Asp Ser Ile Gln Trp Phe His Asn Gly
        115                 120                 125

Asn Leu Ile Pro Thr His Thr Gln Pro Ser Tyr Arg Phe Lys Ala Asn
    130                 135                 140

Asn Asn Asp Ser Gly Glu Tyr Thr Cys Gln Thr Gly Gln Thr Ser Leu
145                 150                 155                 160

Ser Asp Pro Val His Leu Thr Val Leu Ser Glu Trp Leu Val Leu Gln
                165                 170                 175

Thr Pro His Leu Glu Phe Gln Glu Gly Glu Thr Ile Val Leu Arg Cys
```

```
            180                 185                 190
His Ser Trp Lys Asp Lys Pro Leu Val Lys Val Thr Phe Phe Gln Asn
            195                 200                 205

Gly Lys Ser Lys Lys Phe Ser Arg Ser Asp Pro Asn Phe Ser Ile Pro
        210                 215                 220

Gln Ala Asn His Ser His Ser Gly Asp Tyr His Cys Thr Gly Asn Ile
225                 230                 235                 240

Gly Tyr Thr Leu Tyr Ser Ser Lys Pro Val Thr Ile Thr Val Gln Ala
                245                 250                 255

Pro Gly Gly Gly His His His His His His His His
                260                 265
```

<210> SEQ ID NO 18
<211> LENGTH: 222
<212> TYPE: PRT
<213> ORGANISM: Artificial Sequence
<220> FEATURE:
<223> OTHER INFORMATION: Fc region

<400> SEQUENCE: 18

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
            35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly
    210                 215                 220
```

<210> SEQ ID NO 19
<211> LENGTH: 231
<212> TYPE: PRT
<213> ORGANISM: Artificial Sequence
<220> FEATURE:
<223> OTHER INFORMATION: Fc region

<400> SEQUENCE: 19

-continued

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70              75                      80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225             230
```